US008951731B2

(12) United States Patent
Drmanac et al.

(10) Patent No.: US 8,951,731 B2
(45) Date of Patent: Feb. 10, 2015

(54) SEQUENCE ANALYSIS USING DECORATED NUCLEIC ACIDS

(75) Inventors: Radoje Drmanac, Los Altos Hills, CA (US); Snezana Drmanac, Los Altos Hills, CA (US)

(73) Assignee: Complete Genomics, Inc., Mountain View, CA (US)

(*) Notice: Subject to any disclaimer, the term of this patent is extended or adjusted under 35 U.S.C. 154(b) by 787 days.

(21) Appl. No.: 12/252,280

(22) Filed: Oct. 15, 2008

(65) Prior Publication Data

US 2009/0111115 A1 Apr. 30, 2009

Related U.S. Application Data

(60) Provisional application No. 60/980,132, filed on Oct. 15, 2007, provisional application No. 60/980,306, filed on Oct. 16, 2007, provisional application No. 60/980,711, filed on Oct. 17, 2007, provisional application No. 60/981,046, filed on Oct. 18, 2007.

(51) Int. Cl.
*C12Q 1/68* (2006.01)
*C12P 19/34* (2006.01)

(52) U.S. Cl.
CPC ............ *C12Q 1/6869* (2013.01); *C12Q 1/6825* (2013.01); *C12Q 1/6874* (2013.01)
USPC .......... 435/6.12; 435/91.1; 435/91.2

(58) Field of Classification Search
USPC .................. 435/6, 91.1, 91.2, 6.12
See application file for complete search history.

(56) References Cited

U.S. PATENT DOCUMENTS

| | | | |
|---|---|---|---|
| 4,719,179 A | 1/1988 | Barany | 435/172.1 |
| 4,883,750 A | 11/1989 | Whiteley | 435/6 |
| 5,091,302 A | 2/1992 | Newman | 435/6 |
| 5,124,246 A | 6/1992 | Urdea | 435/6 |
| 5,143,854 A | 9/1992 | Pirrung | 436/518 |
| 5,175,270 A * | 12/1992 | Nilsen et al. | 435/6 |
| 5,202,231 A | 4/1993 | Drmanac | 435/6 |
| 5,223,414 A | 6/1993 | Zarling | 435/6 |
| 5,273,881 A | 12/1993 | Sena | 425/6 |
| 5,405,519 A | 4/1995 | Schwartz | 204/299 |
| 5,427,930 A * | 6/1995 | Birkenmeyer et al. | 435/91.52 |
| 5,474,796 A | 12/1995 | Brennan | 427/2.13 |
| 5,508,169 A | 4/1996 | Deugau | 435/6 |
| 5,525,464 A | 6/1996 | Drmanac | 435/6 |
| 5,559,664 A | 9/1996 | Dogul | 361/191 |
| 5,632,957 A | 5/1997 | Heller | 422/68.1 |
| 5,641,658 A | 6/1997 | Adams | 435/91.2 |
| 5,707,797 A * | 1/1998 | Windle | 435/6 |
| 5,720,928 A | 2/1998 | Schwartz | 422/186 |
| 5,728,524 A | 3/1998 | Sibson | 435/6 |
| 5,744,305 A | 4/1998 | Fodor | 435/6 |
| 5,800,992 A | 9/1998 | Fodor | 435/6 |
| 5,840,862 A * | 11/1998 | Bensimon et al. | 536/22.1 |
| 5,851,769 A * | 12/1998 | Gray et al. | 435/6 |
| 5,866,337 A | 2/1999 | Schon | 435/6 |
| 5,871,921 A | 2/1999 | Landegren | 435/66 |
| 5,888,737 A | 3/1999 | Dubridge et al. | 435/6 |
| 6,004,755 A | 12/1999 | Wang | 435/6 |
| 6,013,445 A | 1/2000 | Albrecht | 435/6 |
| 6,045,994 A | 4/2000 | Zabeau | 435/6 |
| 6,136,537 A | 10/2000 | Macevicz | 435/6 |
| 6,143,495 A | 11/2000 | Lizardi | 435/6 |
| 6,143,527 A | 11/2000 | Pachuk | 435/91.1 |
| 6,147,198 A | 11/2000 | Schwartz | 536/23.1 |
| 6,150,089 A | 11/2000 | Schwartz | 435/6 |
| 6,210,891 B1 | 4/2001 | Nyren | 435/6 |
| 6,210,894 B1 | 4/2001 | Brennan | 435/6 |
| 6,214,246 B1 | 4/2001 | Craighead | 216/56 |
| 6,255,469 B1 | 7/2001 | Seeman | 536/23.1 |
| 6,267,872 B1 | 7/2001 | Akeson | 205/775 |
| 6,270,961 B1 | 8/2001 | Drmanac | 435/6 |
| 6,291,183 B1 | 9/2001 | Pirrung | 435/6 |
| 6,294,136 B1 | 9/2001 | Schwartz | 422/186 |
| 6,297,006 B1 | 10/2001 | Drmanac | 435/6 |
| 6,297,016 B1 | 10/2001 | Egholm | 435/6 |
| 6,306,597 B1 | 10/2001 | Macevicz | 435/6 |
| 6,309,824 B1 | 10/2001 | Drmanac | 435/6 |
| 6,316,229 B1 | 11/2001 | Lizardi | 435/91.1 |

(Continued)

FOREIGN PATENT DOCUMENTS

| | | |
|---|---|---|
| JP | 4-262799 | 8/1992 |
| JP | 4-304900 | 10/1992 |

(Continued)

OTHER PUBLICATIONS

Kagan, C.R, et al., "Electronic Energy Transfer in CdSe Quantom Dot Solids," Phys. Rev. Lett., vol. 76, No. 9, p. 1517-1520 (1996).
Björk, Per et al, "Single molecular imaging and spectroscopy of conjugated polyelectrolytes decorated on stretched aligned DNA," Nano Letters, v. 5, No. 10, p. 1948-1953 (Oct. 2005).
Björk, Per et al, "Soft lithographic printing of patterns of stretched DNA and DNA/electroic polymer wires by surface-energy modification and transfer," Small, v. 2, No. 8-9, (Aug. 2006).
Blanco et al., "Highly efficient DNA synthesis by the phage phi 29 DNA polymerase," J. Biol. Chem., v. 264, issue 15, p. 8935-8940 (1989).
Brenner et al, "Gene Expression Analysis by Massivly Parallel Signature Sequencing (MPSS) on Mircobead Arrays," Nature Biotechnology, v. 18, p. 630-634 (2000).

(Continued)

*Primary Examiner* — Kenneth R. Horlick
*Assistant Examiner* — Joyce Tung
(74) *Attorney, Agent, or Firm* — Kilpatrick Townsend & Stockton LLP

(57) ABSTRACT

The present invention provides a sequence interrogation chemistry that combines the accuracy and haplotype integrity of long-read sequencing with improved methods of preparing genomic nucleic acids and analyzing sequence information generated from those nucleic acids. The present invention encompasses compositions comprising decorated nucleic acids stretched on substrates. The present invention further encompasses methods of making stretched decorated nucleic acids and methods of using decorated nucleic acids to obtain sequence information.

36 Claims, 17 Drawing Sheets

(56) References Cited

U.S. PATENT DOCUMENTS

| | | | |
|---|---|---|---|
| 6,329,150 B1 | 12/2001 | Lizardi | 435/6 |
| 6,346,413 B1 | 2/2002 | Fodor | 435/287.2 |
| 6,355,419 B1* | 3/2002 | Alfenito | 435/6 |
| 6,355,432 B1 | 3/2002 | Fodor | 435/6 |
| 6,401,267 B1 | 6/2002 | Drmanac | 435/6 |
| 6,403,320 B1 | 6/2002 | Read | 435/6 |
| 6,413,722 B1 | 7/2002 | Arnold | 435/6 |
| 6,440,662 B1 | 8/2002 | Gerwen | 435/6 |
| 6,448,012 B1 | 9/2002 | Schwartz | 435/6 |
| 6,464,842 B1 | 10/2002 | Golovchenko | 204/192.13 |
| 6,472,156 B1 | 10/2002 | Wittwer | 435/6 |
| 6,491,871 B1 | 12/2002 | Fodor | 422/63 |
| 6,500,620 B2 | 12/2002 | Yu | 435/6 |
| 6,509,158 B1 | 1/2003 | Schwartz | 435/6 |
| 6,514,768 B1 | 2/2003 | Guire | 436/518 |
| 6,518,189 B1 | 2/2003 | Chou | 438/706 |
| 6,534,293 B1 | 3/2003 | Baranay | 435/91.2 |
| 6,544,732 B1 | 4/2003 | Chee | 435/6 |
| 6,573,369 B2 | 6/2003 | Henderson | 536/23.1 |
| 6,589,726 B1 | 7/2003 | Butler | 435/4 |
| 6,610,256 B2 | 8/2003 | Schwartz | 422/186 |
| 6,627,067 B1 | 9/2003 | Branton | 205/778 |
| 6,653,077 B1 | 11/2003 | Brenner | 435/6 |
| 6,673,615 B2 | 1/2004 | Denison | 436/2 |
| 6,685,841 B2 | 2/2004 | Lopez | 210/767 |
| 6,713,263 B2 | 3/2004 | Schwartz | 435/6 |
| 6,787,308 B2 | 9/2004 | Balasubramanian | |
| 6,812,005 B2 | 11/2004 | Fan | 435/91.2 |
| 6,828,100 B1 | 12/2004 | Ronaghi | 435/6 |
| 6,833,246 B2 | 12/2004 | Balasubramanian | 435/6 |
| 6,864,052 B1 | 3/2005 | Drmanac | 435/6 |
| 6,890,741 B2 | 5/2005 | Fan | 435/91.2 |
| 6,911,345 B2 | 6/2005 | Quake | 436/532 |
| 6,913,884 B2 | 7/2005 | Stuelpnagel | 435/6 |
| 6,998,228 B2 | 2/2006 | Henderson | 435/4 |
| 7,011,945 B2 | 3/2006 | Qiao | 435/6 |
| 7,049,074 B2 | 5/2006 | Schwartz | 435/6 |
| 7,064,197 B1 | 6/2006 | Rabbani | 536/24.3 |
| 7,189,503 B2 | 3/2007 | Akeson | 435/2 |
| 7,217,562 B2 | 5/2007 | Cao | 435/287.2 |
| 7,229,767 B2 | 6/2007 | Kmiec | 435/6 |
| 7,238,485 B2 | 7/2007 | Akeson | 435/6 |
| 7,244,559 B2 | 7/2007 | Rothberg | 435/6 |
| 7,258,838 B2 | 8/2007 | Li | 422/68.1 |
| 7,276,720 B2 | 10/2007 | Ulmer | 356/246 |
| 7,335,762 B2 | 2/2008 | Rothberg | 536/24.3 |
| 7,410,810 B2 | 8/2008 | Bohmann | 436/524 |
| 7,544,473 B2 | 6/2009 | Brennar | 435/6 |
| 2002/0004204 A1 | 1/2002 | O'Keefe | 435/6 |
| 2002/0055100 A1 | 5/2002 | Kawashima | 435/6 |
| 2002/0061533 A1* | 5/2002 | van Gemen | 435/6 |
| 2002/0197621 A1 | 12/2002 | Drmanac | 435/6 |
| 2003/0027201 A1 | 2/2003 | Schwartz | 435/6 |
| 2003/0124611 A1 | 7/2003 | Schwartz | 435/6 |
| 2003/0138941 A1* | 7/2003 | Gong et al. | 435/287.2 |
| 2004/0002090 A1 | 1/2004 | Mayer | 435/6 |
| 2004/0224336 A1* | 11/2004 | Wagner | 435/6 |
| 2004/0229221 A1 | 11/2004 | Schon | 435/6 |
| 2004/0248144 A1 | 12/2004 | Mir | 435/6 |
| 2005/0019776 A1 | 1/2005 | Callow | 435/6 |
| 2005/0037356 A1 | 2/2005 | Gullberg | 435/6 |
| 2005/0042649 A1 | 2/2005 | Balasubramanian | 435/6 |
| 2005/0100939 A1 | 5/2005 | Namsaraev | 435/6 |
| 2005/0191656 A1 | 9/2005 | Drmanac | 435/6 |
| 2005/0214840 A1 | 9/2005 | Chen | 435/6 |
| 2005/0244863 A1 | 11/2005 | Mir | 435/6 |
| 2006/0012784 A1 | 1/2006 | Ulmer | 356/246 |
| 2006/0012793 A1 | 1/2006 | Harris | 356/436 |
| 2006/0024681 A1 | 2/2006 | Smith | 435/6 |
| 2006/0088944 A1 | 4/2006 | Schwartz | 436/174 |
| 2007/0037152 A1 | 2/2007 | Drmanac | 435/6 |
| 2007/0072208 A1 | 3/2007 | Drmanac | 435/6 |
| 2007/0099208 A1 | 5/2007 | Drmanac et al. | 435/6 |
| 2007/0161028 A1 | 7/2007 | Schwartz | 435/6 |
| 2008/0102504 A1 | 5/2008 | Akeson | 435/173.2 |
| 2008/0171316 A1 | 7/2008 | Golovchenko | 435/6 |
| 2008/0213771 A1 | 9/2008 | Drmanac | 435/6 |
| 2008/0234136 A1 | 9/2008 | Drmanac | 506/3 |
| 2008/0248561 A1 | 10/2008 | Golovchenko | 435/287.2 |
| 2008/0318796 A1 | 12/2008 | Drmanac | 506/3 |
| 2009/0005252 A1 | 1/2009 | Drmanac | 506/3 |
| 2009/0005259 A1 | 1/2009 | Drmanac | 506/9 |
| 2009/0011416 A1 | 1/2009 | Drmanac | 435/6 |
| 2009/0011943 A1 | 1/2009 | Drmanac | 506/4 |
| 2009/0036316 A1 | 2/2009 | Drmanac | 506/4 |
| 2009/0099041 A1 | 4/2009 | Church | 506/26 |
| 2009/0118488 A1 | 5/2009 | Drmanac | 536/24.2 |
| 2009/0137404 A1 | 5/2009 | Drmanac | 506/3 |
| 2009/0143235 A1 | 6/2009 | Drmanac | 506/5 |
| 2009/0155781 A1 | 6/2009 | Drmanac | 435/6 |
| 2009/0264299 A1 | 10/2009 | Drmanac | 506/3 |

FOREIGN PATENT DOCUMENTS

| | | |
|---|---|---|
| WO | WO 95/10034 | 4/1995 |
| WO | WO 96/31522 | 4/1996 |
| WO | WO 98/42727 | 10/1998 |
| WO | WO 01/62982 | 8/2001 |
| WO | WO 2004/072294 | 8/2004 |
| WO | WO 2004/076683 | 9/2004 |
| WO | WO 2005/040425 | 5/2005 |
| WO | WO 2005/042763 | 5/2005 |
| WO | WO 2005/047523 | 5/2005 |
| WO | WO 2005/078130 | 8/2005 |
| WO | WO 2005/080605 | 9/2005 |
| WO | WO 2005/082098 | 9/2005 |
| WO | WO 2005/093094 | 10/2005 |
| WO | WO 2005/116262 | 12/2005 |
| WO | WO 2006/007207 | 1/2006 |
| WO | WO 2006/040549 | 4/2006 |
| WO | WO 2006/055521 | 5/2006 |
| WO | WO 2006/073504 | 7/2006 |
| WO | WO 2006/084132 | 8/2006 |
| WO | WO 2006/138257 | 12/2006 |
| WO | WO 2007/025124 | 3/2007 |
| WO | WO 2007/061425 | 5/2007 |
| WO | WO 2007/062160 | 5/2007 |

OTHER PUBLICATIONS

Chen et al, "A Homogeneous, Ligase-Mediated DNA Diagnostic Test", Genome Research, vol. 8, No. 5, May 1998, pp. 549-556.
Cowie et al, "Identification of APC gene mutations in colorectal cancer using universal microarray-based combinatorial sequencing-by-hybridization," Human Mutation, 24:261-271 (2004).
Li, M. et al., "BEAMing up for detection and quantification of rare sequence variants," Nature Methods, vol. 3, pp. 95-97 (2006).
Metzker, "Emerging Technologies in DNA Sequencing," Genome Research, 15: 1767-1776 (2005.
Shendure et al, "Accurate multiplex polony sequencing of an evolved bacterial genome," Science, 309: 1728-1732 (2005).
Shendure et al, "Advanced Sequencing Technologies: Methods and Goals," Nature Reviews Genetics, vol. 5, pp. 335-344 (2004).
Tringe et al, "Metagenomics: DNA Sequencing of Environmental Samples," Nature Reviews Genetics, vol. 6, pp. 805-814 (2005.
Vingron et al., "Sequence Alignment and Penalty Choice Review of Concepts, Case Studies and Implications," J. Mol. Biol, vol. 235, issue 1, pp. 1-12 (1994).
Branton et al., "The Potential Challenges of nanopore sequencing," Nature Biotechnology, v. 25, No. 10, p. 1146-1153, Oct. 2008.
Eisen et al., "A recombinase from *Drosophila melanogaster* embryos," Proc. Natl. Acad. Sci USA, 85(20), p. 7481-7485 (Oct. 1988).
Gaylord, et al., "DNA detection using water-soluble conjugated polymers and eptide nucleic acid probes," Proc. Natl. Acad. Sci., vol. 99, No. 17, p. 10954-10957, Aug. 20, 2002.
Halbrook at al., "Purification and Characterization of a DNA-pairing, and Strand Transtar Activity from Mitotic *Saccharomyces cerevisiae*," J. Biol. Chem. 264 (35), p. 21403 (1989).
Hsieh et al., "Formation of Joint DNA Molecules y Two Eukaryostic Strand Exchange Proteins Does Not Require Melting of a DNA Duplex," J. Biol. Chem. 264 (9), p. 5089, (Mar. 1989).

(56) References Cited

OTHER PUBLICATIONS

Kim et al., "Rapid fabrication of uniformly sized nanopores and nanopore arrays for parallel DNA analysis," Adv. Mater. V. 18, p. 3149-3153, 2006.

Kolodner et al., "Purification and characterization of an acitvity from *Saccharamyces cerevisiae* that catalyzes homologous pairing and strand exchange," Proc. Natl. Acad. Sci USA, 84 (16), p. 5560, (Aug. 1987).

Lavery et al., "Biochemical Basis of the Constitutive Repressor Cleavage Activity of recA730 Protein," J. Biol. Chem. 267 (29), p. 20648, (Oct. 1992).

Lee et al., "Rapid DNA sequencing by direct nanoscale reding of nucleotide bases on individual DNA chains," Perspectives in Bioanalysis, v. 2, p. 246-263.

Li, J. et al., "Enzymatic signal amplification of molecular beacons for sensitive DNA detection," Nucleic Acids Research, vol. 36, No. 6, 2008.

Lowenhaupt et al., "Drosophila melanogaster Strand Transferase: A Protein that Forms Heteroduplex DNA in the Absence of Both ATP and Single-Strand DNA Biding Protein,." J. Biol. Chem., 264 (34), p. 20568, (Dec. 1989).

Mediraju et al., "Properties of a mutant *recA*-encoded protein reveal a possible role for *Escherichia coli recF*-encoded protein in genetic recombination," Proc. natl. Acad. Sci USA, 85(18):6592 (Sep. 1988).

McCarthy et al., "Sensitive homologous recombination strand-transfer assay: Partial purification of a *Drosophila melahogester* enzyme and detection of sequence effects on the strand-transfer activity of RecA protein,"., Proc. Natl. Acad, Sci USA, 85: 5854 (Aug. 1988).

Moore et al., "Purification and Characterization of a Protein fromn Human Cells which Promotes Homologous Pairing of DNA," J. Biol. Chem., v. 265, No. 19, p. 11108 (Jul. 1990).

Moore et al., "The human homologous pairing protein HPP-1 is specifically stimulated by the cognate single-stranded bindig protein hRP-A," Proc. Natl. Acad. Sci USA, 88, p. 9067, (Oct. 1991).

Rothberg, et al., "The development and impact of 454 sequencing," Nature Biotechnology, vol. 26, No. 10, 1117-1124, Oct. 2008.

Sauer-Budge, et al., "Unzipping Kinetics of Double-Stranded DNA in a Nanopore," Physical Review Letters, v. 90, No. 23 (Jun. 13, 2003).

Shendure et al., "Next-generation DNA sequencing," Nature Biotechnology, vol. 26 No. 10, 1135-1144, Oct. 2008.

Soni, et al., "Progress toward ultrafast DNA sequencing using solid-state nanopores," Clinical Chemistry, vol. 53, no. p. 1996-2001, 2007.

Sugino et al., "ATP-independent DNA Strand Transfer Catalyzed by Protein(s) from Meiotic Cells of the Yeast *Saccharomyces Cerevisiae*"Proc. Natl. Acad. Sci USA, 85: 3683 (Jun. 1988).

\* cited by examiner

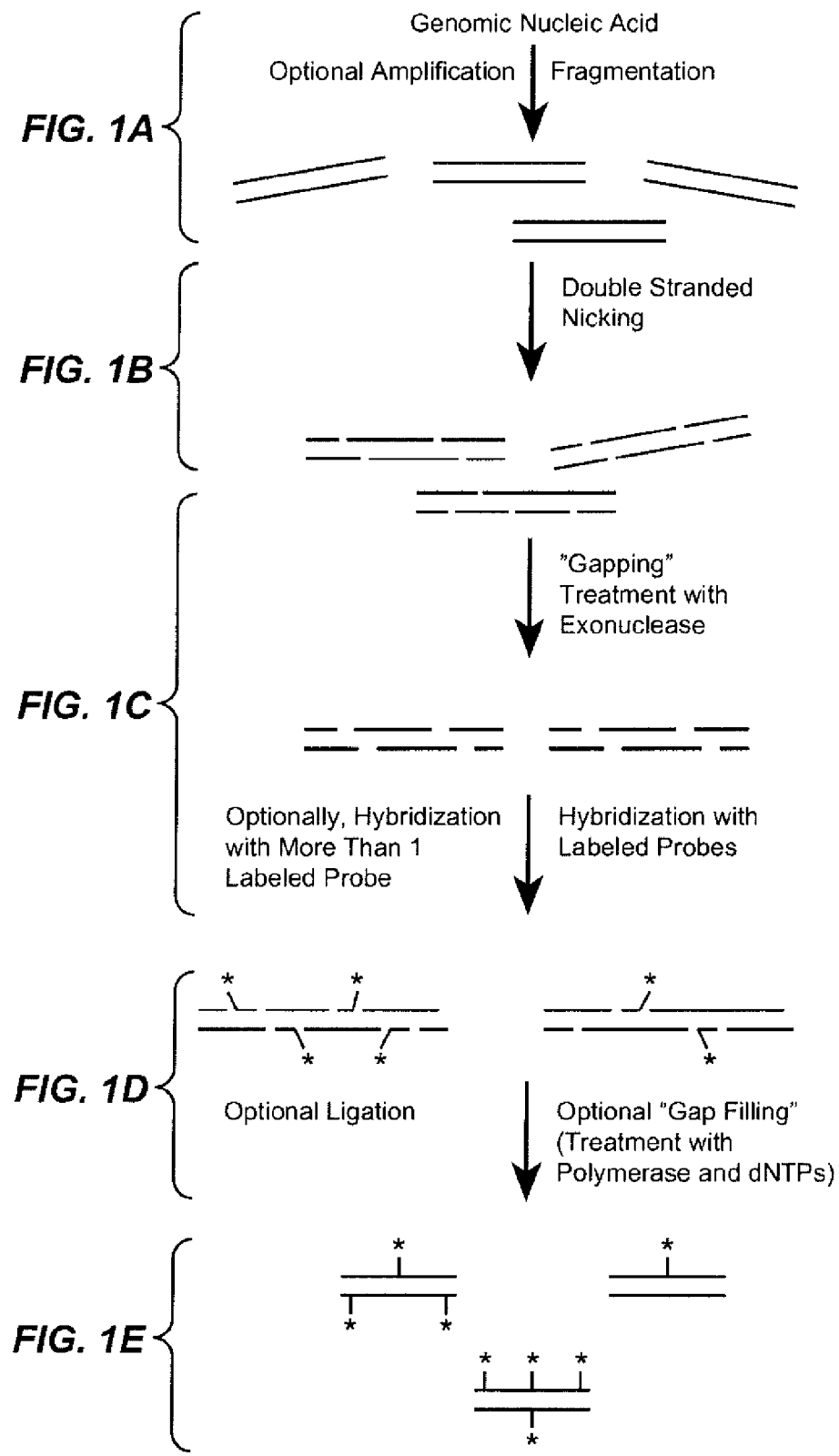

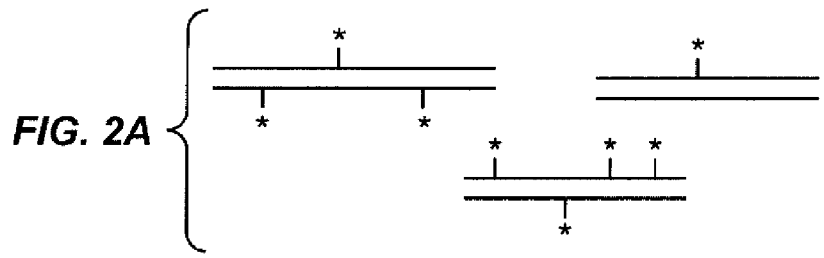
FIG. 2A
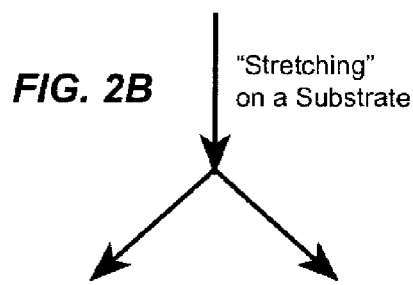
FIG. 2B "Stretching" on a Substrate
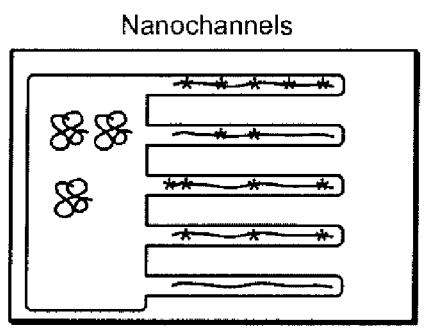
FIG. 2C
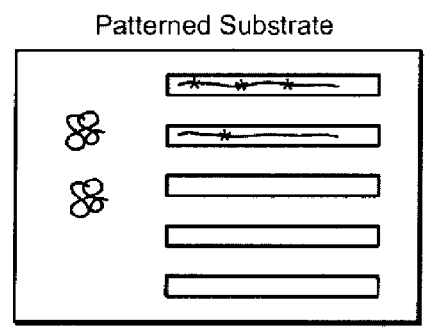
FIG. 2D
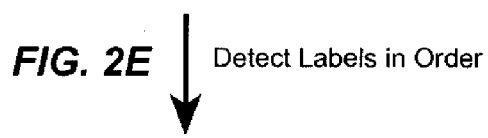
FIG. 2E Detect Labels in Order
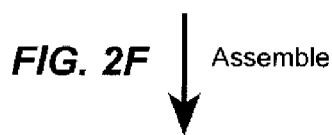
FIG. 2F Assemble

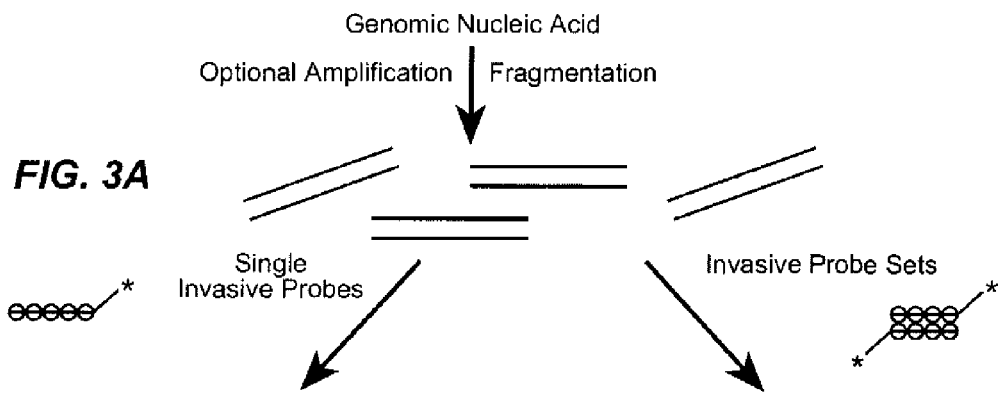
*FIG. 3A*
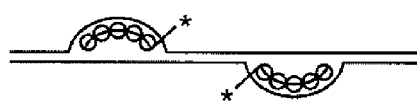
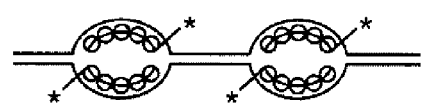
*FIG. 3B*        *FIG. 3C*
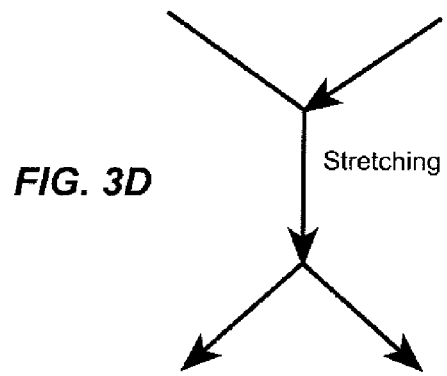
*FIG. 3D*
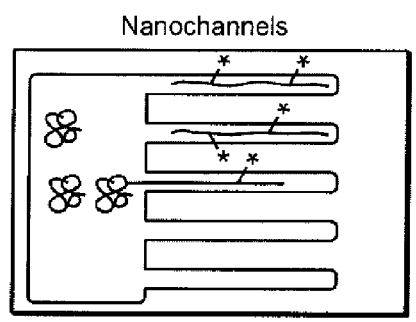
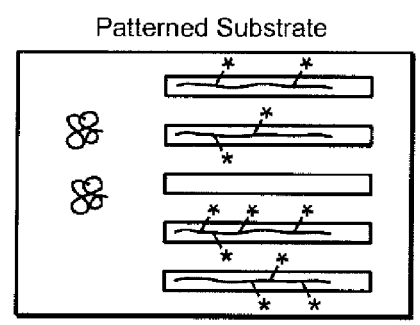
*FIG. 3E*        *FIG. 3F*

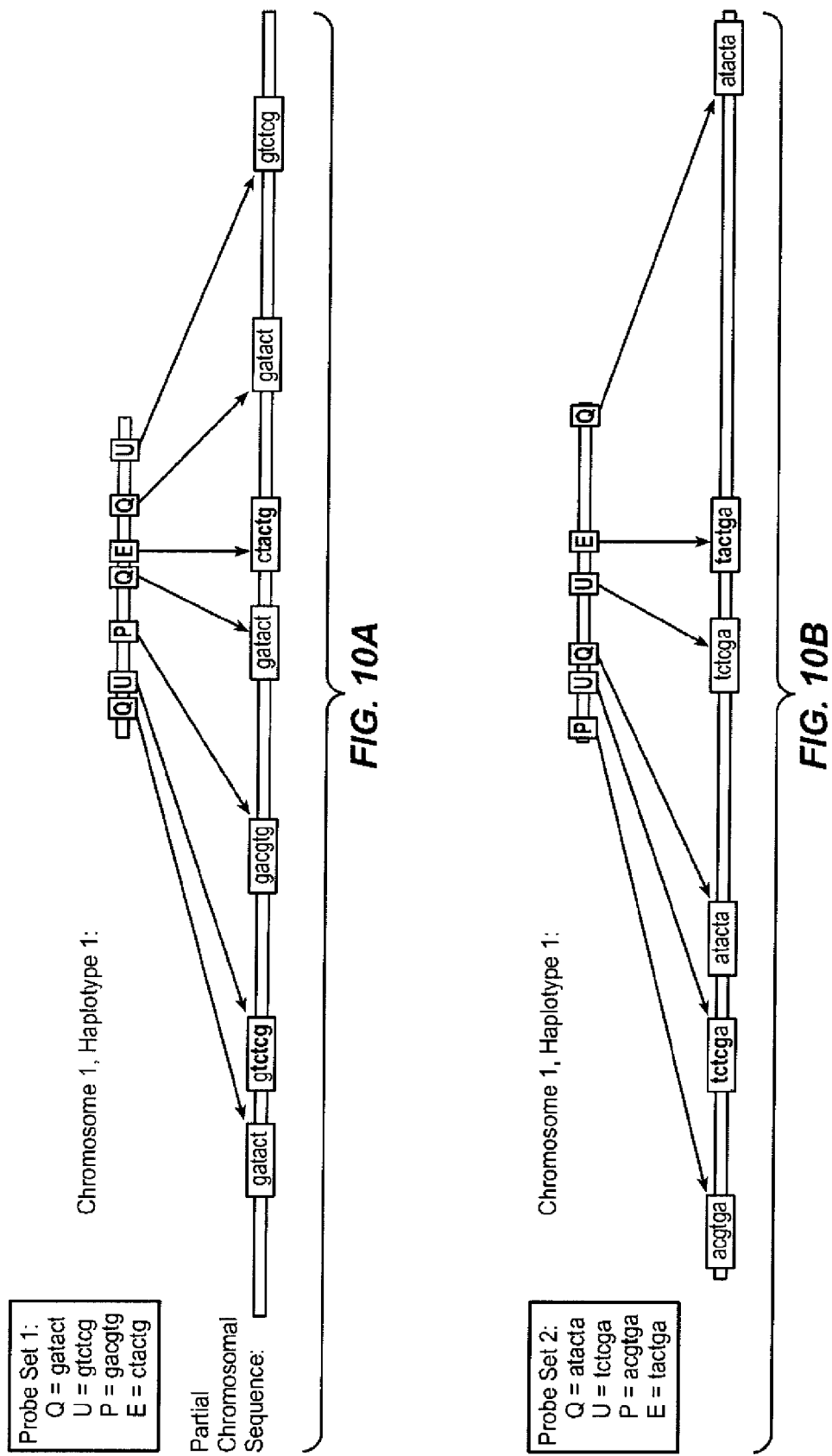

SEQUENCE ANALYSIS USING DECORATED NUCLEIC ACIDS

CROSS REFERENCE TO RELATED APPLICATIONS

This application claims the benefit of priority to U.S. Provisional Patent Application Nos. 60/980,132, filed Oct. 15, 2007; 60/980,306, filed Oct. 16, 2007; 60/980,711, filed Oct. 17, 2007 and 60/981,046, filed Oct. 18, 2007, each of which is hereby incorporated by reference in its entirety.

STATEMENT OF FEDERALLY SPONSORED RESEARCH

This invention was supported at least in part by a grant from the National Institute of Standards and Technology, grant number 70NANB7H7027N. The U.S. government may have some rights in this invention.

BACKGROUND OF THE INVENTION

Large-scale sequence analysis of genomic DNA is central to understanding biological phenomena in humans and in many economically important plants and animals. Sequence analysis of whole genomes, particularly analysis of the three billion base pairs in the human genome, involves a level of complexity that is compounded by the requirement for accuracy and speed for applications related to applications such as clinical diagnostics. In general, 60 billion or more sequence data points must be analyzed to provide an accurate genome sequence read.

Early sequencing methods generated sequence data from thousands of isolated, very long fragments of DNA to preserve the contextual integrity of the sequence information and reduce the need for redundant testing to obtain accurate results. However, such methods cost hundreds of millions of dollars per genome due to the complexity of preparing the genome fragments and the relatively high cost of the individual biochemistry tests used to generate sequence data from those fragments.

Advancements in fixed array technologies reduced the complexity of the preparation of the genomic fragments by providing the means to fragment a genome into millions of short pieces and computationally weave the genome sequence though deep redundant sequence analysis. Such advancements reduced the cost of genome sequencing from hundreds of millions to hundreds of thousands of dollars. However, these array technologies can be limited in applicability, because they are not able to provide contextual information, particularly the contextual information inherent in the fact that there are two distinct copies of the genome in each human cell. Accurate sequence analysis, particularly for clinical analysis and diagnosis, requires the ability to distinguish sequence differences between the two unique copies of the three billion DNA bases interspersed with millions of inherited single nucleotide polymorphisms, hundreds of thousands of short insertions and deletions, as well as hundreds of spontaneous mutations. Many methods for applying long read strategies to single molecules that could provide this contextual information are not compatible with the processivity scale up required to ensure accurate sequencing in clinically relevant time frames and at a clinically amenable cost. In addition, many conventional sequencing techniques are not effective in the analysis of arrays of single molecules, because the signal associated with single molecules are often not intense enough to overcome noise inherent in such systems. A cost-effective and highly accurate sequencing technology that provides the ability to read long single nucleic acid molecules is therefore desirable.

SUMMARY OF THE INVENTION

Accordingly, the present invention provides a sequence interrogation chemistry that combines the accuracy and haplotype integrity of long-read sequencing with improved methods of preparing genomic nucleic acids and analyzing sequence information generated from those nucleic acids.

In one aspect, the present invention provides a composition that comprises a substrate comprising a plurality of locations. Each location of the substrate comprises a single molecule of stretched decorated nucleic acids. Each of the stretched nucleic acids comprises a plurality of probes, and the stretched decorated nucleic acids are positioned on the substrate in such a way that they are optically resolvable.

In a further aspect, stretched decorated nucleic acids of the invention are formed by: (i) nicking a nucleic acid to form a nicked nucleic acid, (ii) adding an exonuclease to the nicked nucleic acid to form a gapped nucleic acid, and (iii) adding a first set of labeled probes to the gapped nucleic acid such that at least one of the first set of labeled probes hybridizes to single stranded areas of said gapped nucleic acid. In a further embodiment, the first set of probes comprises a plurality of non-overlapping probe sequences. In a still further embodiment, each probe sequence comprises a unique label. In exemplary embodiments, steps (i) through (iii) are performed simultaneously or are performed sequentially.

In a further aspect, stretched decorated nucleic acids of the invention are formed by (i) providing a double stranded nucleic acid; (ii) adding a first set of recA invasive labeled probes to the double stranded nucleic acid to form D-loops within the double stranded nucleic acid, thus forming a decorated nucleic acid; and (iii) stretching the decorated nucleic acid to form a stretched decorated nucleic acid. In this aspect of the invention, the recA invasive labeled probes comprise a plurality of non-overlapping probe sequence and each probe sequence comprises a unique label. Such probes hybridize to sequences in the double stranded nucleic acid that are complementary to the probe sequences.

In a still further aspect, the present invention provides methods for detecting the presence of a target nucleic acid in a sample. In this aspect, a substrate comprising stretched decorated nucleic acids of the invention is provided. As described herein, the stretched decorated nucleic acids of the invention will generally comprise a plurality of labeled probes. The order of the labeled probes on the stretched decorated nucleic is determined, and that order thereby indicates the presence of the target nucleic acid.

In a further aspect, stretched decorated nucleic acids of the invention are used to obtain sequence information from a target nucleic acid. In this aspect, a substrate comprising stretched decorated nucleic acids of the invention is provided. As described herein, the stretched decorated nucleic acids of the invention will generally comprise a plurality of labeled probes. The order of the labeled probes on the stretched decorated nucleic is determined, and that order thereby provides sequence information for the target nucleic acid.

BRIEF DESCRIPTION OF THE DRAWINGS

FIG. 1 is a schematic illustration of an exemplary embodiment of the invention for decorating nucleic acids. Genomic nucleic acid is fragmented and optionally amplified to produce the fragments illustrated in FIG. 1A. These fragments are nicked with a nicking enzyme in FIG. 1B and then gaps are formed at one or more of those nicks through treatment with an exonuclease to produce the gapped nucleic acids pictured in FIG. 1C. Labeled probes, either a single probe or different probes, are hybridized to the gapped nucleic acids to form the decorated nucleic acids in FIG. 1D. The decorated nucleic acids may then optionally be repaired by filling in the gaps by treatment with a polymerase and nucleotides and/or optionally by treatment with ligase to produce the decorated nucleic acids in FIG. 1E.

FIG. 2 is a schematic illustration of an exemplary embodiment of the invention in which decorated nucleic acids (FIG. 2A) are stretched on a substrate in FIG. 2B. The substrate can comprise nanochannels (FIG. 2C) or a patterned substrate comprising linear features (FIG. 2D). In further embodiments, the order of labels can be detected (FIG. 2E) and then assembled to generate a whole or partial sequence (FIG. 2F) of a target nucleic acid (such as a chromosome).

FIG. 3 is a schematic illustration of an exemplary embodiment for forming decorated nucleic acids and stretching them on a substrate. Genomic nucleic acid is fragmented and optionally amplified to form double stranded fragments (FIG. 3A). Invasive probes, either single invasive probes (FIG. 3B) or invasive probe sets (FIG. 3C) are applied to form D-loops (FIG. 3B) or double D-loops (FIG. 3C). The decorated nucleic acids are stretched on substrates comprising nanochannels (FIG. 3E) or on a patterned substrate comprising linear features (FIG. 3F). In an optional embodiment, prior to stretching in FIG. 3D, the invasive probes within the D-loops or double D-loops are extended using a polymerase to further stabilize the structure of the decorated nucleic acid and prevent the D-loop or double D-loop from destabilizing the probes and causing them to detach from the nucleic acids.

FIGS. 4A-E are schematic illustrations of different configurations in which two labeled probes can hybridize to the same gap.

DETAILED DESCRIPTION OF THE INVENTION

Figure 4A:

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

I. Overview

The present invention is directed to compositions and methods for single molecule nucleic acid identification and detection, which finds use in a wide variety of applications as described herein. Generally, the invention can be described as follows. Genomic nucleic acid, generally double stranded DNA, is obtained from cells, generally from roughly 10 to 100 cells. The genomic nucleic acid is fractionated into appropriate sizes using standard techniques such as physical or enzymatic fractionation. Amplification can optionally be done as needed, although in general, the efficiency and redundancy of the present invention allows the methods to be done without amplification.

The genomic nucleic acid fragments are then "decorated" with labeled probes in one of two ways. In one embodiment, the fragments are nicked using nicking enzymes, and "gapped", using exonucleases, to produce single stranded gaps spaced along both strands of the double stranded target, as is generally shown in FIGS. 1 and 2. Labeled probes are then added under conditions such that if the label probes are perfectly complementary to the single stranded nucleic acid of the gap, the label probe hybridizes to the single strand. This forms a "decorated" target nucleic acid. Optionally, polymerase and dNTPs can be added to "fill in the gaps", and further optionally ligase can be added to ligate one or both ends of the probes to the rest of the target sequence. Thus, as discussed below, a decorated nucleic acid can still contain gaps and/or nicks, depending on the configuration of the system used as well as stretching conditions; for example, vigorous stretching conditions may favor the use of decorated nucleic acids with a minimum of gaps and/or nicks, while other stretching techniques may not require the use of any filling or ligation.

Another embodiment used to create decorated nucleic acids does not rely on the use of nicking and gapping techniques to decorate the nucleic acids. In this embodiment, as depicted in FIG. 3, invasive probes are used, e.g. recA probes are used. RecA is a protein that binds to single stranded probes and then will hybridize to a corresponding sequence in a target double stranded sequence, forming a "bubble" or a "D-loop" as it is frequently referred to. The recA probes of the invention are also labeled as outlined herein. In some embodiments, pairs of recA probes can be made, such that the probes hybridize to each strand, forming "double D-loops", again as generally depicted in FIG. 3C. That is, a "Watson" recA labeled probe and a "Crick" recA labeled probe are used, preferably labeled with the same label, to deliver two labels to the target. The incorporation of the recA probes along the target sequence also forms a "decorated" nucleic acid.

As is more fully discussed herein, the label probes can take on a wide variety of configurations. In some embodiments, the label probes are single stranded and contain a distinguishing label for each label probe sequence; this can be done for both the nicking and recA embodiments. In some embodiments, the label probes contain more than one label, such as depicted in FIG. 5, which shows a hybridization complex of several sequences that contain more than one label without significant quenching. In some embodiments, two label probes are used, which can be optionally ligated together, and may contain FRET pairs, which allows longer sequence calls. In addition, the label probes may be labeled at either terminus or at an internal position, which can determine whether the label probes can be ligated at one or both ends during the decoration process.

The decorated nucleic acid is then "stretched". In general, this refers to the process of adding a decorated nucleic acid to a substrate in such a manner that the decorated nucleic acid is substantially linear and optically separated from other single decorated nucleic acids; that is, the order (and in some cases, the spacing) of the labels can be determined. As will be appreciated by those in the art, the stretched nucleic acid need not be perfectly linear, it just needs to be "straight" enough such that a non-ambiguous order of labels can be determined. For example, having the decorated nucleic acid stretched in a straight or serpentine channel is sufficient.

After stretching, a detector is used to determine the order of the labels within the decorated nucleic acid, and, in some cases, some determination of distance between the labels, depending on the system. The information is then used to create a map, or "sequence signature", as is generally depicted in FIG. 9D. This sequence signature can be compared against a reference sequence, or database of sequences, to determine any number of things, including for example the identity of the genome (e.g. pathogens). That is, each fragment will have a readout of colors in a particular order, with each color corresponding to a particular sequence. As a very simplistic example, fragment 1 may be red-red-yellow-green-green-blue-yellow-yellow-yellow-red, fragment 2 may be yellow-green-green-blue-red-yellow-blue-red-red-yellow-green, and fragment 3 may be yellow-yellow-red-green-blue-blue-blue-yellow-red-green. Lining these up using the overlaps gives an order of fragment 2-fragment 1-fragment 3. Using the sequences of the probes, this generates a "sequence signature" that can be compared to reference sequences to identify the nucleic acid, or to confirm its identity. In addition, to the extent that the detector allows some distance determination (e.g. fragment 1 is red-red within 500 basepairs-yellow within 2000 basepairs-green within 500 basepairs etc.), this information can be used as well.

In addition, the match of sequence to a reference that contains some differences, e.g. one of the sequences of the probe is not present, can also be used to identify changes in the target genome, e.g. a single nucleotide polymorphism (SNP) within a probe sequence (e.g. fragment 1 in this particular sample is missing the second red, although the rest of the signature is correct, indicating a change within that sequence of that particular target)

II. Compositions of the Invention

The present invention provides compositions comprising substrates with stretched decorated nucleic acids. As discussed further below, the stretched decorated nucleic acids of the invention can be used for a variety of purposes, including sequence analysis, analysis of genetic variation, detection of pathogens and detection of markers for disease.

IIA. Target Nucleic Acids

The present invention provides compositions and methods utilizing stretched, decorated nucleic acids to identify and/or detect target nucleic acids in samples. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples (i.e. in the case of nucleic acids, the sample may be the products of an amplification reaction, including both target and signal amplification as is generally described in PCT/US99/01705, such as PCR amplification reaction); purified samples, such as purified genomic DNA, RNA, proteins, etc.; raw samples (bacteria, virus, genomic DNA, etc.); as will be appreciated by those in the art, virtually any experimental manipulation may have been done on the sample. In one aspect, stretched decorated nucleic acids are formed from genomic DNA. In an exemplary embodiment, genomic DNA is isolated from a target organism. By "target organism" is meant an organism of interest and as will be appreciated, this term encompasses any organism from which nucleic acids can be obtained. Methods of obtaining nucleic acids from target organisms are well known in the art. Samples comprising genomic DNA of humans find particular use in many embodiments.

In general, a target nucleic acid is used to generate stretched decorated nucleic acids of the invention. The term "target nucleic acid" refers to a nucleic acid of interest. In one aspect, target nucleic acids of the invention are genomic nucleic acids. Target nucleic acids include naturally occurring or genetically altered or synthetically prepared nucleic acids (such as genomic DNA from a mammalian disease model). Target nucleic acids can be obtained from virtually any source and can be prepared using methods known in the art. For example, target nucleic acids can be directly isolated without amplification, isolated by amplification using methods known in the art, including without limitation polymerase chain reaction (PCR), multiple displacement amplification (MDA), rolling circle amplification (RCA), rolling circle amplification (RCR) and other amplification methodologies. Target nucleic acids may also be obtained through cloning, including cloning into vehicles such as plasmids, yeast, and bacterial artificial chromosomes.

By "nucleic acid" or "oligonucleotide" or "polynucleotide" or grammatical equivalents herein means at least two nucleotides covalently linked together. A nucleic acid of the present invention will generally contain phosphodiester bonds, although in some cases, as outlined below (for example in the construction of primers and probes such as label probes), nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120:13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" (LNA™) are also included within the definition of nucleic acid analogs. LNAs are a class of nucleic acid analogues in which the ribose ring is "locked" by a methylene bridge connecting the 2'-O atom with the 4'-C atom, All of these references are hereby expressly incorporated by reference. These modifications of the ribose-phosphate backbone may be done to increase the stability and half-life of such molecules in physiological environments. For example, PNA:DNA and LNA-DNA hybrids can exhibit higher stability and thus may be used in some embodiments.

The target nucleic acids may be single stranded or double stranded, as specified, or contain portions of both double stranded or single stranded sequence. Depending on the application, the nucleic acids may be DNA (including genomic and cDNA), RNA (including mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As outlined below, many embodiments utilize substantially double stranded genomic DNA as the target nucleic acids.

The term "nucleic acid" includes oligonucleotides and polynucleotides. Decorated nucleic acids of the invention can in some embodiments be at least 10 kb in length. In further embodiments, decorated nucleic acids of the invention are at least 20, 30, 40, 50, 60, 70, 80, 90, 100, 120, 140, 160, 180, 200, 250, 300, 350, 400, 450, 500, 750, and 1000 kb in length. In some embodiments, for example in the sequencing of cDNA/mRNA molecules, the decorated nucleic acids can be shorter depending on the length of the gene, e.g. 1-10 kb in length.

IIB. Substrates

As outlined herein, the compositions of the invention comprise decorated target nucleic acids, generally stretched on a substrate. By "substrate" or "solid support" or other grammatical equivalents herein is meant any material that is modified to allow "stretching" of nucleic acid molecules as described herein. In general, the substrate contains discrete individual sites (for example, nanochannels or lines) appropriate for the attachment or association of decorated nucleic acid molecules to form stretched nucleic acids and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresces.

Substrates of the invention can be configured to have any convenient geometry or combination of structural features. The substrates can be either rigid or flexible and can be either optically transparent or optically opaque, or have combinations of these surfaces. The substrates can also be electrical insulators, conductors or semiconductors. Further the substrates can be substantially impermeable to liquids, vapors and/or gases or, alternatively, the substrates can be substantially permeable to one or more of these classes of materials.

In general, the substrates fall into two different classes: substrates comprising particular geometries such as nanochannels or nanopores, as more fully discussed below, or those that have surface characteristics to allow the stretching of decorated nucleic acids, such as the use of linear patterns of surface chemistries.

In one aspect of the invention, substrates of the invention comprise nanostructures. Such structures can include without limitation nanopillars, nanopores and nanochannels.

In many exemplary aspects, substrates of the invention comprise nanochannels. Such substrates are known in the art. For example, U.S. Pat. Nos. 7,217,562; 6,685,841; 6,518,189; 6,440,662; 6,214,246 describe nanostructures, including nanochannels, of use in accordance with the present invention. These patents are hereby incorporated by reference in their entirety for all purposes and in particular for their teachings regarding the figures, legends and accompanying text describing the compositions, methods of using the compositions and methods of making the compositions.

Generally, in these nanochannel substrates, there is a reservoir into which the decorated nucleic acids are placed, which are then moved into nanochannels, a single molecule of decorated nucleic acid per nanochannel, to form the stretched nucleic acids, followed by detection of the order, and optionally, the distance between the labels of the incorporated probes.

Additional nanochannel systems have also been described in PCT Publication Nos. WO9510034, WO9631522, U.S. Publication Nos. 20030124611, 20030027201, 20060088944, 20070161028, and U.S. Pat. Nos. 6,713,263; 6,610,256; 6,509,158; 6,448,012; 6,294,136; 6,150,089; 6,147,198; 5,720,928; 5,559,664; 5,405,519; 5,720,928 and 7,049,074, all of which are incorporated by reference in their entirety and in particular for the figures, legends and accompanying text describing the compositions, methods of using the compositions and methods of making the compositions.

In many embodiments, the substrates comprise nanochannels that are generally from about 10 nanometers to about 50 nanometers in diameter.

Another embodiment of nanostructures that finds use in the present invention are substrates comprising nanopores. Nanopore devices can provide single-molecule detection of molecules driven electrophoretically in solution through a nanoscale pore, and the sequence of nucleotides can be detected by the sequence of signals generated as each nucleotide passes through the pore. Such nanopores and methods of sequencing using nanopores are known in the art and discussed in for example, Branton et al., (2008), *Nature,* 26(10):1146-53 and in U.S. Pat. Nos. 6,673,615; 7,258,838; 7,238,485; 7,189,503; 6,627,067; 6,464,842; 6,267,872 and U.S. Patent Application Nos. 20080248561; 20080171316, 20080102504, each of which is herein incorporated by reference in its entirety for all purposes, and in particular for the figures, legends and accompanying text describing the compositions, methods of using the compositions and methods of making the compositions.

In addition to the use of substrates comprising nanostructures, substrates comprising essentially linear patterns of surface characteristics, e.g. hydrophilicity, can be used to as the compositions of the stretched nucleic acids of the invention. In this embodiment, substrates of the invention will generally comprise discrete individual sites for attachment or association of a stretched decorated nucleic acid molecules of the invention. Such sites may be a pattern, i.e. a regular design or configuration, or randomly distributed. "Pattern" in this sense includes a repeating unit cell, preferably one that allows a high density of nucleic acid molecules on the substrate. In such an embodiment, the surface of the substrate is modified to allow attachment of the nucleic acid molecules at individual sites, whether or not those sites are contiguous or non-contiguous with other sites, although in many embodiments the sites are optically resolvable. Thus, the surface of the substrate may be modified such that discrete sites are formed that can only have a single associated nucleic acid.

Figure 13:
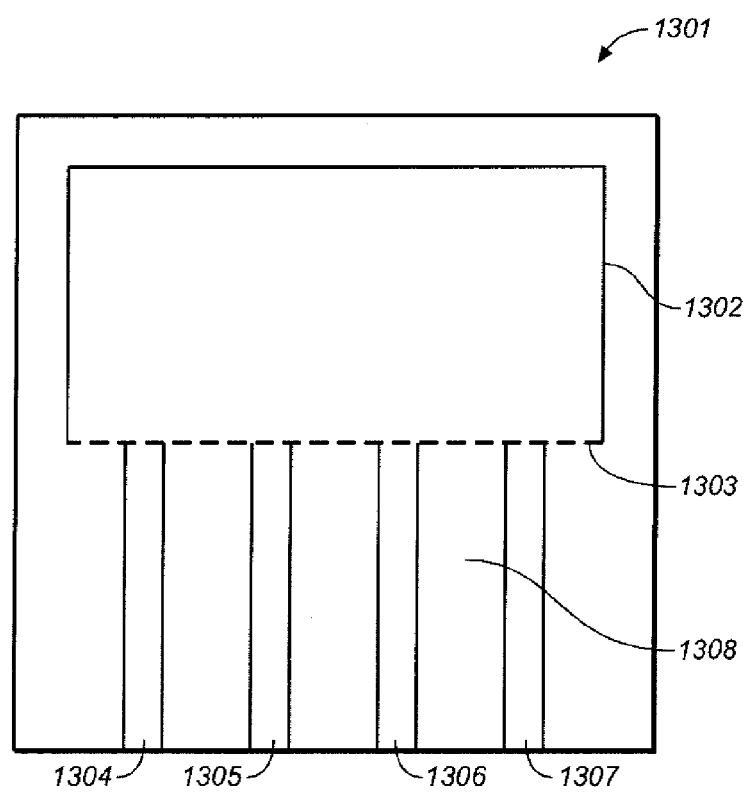
FIG. 13 is a schematic illustration of a substrate of use in the invention. The exemplary substrate illustrated comprises a non-patterned region that leads into linear features.

Such substrates have a number of advantages, including ease of preparation and the ability to produce a complete array of longer stretched nucleic acid molecules. An exemplary embodiment of such substrates is illustrated in FIG. 13 (which are also referred to herein as "flowthrough substrates" and "flowthrough systems"). As shown in FIG. 13, the substrate 1301 comprises a non-patterned region 1302 that leads into a region patterned with linear features (1304-1307), which are interspersed with non-binding regions such as 1308. Nucleic acid molecules can be flowed across the non-patterned region 1302 into the linear features 1304-1307. The flow across the open region 1302 will generally result in allowing the nucleic acid molecules to "untangle" and stretch as they are moved along with the flow toward the linear features. 1303 is an interface region between the non-patterned region 1302 and the linear features. This interface region may comprise patterns that conform to or lead into the linear features or the interface region may be non-patterned.

The linear features of such substrates can be long and very narrow. In one embodiment, such linear features are about 10 nm to about 1 µm in width. In a further embodiment, such linear features are about 10 to about 100 nm in width. In a still further embodiment, such linear features are about 20 to about 750, about 30 to about 500, about 40 to about 400, about 50 to about 300, about 60 to about 200, and about 70 to about 100 nm in width. In a further embodiment, the linear features are about 10 µm to about 5 mm in length. In a still further embodiment, the linear features are about 100 µm to about 1 mm in length. In a still further embodiment, the linear features are about 20 to about 900, about 30 to about 800, about 40 to about 700, about 50 to about 600, about 60 to about 500, about 70 to about 400, about 80 to about 300, about 90 to about 200, and about 100 to about 150 µm in length. As will be appreciated by those in the art, a wide variety of lengths and widths can be used depending on the system and length of the target sequences.

In a further embodiment, the linear features are separated by regions of the substrate surface that do not bind and/or repel nucleic acids. In an exemplary embodiment, the linear features are separated by about 30-3000 nm. In a further embodiment, the linear feature are separated by about 40 to about 2500, by about 50 to about 2000, by about 60 to about 1500, by about 70 to about 1000, by about 80 to about 900, by about 90 to about 800, by about 100 to about 700, by about 200 to about 600, by about 300 to about 500, and by about 400 to about 450 nm. In general, what is important is that the distance between the stripes is great enough to avoid significant cross-binding, that is, one target nucleic acid binding to more than one stripe. Thus, the distance between the features can also vary depending on the length of the sequence. For example, in the sequencing of "shorter" targets, e.g. cDNAs, the features can be closer together.

In a further embodiment, the linear features comprise positive charges that are able to attract and bind nucleic acid molecules. Optionally, these areas are separated by negative charges and/or hydrophobic chemistries. This can be accomplished using a wide variety of known techniques as is more fully discussed below.

Each linear feature may comprise one or multiple consecutive stretched decorated nucleic acid molecules.

In a still further embodiment, a substrate of the invention may comprise over 100, 1000, 10,000, 100,000 or 1,000,000 linear features. All or a portion of such linear features may further comprise one or more stretched decorated nucleic acid molecules.

In these embodiments, the nature of the patterned linear features will depend on the material of the substrate and the desired characteristics. For example, in one embodiment, patterns on the substrate are generated using surfaces chemistries that result in a pattern of hydrophilic surface area (e.g. a line or stripe), optionally surrounded or separated by hydrophobic areas. Alternate embodiments utilize electrostatic forces, for example linear stripes of positively charged surface chemistries, again optionally surrounded or separated by either positively charged or neutral surface chemistries The open non-patterned region of the substrate will generally not bind or otherwise attract nucleic acids, and in some embodiments, this non-patterned region will be negatively charged and/or hydrophobic. The length of this non-patterned region can be adjusted to accommodate nucleic acid type (single stranded or double stranded, RNA, DNA, etc.), nucleic acid length, and loading conditions.

In an exemplary embodiment substrates such as those illustrated in FIG. 13 are enclosed in a flow cell. In a further exemplary embodiment, such substrates are enclosed in a chamber or covered by a material (such as, in one non-limiting example, a glass coverslip) to create a space of about 10 nm to about 1 µm in the "z" dimension, allowing solutions containing decorated nucleic acids to flow across the non-patterned region to the linear features. This movement of the decorated nucleic acids may be due to any number of forces, including gravity, an electric field, or some combination thereof. In general, as the nucleic acids flow across the non-patterned surface to the linear features, the nucleic acids will become stretched and oriented in the direction of the linear features. As the nucleic acids flow across and are attracted and/or bind to the linear features, they may be further stretched. In an exemplary embodiment, one end of the nucleic acid molecules may be designed to move faster across the surface or attach/adsorb to the linear feature before the other end. The nucleic acid molecule, as it moves along with the flow of the solution, will be further strip until the majority of its length is attached or otherwise associated with some or all of the remaining length of the linear feature.

In a further embodiment, the height ("z direction") of the non-patterned region is different than that of the region comprising the linear features. Such differential heights can be designed to help direct the nucleic acid molecules across the non-patterned area of the substrate toward the area comprising the linear features.

Loading of nucleic acids onto these substrates can be modulated and/or controlled by the flow and/or electrical forces, including diffusion forces and surface forces exerted by areas of differential charge and/or hydrophobicity. The number of nucleic acids applied to the substrate (i.e., with a loading buffer or other solution) can be adjusted to assure maximal occupancy of the linear features with non-overlapping nucleic acid molecules and thus minimize the number of empty linear features on the substrate. In an exemplary embodiment, at least 50% of the linear features of a substrate are occupied by at least one nucleic acid molecule. In a further embodiment, at least 60%, 70%, 80%, 90%, and 95% of the linear features are occupied by one or more nucleic acids.

In some embodiments, a nucleic acid occupying a linear feature will exclude the entrance of a second nucleic acid to that same linear feature, for example by the repelling force of the negative charge of the first nucleic acid molecule alone, or in combination with the attractive force of positive charges contained in nearby empty linear features. This exclusion may be further controlled and/or modulated by the rate of flow of the nucleic acid molecule-containing solution through and/or across the substrate, by the dimensions of the linear features and the non-patterned region (particularly the height of these regions), the buffer composition, the width of the linear features, as well as other parameters apparent to one of skill in the art.

In some embodiments, nucleic acids not adsorbed, attached or otherwise associated with a linear feature will be washed away or otherwise removed from the substrate before the substrate comprising the nucleic acids are used in applications, such as sequencing applications, as discussed further herein.

In further embodiments, nucleic acid molecules may be continuously flowed through and/or over and/or across linear features, allowing for continuous detection and analysis of each decorated nucleic acid molecule as it travels along the linear features.

In embodiments of the invention, photolithography, electron beam lithography, nano imprint lithography, and nano printing may be used to generate such patterns on a wide variety of surfaces, e.g. Pirrung et al, U.S. Pat. No. 5,143,854; Fodor et al, U.S. Pat. No. 5,774,305; Guo, (2004) Journal of Physics D: Applied Physics, 37: R123-141; which are incorporated herein by reference for all purposes, and in particular for the figures, legends and accompanying text describing the compositions, methods of using the compositions and methods of making the compositions.

These techniques can be used to generate patterns of features on the order of $1/10^{th}$ of a micron and have been developed for use in the semiconductor industry. In one exemplary embodiment, a single "masking" operation is performed on a substrate of use in the present invention, as opposed to the 20 to 30 masking operations typically needed to create even a simple semiconductor. Using a single masking operation eliminates the need for the accurate alignment of many masks to the same substrate. There is also no need for doping of materials. Minor defects in the pattern may have little to no effect on the usability of the array, thus allowing production yields to approach 100%.

In one embodiment, "stamps" are made containing the desired pattern of features, which can then be dipped into the appropriate chemistries and stamped onto the surfaces; see for example U.S. Patent Applications 20070275193 and 20070264481, and Zhou et al., SID 08 Digest 37.3, p 534 (2008), all of which are incorporated by reference in their entirety as well as the references cited within.

In one aspect, substrates of the invention comprise silicon dioxide wafers. Such silicon dioxide wafers may in one embodiment be patterned in accordance with methods described above and known in the art.

In one aspect of the invention, substrates comprise a plurality of locations. Such locations may be patterned on the surface using methods described above. In an exemplary embodiment, each of the locations on the substrate comprises a single stretched decorated nucleic acid. In a further exemplary embodiment, the stretched decorated nucleic acids are positioned on the substrate such that they are optically resolvable. Each of the plurality of locations may comprise a nanochannel or a surface comprising hydrophobic regions alternating with hydrophilic regions, as discussed further above.

In some embodiments, substrates of the invention comprise a plurality of locations, but these locations do not comprise capture probes; that is, the substrate does not contain attached nucleic acids used to capture targets, as is well known in the art.

In some embodiments, the substrates may be part of a cartridge system, (sometimes referred to as a "biochip"), that can include a variety of different additional components for functionality, including pumps, valves, reagents, additional chambers (in addition to the detection chamber), etc. Such features as well as others are known in the art and encompassed by the present invention.

IIC. Stretched Nucleic Acids

Figure 14:
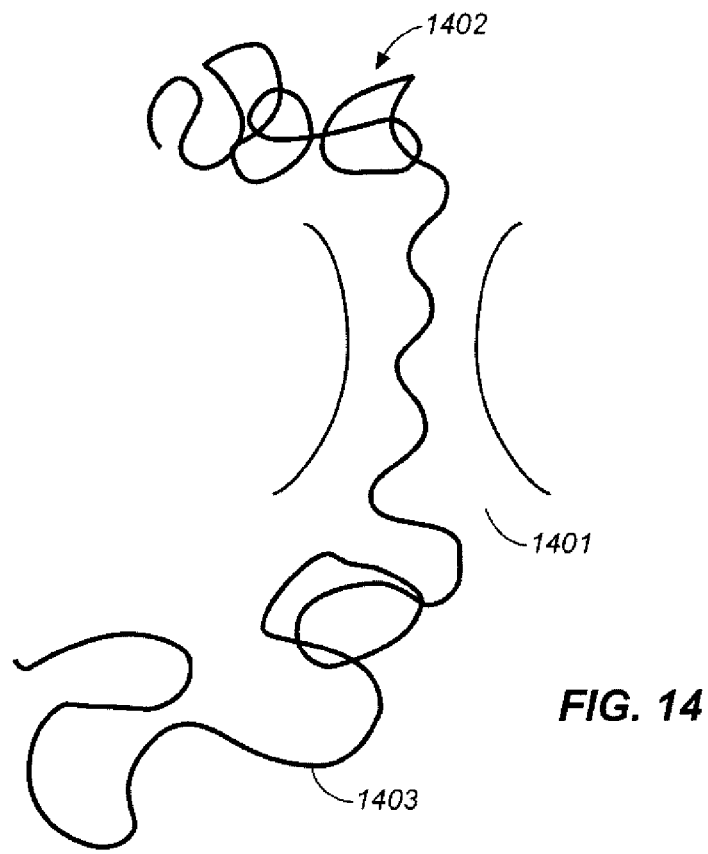
FIG. 14 is a schematic illustration of a substrate of use in the invention that comprises a nanopore. A nucleic acid molecule can be non-linear (i.e., non-stretched) on either side of the nanopore, but the movement through the nanopore serves to stretch the nucleic acid.

As provided herein, the present invention encompasses compositions comprising substrates with stretched decorated nucleic acids. By "stretched" is meant linearized such that the order and optionally the relative distance of probes along the decorated nucleic acids can be detected. Such stretched nucleic acids may be of any configuration such that order and optionally relative distance of probes attached to or associated with the nucleic acids can be detected, i.e., stretched nucleic acids of the invention may be in a linear configuration, but may also comprise serpentine or other curved or extended configurations. In some cases, for example with the nanopore embodiments, the stretched nucleic acid may not be linear prior to entering the nanopore; in these embodiments, "stretched" means that the nucleic acid enters the nanopore in a linear way such that the order and optionally the relative distance of probes along the decorated nucleic acids can be detected, even though the nucleic acid may be substantially non-linear either before entering the pore or after, or both, as is generally depicted in FIG. 14.

In many embodiments, nucleic acids of the invention are substantially double stranded. By "substantially double stranded" herein is meant that the majority of the nucleic acid is double stranded but contains one or more single stranded regions. In a further embodiment, about 51% to about 99% of a "substantially double stranded" nucleic acid of the invention is double stranded. In a still further embodiment, about 55% to about 90%, about 60% to about 85%, about 65% to about 80%, and about 70% to about 75% of a substantially double stranded nucleic acid of the invention is double stranded. As will be appreciated by those in the art and is further described herein, depending on the "stretching" technology, it may be more or less important to have the single molecule under investigation be substantially double stranded. That is, in some embodiments, gap filling and ligation of nicks may be utilized, while in other embodiments, these steps are not required to allow stretching. In addition, it should be noted that these reactions may be terminated prior to saturation; that is, some gaps and/or nicks can be repaired but not all. It should be noted that this may also be a function of the amount or time of enzymatic exposure of the original target sequence to these enzymes; for example, high concentrations and/or long exposure times to the exonuclease can result in bigger gaps.

Thus, in one aspect, a stretched nucleic acid according to the invention comprises no gaps and/or nicks. In another aspect, a stretched nucleic acid of the invention may comprise one or more gaps, one or more nicks, or a combination of nicks and gaps. The stability of stretched nucleic acids, including stretched nucleic acids comprising one or more gaps and/or nicks, particularly gaps and/or nicks that are located in close proximity on opposite strands, can optionally be increased through crosslinking (such as, in one limiting example, by applying psoralen), by utilizing stabilizing proteins bound to or cross-linked to the nucleic acids (such as, in one non-limiting example, double stranded DNA stabilizing proteins), and/or by incorporating nucleotide analogs such as LNA or PNA, which are usually, (but are not required to be), introduced as part of the labeled probes used to decorate nucleic acids, as described further below.

In some embodiments, as is further described herein, when invasive probes are used, the target nucleic acid may not contain any gaps and/or nicks.

In a further aspect, stretched nucleic acids of the invention are concatemers. By "concatemer" is meant a nucleic acid that contains multiple copies (e.g. "monomers") of a target nucleic acid or a fragment of a target nucleic acid. Such concatemers may be of particular use in analyzing shorter nucleic acids, such as cDNA or shorter fragments of genomic DNA (for example, fragments of ~10-30 kb in length). In one embodiment, concatemers are generated from these shorter nucleic acids, and each of those concatemers will include multiple copies of those shorter nucleic acids. Decorating such concatemers and then detecting the probes (using methods discussed in further detail below) can result in an increased signal to noise ratio and minimize false negatives. In one embodiment, Phi29 can be used to generated 100-300 kb long concatemers comprising, for example, 9 copies of a 30 kb length of nucleic acid or 30-90 copies of a 3 kb length of nucleic acid (3 kb is a typical length of a cDNA molecule). Methods of generating concatemers in accordance with the present invention are described in U.S. patent application Ser. Nos. 11/938,096; 11/981,804; 11/981,797; 11/981,793; 11/981,767; 11/981,761; 11/981,730, filed Oct. 31, 2007; 11/981,685; 11/981,661; 11/981,607; 11/981,605; 11/927,388; 11/927,356; 11/679,124; 11/541,225; 10/547,214; 11/451,692; and 11/451,691, each of which is hereby incorporated in its entirety for all purposes and in particular for all teachings related to concatemers, methods of generating concatemers, and methods of using concatemers.

IID. Decorated Nucleic Acids

As provided herein, the present invention encompasses substrates with stretched decorated nucleic acids. By "decorated nucleic acid" herein is meant a nucleic acid which has at least one labeled probe incorporated into its structure. By "incorporated into its structure' is meant that the labeled probe is associated with the nucleic acid, for example through hybridization to complementary regions on either or both of the nucleic acids of a double stranded target nucleic acid, through ligation, through a combination of ligation and hybridization, or through other methods known in the art for attaching labeled probes to nucleic acids, including post-hybridization cross-linking. By "probe" is meant a nucleic acid, usually single stranded nucleic acid, that comprises one or more detectable label(s) as further outlined herein. In exemplary embodiments, labels may be attached to such oligonucleotide probes at one or both ends and/or to nucleotides within the body of the oligonucleotide probe. Probes of use in the invention are discussed further below.

In one aspect, decorated nucleic acids of the invention may be fully double stranded or may contain one or more gaps and/or nicks. As discussed further below, decorated nucleic acids are "decorated" with probes.

Probes

IID(i). Probe Length

Probes of use in the invention comprise any nucleic acid or set of nucleic acids associated with a detectable label that can be attached to target nucleic acids to form decorated nucleic acids of the invention. In an exemplary aspect, probes of the invention are nucleic acids comprising sequences that will hybridize to some portion, i.e. a domain, of a target nucleic acid. Probes of the present invention are designed to be complementary, and in general, perfectly complementary, to a sequence of the target sequence such that hybridization of a portion target sequence and probes of the present invention occurs.

In many embodiments, the probes are perfectly complementary to the target sequence to which they hybridize; that is, the experiments are run under conditions that favor the formation of perfect basepairing, as is known in the art. As will be appreciated by those in the art, a probe that is perfectly complementary to a first domain of the target sequence could be only substantially complementary to a second domain of the same target sequence; that is, the present invention relies in many cases on the use of sets of probes, for example, sets of hexamers, that will be perfectly complementary to some target sequences and not to others.

In some embodiments, depending on the application, the complementarity between the probe and the target need not be perfect; there may be any number of base pair mismatches, which will interfere with hybridization between the target sequence and the single stranded nucleic acids of the present invention. However, if the number of mismatches is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions. However, for most applications, the conditions are set to favor probe hybridization only if perfectly complementarity exists.

In one embodiment, probes capable of forming a Hoogsteen bond with the target nucleic acid are used. Such probes form a triplex with the target nucleic acid. A probe that binds by Hoogsteen binding enters the major groove of a target nucleic acid and hybridizes with the bases located there. In a further embodiment, probes used in accordance with the present invention can form both Watson-Crick and Hoogsteen bonds with the target nucleic acid. Bis PNA probes, for instance, are capable of both Watson-Crick and Hoogsteen binding to a target nucleic acid molecule.

The probes of use in the invention are generally single stranded, but they are not so limited. For example, when the probe is a bis PNA it can adopt a secondary structure with the target nucleic acid resulting in a triple helix conformation, with one region of the bis PNA clamp forming Hoogsteen bonds with the backbone of the target molecule and another region of the bis PNA clamp forming Watson-Crick bonds with the nucleotide bases of the target molecule.

Probes of use in the invention can be of any size. In one aspect, probes are generally on the order of 100 bases or fewer in length. In a further aspect, probes of the invention are about 3 to about 20 bases in length, with probes of 5, 6, 7, 8, 9 and 10 finding particular use. In a still further aspect, probes of the invention are about 5 to about 90, about 10 to about 80, about 15 to about 70, about 20 to about 60, about 25 to about 50, and about 30 to about 40 bases in length.

In an exemplary embodiment, probes used in accordance with the invention are 6 bases long (also referred to herein as "6-mers" and/or "hexamers"). The optimal length of a probe of use in the invention will depend in part on the length of the target nucleic acid to be analyzed. Longer probes can provide more sequence information but will have fewer points of hybridization along a given nucleic acid, resulting in less "coverage" of that nucleic acid. Longer probes may be useful for pathogen detection or other diagnostics. In addition, as described below, some embodiments utilize pairs of probes, e.g. ligation and/or FRET pairs, such that two probes hybridize to a single gap and can be ligated together and detected in a variety of ways.

Probes for use in the present invention may have both informative and non-informative (such as degenerative or universal) bases. For example, as more fully described below, a probe set can be designed to include 3 degenerative positions and three informational positions, e.g. D-D-D-I-I-I. The degenerative positions contain all four possible bases and the informational positions contain only 1 base. That is, in this example, the set comprises 64 different probes that will hybridize to any target sequence that has any base at the first three positions and the complement of the bases at the informational bases in that order. In many cases, as outlined below, each probe of this set will be labeled with the same label, such that the complement of the informational trimer can be detected. As will be appreciated by those in the art, it is also possible to have the degenerative positions and the informational positions be in any order (e.g. D-I-D-I-I-D, etc.)

In some cases, in addition to or instead of using degenerative bases, universal bases which hybridize to more than one base can be used. For example, inosine can be used. Any combination of these systems can be utilized.

IID(ii). Labeled Probes

Probes of the invention may be provided in one or more sets, in which probes in different sets comprise different probe sequences, and each probe sequence (unless degeneracy is utilized) within a set comprises a unique label.

By "label" or "labeled" herein is meant that a compound has at least one element, isotope or chemical compound attached to enable the detection of the compound. In general, labels of use in the invention include without limitation isotopic labels, which may be radioactive or heavy isotopes, magnetic labels, electrical labels, thermal labels, colored and luminescent dyes, enzymes and magnetic particles as well. Dyes of use in the invention may be chromophores, phosphors or fluorescent dyes, which due to their strong signals provide a good signal-to-noise ratio for decoding.

Many embodiments of the invention include the use of fluorescent labels. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, and others described in the 6th Edition of the Molecular Probes Handbook by Richard P. Haugland, hereby expressly incorporated by reference in its entirety for all purposes and in particular for its teachings regarding labels of use in accordance with the present invention. Commercially available fluorescent nucleotide analogues readily incorporated into the labeling oligonucleotides include, for example, Cy3-dCTP, Cy3-dUTP, Cy5-dCTP, Cy5-dUTP (Amersham Biosciences, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY®R-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA). Other fluorophores available for post-synthetic attachment include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3.5, Cy5.5, and Cy7 (Amersham Biosciences, Piscataway, N.J. USA, and others).

In some embodiments, for example when two probes are used and ligated together, fluorescence resonance energy transfer (FRET) fluorescent pairs are used. Suitable FRET tandem fluorophores include but are not limited to, PerCP-Cy5.5, PE-Cy5, PE-Cy5.5, PE-Cy7, PE-Texas Red, and APC-Cy7; also, PE-Alexa dyes (610, 647, 680) and APC-Alexa dyes.

In some embodiments, the labels are direct or primary labels, e.g. the fluorophore is directly and usually covalently attached to the probe. In alternative embodiments, indirect labels can be used. That is, in these embodiments, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels include, but are not limited to, one of a binding partner pair such as biotin/streptavidin; chemically modifiable moieties; nuclease inhibitors, enzymes such as horseradish peroxidase, alkaline phosphatases, luciferases, etc.

In one embodiment, the secondary label is a binding partner pair. For example, the label may be a hapten or antigen, which will bind its binding partner. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. Preferred binding partner pairs include, but are not limited to, biotin (or imino-biotin) and streptavidin, digeoxinin and Abs, and Prolinx™ reagents (see www.prolinxinc.com/ie4/home.hmtl).

In one of these embodiments, the binding partner pair comprises biotin or imino-biotin and a fluorescently labeled streptavidin or anti-biotin antibody, with the former generally being preferred. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

Other pairs of use in the invention include digoxigenin, which may be incorporated as a label and subsequently bound by a detectably labeled anti-digoxigenin antibody (e.g. fluoresceinated anti-digoxigenin). Similarly, an aminoallyl-dUTP residue may be incorporated into a detection oligonucleotide and subsequently coupled to an N-hydroxy succinimide (NHS) derivitized fluorescent dye, such as those listed supra. In general, any member of a conjugate pair may be incorporated into a detection oligonucleotide provided that a detectably labeled conjugate partner can be bound to permit detection Additional labels of use in the present invention include nanocrystals, sometimes referred to as Quantum Dots or Q-dots, which are known in the art and described generally for example in Bawendi et al. and C. Kagan et al.; *Phys. Rev. Lett.* 76, (1996), pages 1517-1520 and in U.S. Pat. Nos. 6,544,732 and 7,410,810, which are hereby expressly incorporated by reference in their entirety for all purposes, and in particular for their teachings regarding nanocrystals and/or Q-dots as labels for nucleic acids, including all the discussions regarding the shell, core and polymer components, as well as conjugation strategies. Suitable quantum dots include QDot 605 and QDot 650 compositions. In some cases, quantum dots externally conjugated with streptavidin can be used as a secondary label with a biotinylated probe. These result in labels with strong brightness; and in the present invention have been shown to give a signal similar to 3 or 4 conventional fluorophores. However, in some cases the dots may aggregate in nanochannels, and in some instances they "blink", and thus may not be preferred in some instances.

Molecular antennae, also known as "light harvesting polymers" can also be used to label probes (Gaylord et al., PNAS, 2002, 99(17): 10954-10957). These water-soluble conjugated polymers comprise multiple positive charges and emit blue light when irradiated with ultraviolet light. These polymers are capable of collecting a large number of photons—when used in conjunction with a fluorescent dye molecule, the signal available from a single dye can be amplified about ten times through the interaction with the light harvesting polymer. This signal amplification allows the number of dye molecules used with a particular probe to be reduced, thus reducing the overall size of these probes, which can affect hybridization kinetics and stability. These molecular antennae are of particular use with FRET detection methods, discussed in further detail below.

In an exemplary embodiment, nano-beads are used to label probes of the invention. Such nano-beads are generally beads encapsulating or covalently bound to molecules of fluorescent dye. Such beads are well known in the art. In a further embodiment, such beads comprise plastic, glass, metal, as well as other materials or combinations of materials.

Labels can be attached to nucleic acids to form the labeled probes of the present invention using methods known in the art, and to a variety of locations of the nucleosides. For example, attachment can be at either or both termini of the nucleic acid, or at an internal position, or both. For example, attachment of the label may be done on a ribose of the ribose-phosphate backbone at the 2' or 3' position (the latter for use with terminal labeling), in one embodiment through an amide or amine linkage. Attachment may also be made via a phosphate of the ribose-phosphate backbone, or to the base of a nucleotide. Labels can be attached to one or both ends of a probe or to any one of the nucleotides along the length of a probe.

Figure 6:
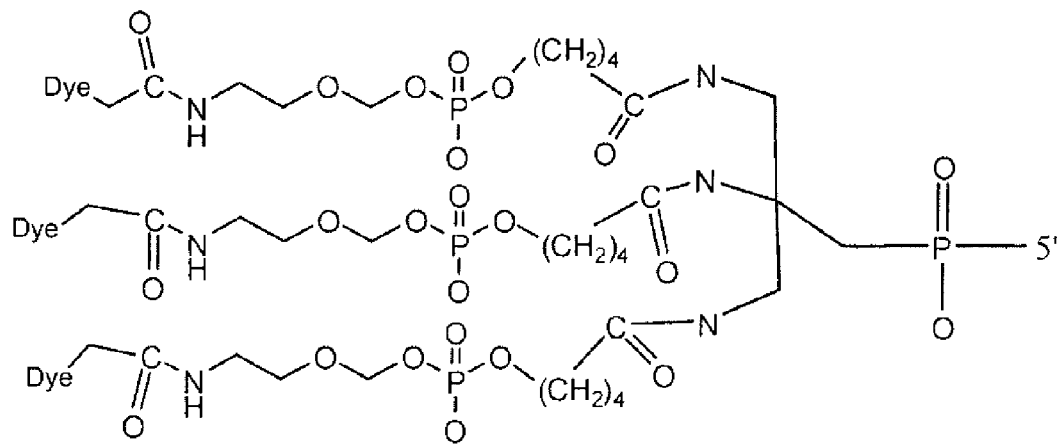
FIG. 6 is an illustration of a treblor label structure that can be used to label probes in accordance with the present invention.

In one embodiment, probes of the invention are labeled with dyes through "treblor linkers" such as those illustrated in FIG. 6. As will be appreciated, the structure illustrated in FIG. 6, and variations and derivations apparent to one of skill in the art are encompassed by the present invention. Treblor linkers such as those illustrated in FIG. 6 can have linkers comprising about 3 to about 15 $NH_2$ groups attached to the 5' phosphate of a polynucleotide. In further embodiments, the linkers comprise about 4 to about 14, about 5 to about 13, about 6 to about 12, about 7 to about 11, and about 8 to about 10 $NH_2$ groups. In a further embodiment, multiple dyes are attached to each "arm" of the treblor linker. In a still further embodiment, about 2 to about 10 dyes are attached to each arm. In a still further embodiment, about 3 to about 9, about 4 to about 8, and about 5 to about 7 dyes are attached per arm. The number of dyes that can be attached to each arm will depend at least in part on the number of NH2 groups in the arms. Although the treblor linker is discussed herein with respect to compounds comprising NH2 groups, it will be appreciated by one of skill in the art that a wide variety of moieties can be used in such treblor arms, selected from substituted or unsubstituted alkyl (such as alkane or alkene linkers of from about C20 to about C30), substituted or unsubstituted heteroalkyl, substituted or unsubstituted aryl, substituted or unsubstituted heteroaryl, substituted or unsubstituted cycloalkyl, and substituted or unsubstituted heterocycloalkyl. In a further embodiment, the arms of such treblor linkers may include poly(ethylene glycol) (PEG) groups, saturated or unsaturated aliphatic structures comprised of single or connected rings, amino acid linkers, peptide linkers, nucleic acid linkers, PNA, LNA, as well as linkers containing phosphate or phosphonate groups.

In addition, as is more fully described below, FRET pairs can also be used as labels in a variety of embodiments.

Although the following description of embodiments of the invention are generally discussed in terms of fluorescent probes, it will be appreciated that probes comprising any kind of detectable label are encompassed by the present invention.

IID(iii). Probes with Multiple Labels

One feature of probes of the invention is that they preferably have a large enough signal to noise ratio to allow detection of single molecules. In one embodiment, signal amplification is achieved by attaching multiple labels to a probe. These multiple labels improve the signal to noise ratio and minimize false negatives caused by failures in the individual label molecules. In one exemplary embodiment, probes of the invention comprise multiple fluorophores. In a further embodiment, probes of the invention comprise at least 2-20, 3-18, 4-16, 5-14, 6-12, and 8-10 fluorophores. The multiple fluorophores on a particular probe can all be the same (i.e., the same color) or can be a combination of two or more different fluorophores.

Multiple fluorophores on a single probe can in some cases show a reduced signal due to quenching that can result from the proximity of the different fluorescent molecules. Probes according to the present invention can be designed to reduce the effect of quenching and thereby further improve the brightness of the signal generated by such probes. As will be appreciated by those in the art, quenching is a function of distance ($1/r^6$), and thus the addition of multiple labels to longer probes may result in less quenching, assuming the spacing between the labels is maximized.

It should be noted that some of the embodiments described herein for the addition of multiple labels may not be well suited to the use of multiple labels in invasive probes, as are more fully described below.

Figure 7A:
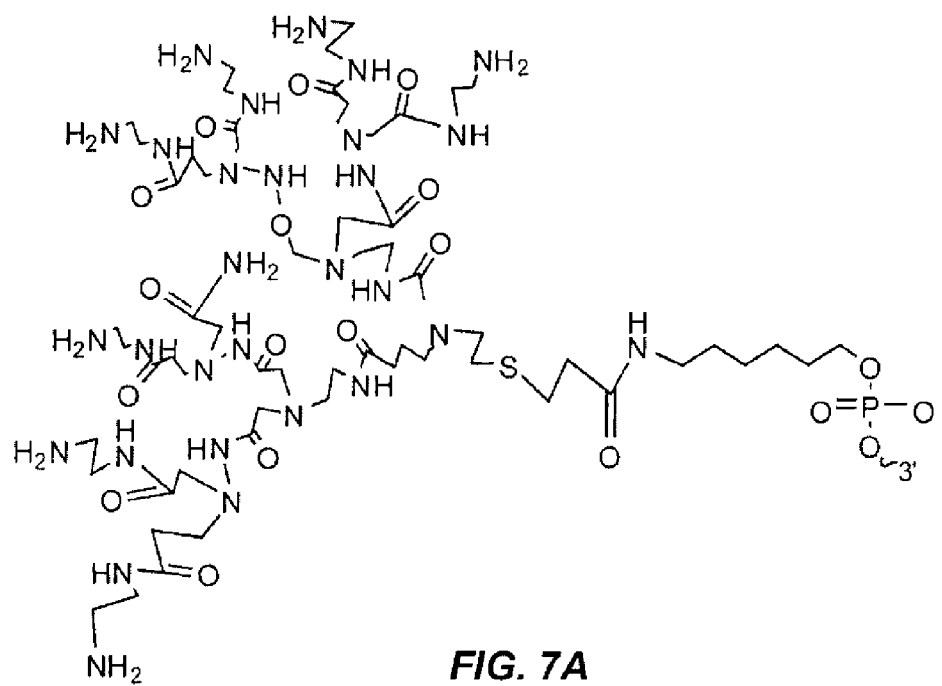
FIG. 7 is an illustration of a dendrimeric non-nucleic acid label that can be used in probes in accordance with the present invention.
Figure 7B:
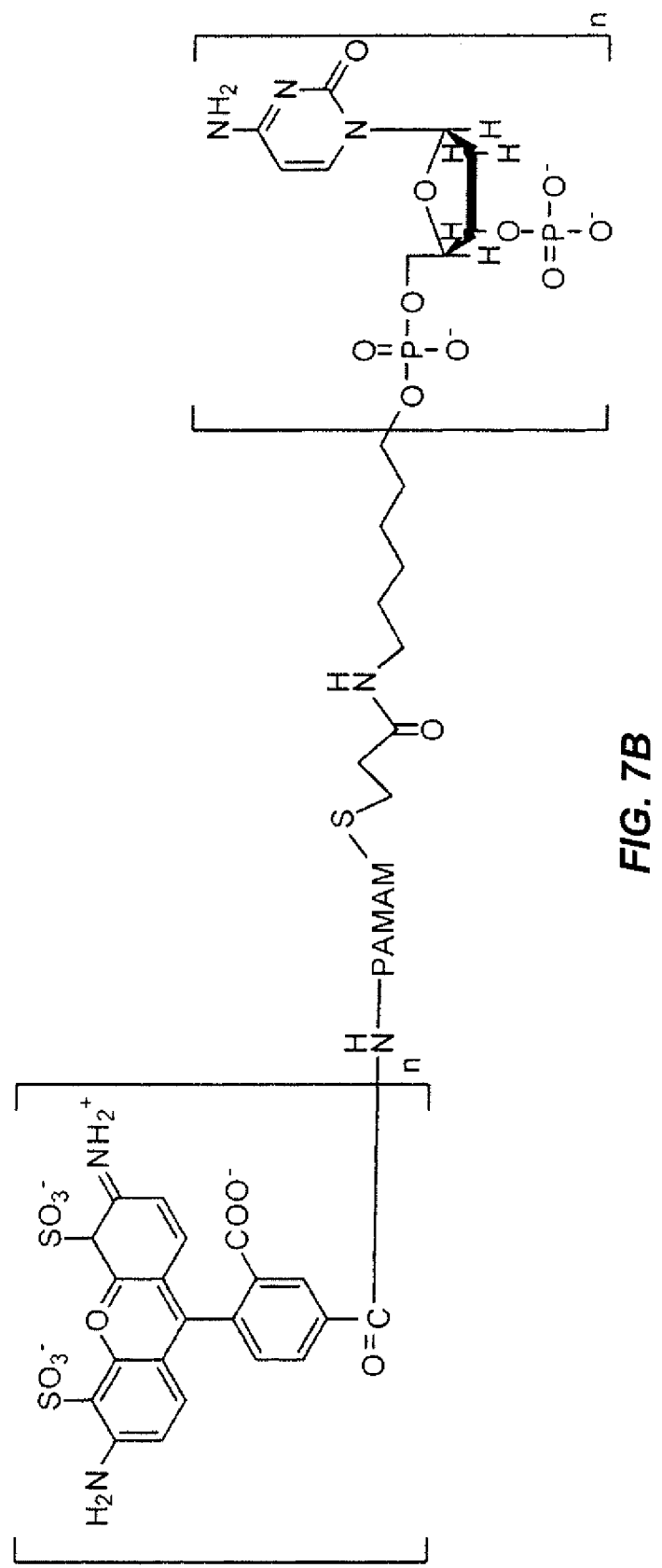
Figure 8:
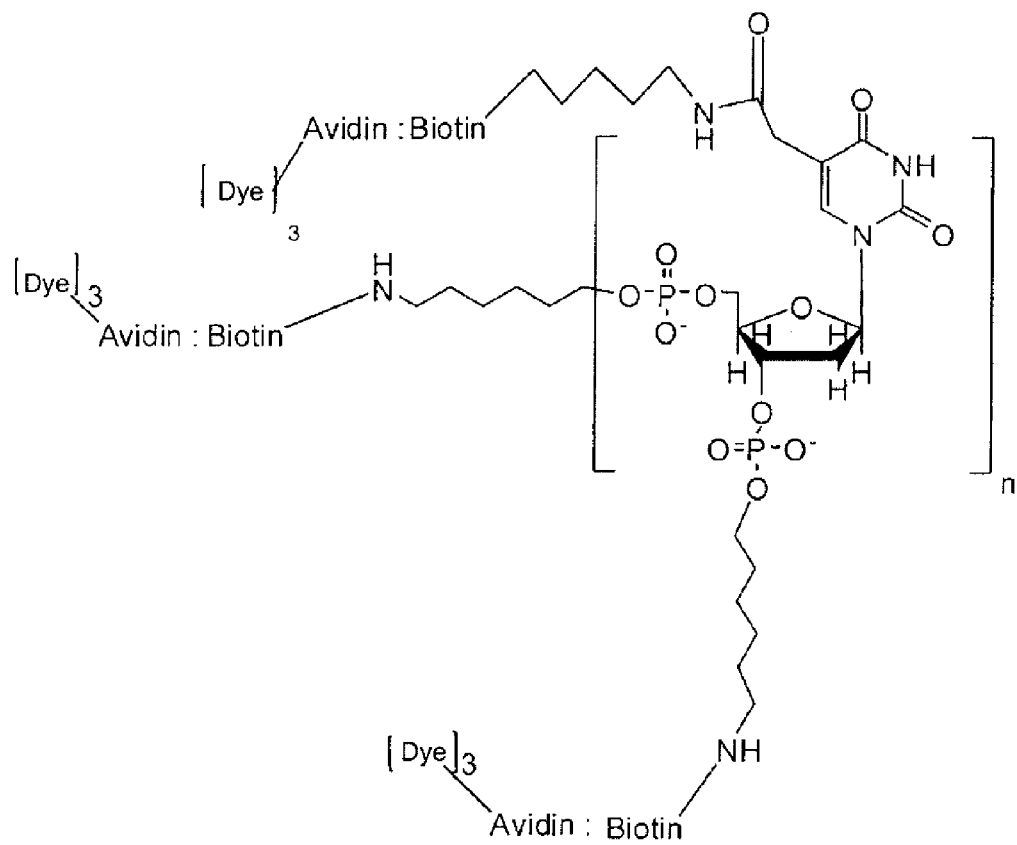
FIG. 8 is an illustration of a label comprising multiple dyes conjugated to the 3' or 5' phosphate or to the nucleobase. It will be appreciated that this is an exemplary embodiment and the label may comprise a subset of these labels in any combination.

There are several ways to incorporate multiple labels into a probe of the invention. In one embodiment, multiple labels are attached to a single probe sequence. Alternatively, dendrimeric probes can be used. By "dendrimeric probe" is meant a probe with a branched structure. Dendrimeric probes fall into three general categories: a dendrimeric probe can be a hybridization complex comprising a number of different nucleic acid sequences that form additional basepairing between them, as is generally depicted in FIG. 5, sometimes referred to herein as "junction structures" or "junction nucleic acid". Alternatively, dendrimeric probes utilize branching, non-nucleic acid components such as linkers to result in the addition of multiple dyes as is generally depicted in FIGS. 6-8. Related probes utilized branched nucleic acids, which can contain a minimal non-nucleic acid linker but are composed mostly of nucleic acids. Dendrimeric probes are generally described in U.S. Pat. No. 5,175,270, which is hereby incorporated by reference in its entirety for all purposes and in particular for its teachings regarding dendrimers.

Figure 5A:
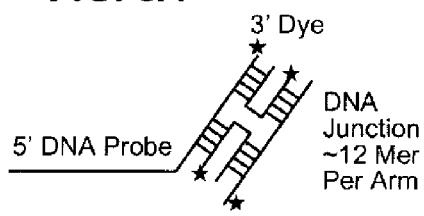
FIGS. 5A-G are illustrations of different exemplary embodiments of junction structures that can be used for labeling probes in accordance with the present invention.
Figure 5B:
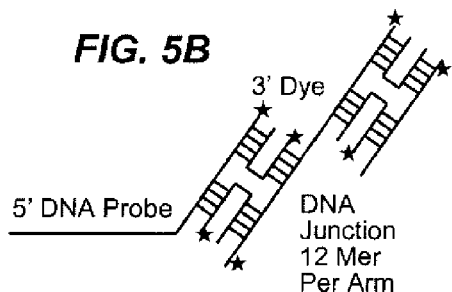
Figure 5C:
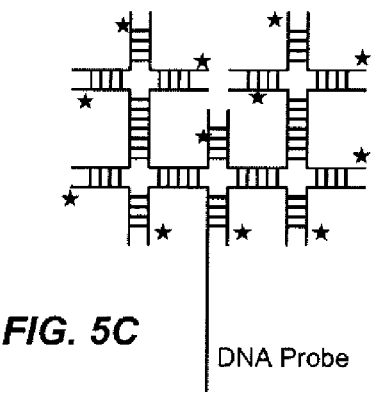
Figure 5D:
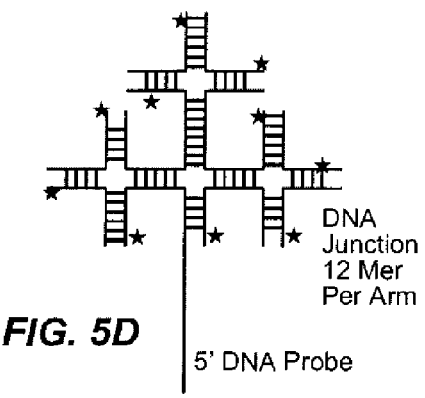

Nucleic acid dendrimeric probes can comprise a wide range of structures. Exemplary structures are illustrated in FIG. 5. The illustrated "junction structures" allow multiple labels to be attached to a single stranded nucleic acid probe. A four-way junction structure is illustrated in FIG. 5A. Four labels can be incorporated into each "arm" of the four-way junction (the labels are illustrated as stars in FIG. 5). Under typical buffer conditions, the four-arm junction structure will undergo rapid conformational changes, which will provide a certain degree of separation between the different labels. When the labels are fluorescent dyes, this separation will minimize potential quenching effects between dyes. A four-way junction structure according to FIG. 5A, in which each arm comprises a 12-mer nucleic acid, is about 8×8 nm in size. It will be appreciated that the structures in FIG. 5 are only exemplary and that junction structures with arms of various lengths are encompassed by the present invention.

FIG. 5 illustrates a junction structure comprising two of the four-way junctions depicted in FIG. 5A. Such a structure allows incorporation of 7 labels, and is about 16×8 nm in size in embodiments in which each arm is a 12-mer nucleic acid. In further embodiments, multiple four-way junctions can be used in order to incorporate still greater numbers of labels into a probe. Exemplary embodiments of such structures are depicted in FIGS. 5C and D. It will be appreciated that different numbers and configurations of four-way junctions can be constructed, and that all such structures are encompassed by the present invention.

Figure 5E:
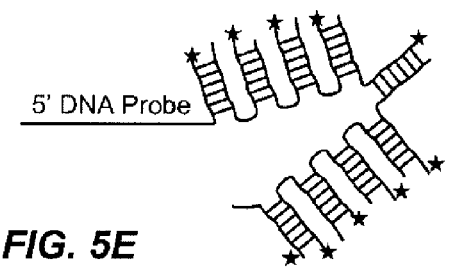
Figure 5F:
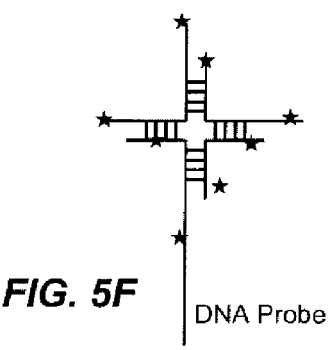

In one embodiment, junction structure nucleic acid probes of the invention may comprise structures other than the four-way junctions depicted in FIGS. 5A-D. Exemplary embodiments of such structures are illustrated in FIGS. 5E-F. It will be appreciated that these are only exemplary embodiments, and that any number of nucleic acid structures which can be used with nucleic acid probes are encompassed by the present invention.

The structure in FIG. 5E provides the ability to attach a label to each arm. It will be appreciated that although a structure with 9 arms is illustrated in FIG. 5E, different numbers of branches are encompassed by this structure. In one exemplary embodiment, a multiple branched structure according to the invention comprises about 3 to about 20 arms. In a further embodiment, such a structure comprises about 5 to about 18, about 6 to about 16, about 8 to about 14, about 9 to about 12, and about 10 to about 11 arms.

FIG. 5F depicts a structure in which asymmetrical helical ends are combined with end-labeling to provide a probe of the invention. Such labels can be incorporated by hybridizing oligonucleotides attached to such labels to the single stranded regions at the 5' and 3' of the asymmetrical helical ends of each arm. These asymmetrical ends may all have the same sequence, or some or all of them may have different sequences. In one embodiment, asymmetrical ends are about 6 nucleotides apart to provide a distance between labels and thus minimize quenching between labels in embodiments in which fluorescent dyes are used.

Figure 5G:
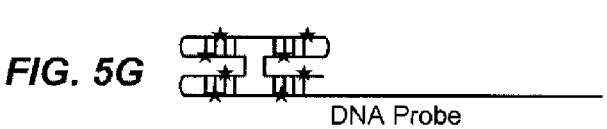

FIG. 5G depicts a structure in which hairpin oligonucleotides are used to link all helical segments of a junction structure. Such hairpin oligonucleotides may be a part of the junction structure, or they may be added to create the structures depicted in FIG. 5G. Labels can be incorporated into such structures by hybridizing oligonucleotides complementary to the loops created by the hairpin oligonucleotides or to other single stranded nucleic acid regions in the structure. In one embodiment, a structure according to FIG. 5G is formed from a single stranded nucleic acid molecule that is designed to self-fold into the desired structure through self-complementary sequence regions, assisted with hairpin oligonucleotide loops. As will be appreciated, structures according to FIG. 5G are not limited to the number of arms depicted, and greater numbers of helical segments can be added to allow incorporation of greater numbers of labels.

Non-nucleic acid dendrimeric probes may also be used in accordance with the present invention.

A number of features are taken into consideration when designing probes for use in the present invention. As discussed above, the ability to support multiple fluorophores is an important feature for the present invention. In addition, homogeneity of labeling across different probes in a set can be of importance, to ensure that probes identifying the same sequence provide a similar intensity of signal to minimize false positives or negatives. Another feature of probe design is their kinetics and stability, which can be affected by their size and structure. Larger probes containing multiple fluorescent molecules, for example, will have different hybridization kinetics than smaller probes comprising only a single label. Stability of such probes can also be affected through alterations to their structure through chemical modification, including crosslinking.

As discussed above, probes of the invention are generally designed to be complementary to a target sequence. In one aspect, a set of probes is provided in which each of the probes of the set comprises a plurality of non-overlapping probe sequences, and each probe sequence comprises a unique label. The number of unique labels that can be used in a given set of probes is limited only by the number of distinguishable labels available for a particular type. For example, at present, fluorescent dyes are generally available in four different distinguishable colors. As such, a given set of probes will in one aspect of the invention comprise four different unique probe sequences. It will be appreciated that as more distinguishable labels become available, the number of distinguishable probes that can be included in a given set will increase.

As is discussed more fully below, in one aspect, decorated nucleic acids of the invention are produced by forming single stranded gaps within a double stranded nucleic acid. Labeled probes such as those discussed above and known in the art can be hybridized to those single stranded gaps. In one embodiment, any gaps not occupied by a probe are repaired using a polymerase and dNTPs, a ligase, or a combination thereof. In another embodiment, only a subset of the gaps not occupied by a probe are repaired, resulting in a decorated nucleic acid that is partially double stranded and partially single stranded. Such partially double stranded decorated nucleic acids will generally retain enough overall structural cohesion to be applied to substrates without breaking, as described below in further detail.

Alternatively, invasive probes are used, which result in structures that contain no gaps or nicks. It is also possible to utilize both types of probes, e.g. to have some invasive probes and some gap/nick probes, as well as to use multiple probes per single gap, as is more fully described below. All of these probes can be used in any combination.

IID(iv). Probe Design

There are a variety of probe design parameters to be used in the present invention. With regard to picking sequences for the label probes, there are several considerations. Preferred probe sets have sequences that fit the selected frequency window; that is, they are dependent on the spatial resolution of the imaging system used to detect the presence of such probes (methods of detection and systems of use for such detection are described in further detail below). In addition, the probes for any particular set should not hybridize to each other; that is, no probe is the reverse complement, or substantially the reverse complement, of another probe in that set. Similarly, no probe should overlap in sequence with another probe in the set; that is, probes should not be competing for hybridization to the same sequence of the target (or to the complements of the other probes). In general, probes that do not contain many repeating bases are also of particular use. Probes generally should not have many common bases with other probes when shifted (or to the complements of the other probes).

The general problem of testing a large number of probes for their suitability in the present invention is a NP-hard problem with complexity, proportional to $k(4^m)^k$, where m is probe length and k is the number of probes.

Figure 15:
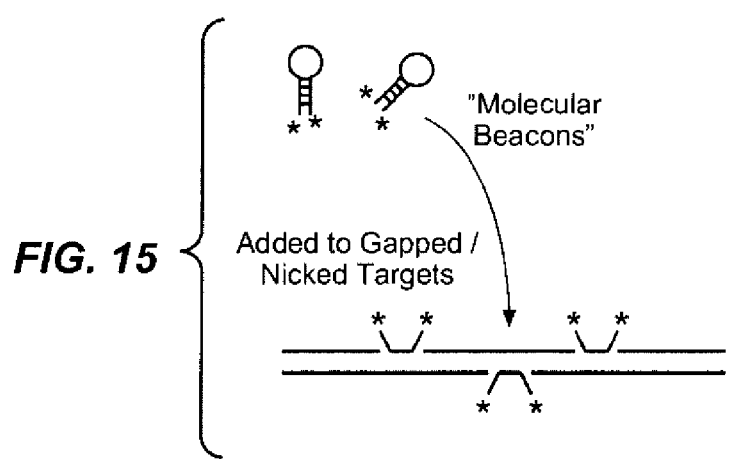
FIG. 15 is a schematic illustration of molecular beacons, which can be added to gapped nucleic acids to form decorated nucleic acids. Such molecular beacons are quenched before hybridization/attachment to the nucleic acids, and the conformational change of attaching to the nucleic acids results in a detectable signal.

In addition to the length and sequence considerations, there area also a variety of probe geometries that can be used. For example, the probes can be straight linear probes with an attached label, or can include additional sequences or polymers as described above for multiple labels. Alternatively, "molecular beacon" or "hairpin" geometries can be used, as will be appreciated by those in the art, generally depicted in FIG. 15, as described in U.S. application Ser. Nos. 08/152,006; 08/439,819, 10/110,907 and in U.S. Pat. Nos. 5,925,517, 6,103,476; 6,150,097, 6,037,130; 7,385,043, all of which are incorporated herein by reference in their entirety for all purposes, for all purposes, and in particular for the figures, legends and accompanying text describing the compositions, methods of using the compositions and methods of making the compositions. In this embodiment, the probe sequence for hybridization to the target sequence is found in the single stranded portion of the hairpin, with labels on the complementary section. In the absence of hybridization to the target, the labels are quenched. Upon hybridization, the labels are separated, are no longer quenched, and result in a signal. As will be appreciated by those in the art, molecular beacons are generally designed such that the Tm of the probe:target complex is higher than that of the "closed hairpin". In one embodiment, including one or more mismatches in the stem of the hairpin may further favor binding to the full-matched target. In a further embodiment, degenerated positions can be included in the part of the hairpin that does not match the target to extend binding to the target.

In some embodiments, pairs of probes are used for each gap, with optional ligation. For example, two 6-mers can be used that hybridize to adjacent target sequences in the gaps, and then ligated together. These can contain either the same label, different labels, or a FRET label pair, resulting in more sequence information per gap. In further embodiments, a combinatorial ligation method may be used to probe all informative 6-mers with two sets of 64 probes, in which the probes have 3 informative bases.

IID(v). Invasive Probes

As an alternative to the nicking and gapping methods of incorporating labeled probes to form a decorated nucleic acid, invasive probes, that rely on the use of recombinase, such as recA, can be used. By "recombinase" herein is meant a protein that, when included with an exogenous targeting polynucleotide, provide a measurable increase in the recombination frequency and/or localization frequency between the targeting polynucleotide (e.g. the label probes of the invention) and an endogenous predetermined DNA sequence. Thus, in a preferred embodiment, increases in recombination frequency from the normal range of $10^{-8}$ to $10^{-4}$ to $10^{-4}$ to $10^{-1}$, preferably $10^{-3}$ to $10^{-1}$, and most preferably $10^{-28}$ to 10, may be achieved.

In the present invention, recombinase refers to a family of RecA-like recombination proteins all having essentially all or most of the same functions, particularly: (i) the recombinase protein's ability to properly bind to and position targeting polynucleotides on their homologous targets and (ii) the ability of recombinase protein/targeting polynucleotide complexes to efficiently find and bind to complementary endogenous sequences. The best characterized recA protein is from E. coli, in addition to the wild-type protein a number of mutant recA proteins have been identified (e.g., recA803; see Madiraju et al., PNAS USA 85(18):6592 (1988); Madiraju et al, Biochem. 31:10529 (1992); Layery et al., J. Biol. Chem. 267:20648 (1992)). Further, many organisms have recA-like recombinases with strand-transfer activities (e.g., Fugisawa et al., (1985) Nucl. Acids Res. 13: 7473; Hsieh et al., (1986) Cell 44: 885; Hsieh et al., (1989) J. Biol. Chem. 264: 5089; Fishel et al., (1988) Proc. Natl. Acad. Sci. (USA) 85: 3683; Cassuto et al., (1987) Mol. Gen. Genet. 208: 10; Ganea et al., (1987) Mol. Cell. Biol. 7: 3124; Moore et al., (1990) J. Biol. Chem. 19: 11108; Keene et al., (1984) Nucl. Acids Res. 12: 3057; Kimeic, (1984) Cold Spring Harbor Symp. 48: 675; Kmeic, (1986) Cell 44: 545; Kolodner et al., (1987) Proc. Natl. Acad. Sci. USA 84: 5560; Sugino et al., (1985) Proc. Natl. Acad. Sci. USA 85: 3683; Halbrook et al., (1989) J. Biol. Chem. 264: 21403; Eisen et al., (1988) Proc. Natl. Acad. Sci. USA 85: 7481; McCarthy et al., (1988) Proc. Natl. Acad. Sci. USA 85: 5854; Lowenhaupt et al., (1989) J. Biol. Chem. 264: 20568, which are incorporated herein by reference. Examples of such recombinase proteins include, for example but not limited to: recA, recA803, uvsX, and other recA mutants and recA-like recombinases (Roca, A. I. (1990) Crit. Rev. Biochem. Molec. Biol. 25: 415), sep1 (Kolodner et al. (1987) Proc. Natl. Acad. Sci. (U.S.A.) 84:5560; Tishkoff et al. Molec. Cell. Biol. 11:2593), RuvC (Dunderdale et al. (1991) Nature 354: 506), DST2, KEM1, XRN1 (Dykstra et al. (1991) Molec. Cell. Biol. 11:2583), STP.alpha./DST1 (Clark et al. (1991) Molec. Cell. Biol. 11:2576), HPP-1 (Moore et al. (1991) Proc. Natl. Acad. Sci. (U.S.A.) 88:9067), other target recombinases (Bishop et al. (1992) Cell 69: 439; Shinohara et al. (1992) Cell 69: 457); incorporated herein by reference. RecA may be purified from E. coli strains, such as E. coli strains JC12772 and JC15369 (available from A. J. Clark and M. Madiraju, University of California-Berkeley, or purchased commercially). These strains contain the recA coding sequences on a "runaway" replicating plasmid vector present at a high copy numbers per cell. The recA803 protein is a high-activity mutant of wild-type recA. The art teaches several examples of recombinase proteins, for example, from Drosophila, yeast, plant, human, and non-human mammalian cells, including proteins with biological properties similar to recA (i.e., recA-like recombinases), such as Rad51, Rad57, dmel from mammals and yeast, and Pk-rec (see Rashid et al., Nucleic Acid Res. 25(4):719 (1997), hereby incorporated by reference). In addition, the recombinase may actually be a complex of proteins, i.e. a "recombinosome". In addition, included within the definition of a recombinase are portions or fragments of recombinases which retain recombinase biological activity, as well as variants or mutants of wild-type recombinases which retain biological activity, such as the E. coli recA803 mutant with enhanced recombinase activity.

In a preferred embodiment, recA is used. For example, recA protein is typically obtained from bacterial strains that overproduce the protein: wild-type E. coli recA protein and mutant recA803 protein may be purified from such strains. Alternatively, recA protein can also be purchased from, for example, Pharmacia (Piscataway, N.J.) or Boehringer Mannheim (Indianapolis, Ind.).

RecA proteins, and its homologs, form a nucleoprotein filament when it coats a single-stranded DNA. In this nucleoprotein filament, one monomer of recA protein is bound to about 3 nucleotides. This property of recA to coat single-stranded DNA is essentially sequence independent, although particular sequences favor initial loading of recA onto a polynucleotide (e.g., nucleation sequences). The nucleoprotein filament(s) can be formed on essentially any DNA molecule and can be formed in cells (e.g., mammalian cells), forming complexes with both single-stranded and double-stranded DNA, although the loading conditions for dsDNA are somewhat different than for ssDNA.

Embodiments utilizing recA invasive probes can utilize single stranded probes, e.g. one probe per location, which forms single "D-loops", or two, forming "double D-loops". In one embodiment, single recA probes are used. In this embodiment, due to recA requirements, it may be desirable to utilize a mixture of informational bases and degenerative bases to increase the length of the probe; that is, recA coated probes generally favor longer sequences. Accordingly, for example, there may be 6 informational bases (preferably, but not always in sequential order), and degenerative bases on one or both termini of the probe. For example, there may be 5-20 (ore more) degenerative bases attached to 6 informational bases for recA loading and binding. However, single D-loops can be inherently somewhat unstable, due to the competition of the additional strand of target nucleic acid (e.g. if the probe is "Crick", it is hybridized to target "Watson", and target "Crick" will tend to kick out the probe "Crick"), it can be desirable to either use a second recA strand and/or to extend the invasive probe. For example, polymerase and dNTPs can be added during the invasion process to extend the invasion probe and thus make it more stable; see for example U.S. 2004/0224336, hereby incorporated by reference in its entirety, and in particular for the enzymatic conditions outlined therein (although this reference generally discloses only the addition of a single allele specific nucleotide, these conditions are suitable for the incorporation of a plurality of nucleotides). However, in some cases, it is not desirable to have unlimited extension reactions, and thus in some embodiments some ratio of termination nucleotides, such as dideoxyNTPs (ddNTPs) are added, for example to allow extension of 20-30-50-100-200 bases. Alternatively, or in addition to, some embodiments utilize two invasive probes with optional extension. In this embodiment, two substantially complementary targeting polynucleotides are used. In one embodiment, the targeting polynucleotides form a double stranded hybrid, which may be coated with recombinase, although when the recombinase is recA, the loading conditions may be somewhat different from those used for single stranded nucleic acids. The two complementary single-stranded targeting polynucleotides are usually of equal length, although this is not required. However, as noted below, the stability of the four strand hybrids of the invention is putatively related, in part, to the lack of significant unhybridized single-stranded nucleic acid, and thus significant unpaired sequences are not preferred. Furthermore, as noted above, the complementarity between the two targeting polynucleotides need not be perfect. The two complementary single-stranded targeting polynucleotides are simultaneously or contemporaneously introduced into a target cell harboring a predetermined endogenous target sequence, generally with at lease one recombinase protein (e.g., recA). Under most circumstances, it is preferred that the targeting polynucleotides are incubated with recA or other recombinase prior to introduction to the target nucleic acid, so that the recombinase protein(s) may be "loaded" onto the targeting polynucleotide(s), to coat the nucleic acid, as is described below. Incubation conditions for such recombinase loading are described infra, and also in U.S. Ser. No. 07/755,462, filed 4 Sep. 1991; U.S. Ser. No. 07/910,791, filed 9 Jul. 1992; and U.S. Ser. No. 07/520,321, filed 7 May 1990, each of which is incorporated herein by reference. A targeting polynucleotide may contain a sequence that enhances the loading process of a recombinase, for example a recA loading sequence is the recombinogenic nucleation sequence poly[d(A-C)], and its complement, poly[d(G-T)]. The duplex sequence poly[d(A-C)d(G-T)$_n$, where n is from 5 to 25, is a middle repetitive element in target DNA.

RecA protein coating of targeting polynucleotides is typically carried out as described in U.S. Ser. No. 07/910,791, filed 9 Jul. 1992 and U.S. Ser. No. 07/755,462, filed 4 Sep. 1991, and PCT US98/05223, which are incorporated herein by reference. Briefly, the targeting polynucleotide, whether double-stranded or single-stranded, is denatured by heating in an aqueous solution at 95-100° C. for five minutes, then placed in an ice bath for 20 seconds to about one minute followed by centrifugation at 0° C. for approximately 20 sec, before use. When denatured targeting polynucleotides are not placed in a freezer at −20° C. they are usually immediately added to standard recA coating reaction buffer containing ATP-gamma-S, at room temperature, and to this is added the recA protein. Alternatively, recA protein may be included with the buffer components and ATP-gamma-S before the polynucleotides are added.

RecA coating of targeting polynucleotide(s) is initiated by incubating polynucleotide-recA mixtures at 37° C. for 10-15 min. RecA protein concentration tested during reaction with polynucleotide varies depending upon polynucleotide size and the amount of added polynucleotide, and the ratio of recA molecule:nucleotide preferably ranges between about 3:1 and 1:3. When single-stranded polynucleotides are recA coated independently of their homologous polynucleotide strands, the mM and μM concentrations of ATPgamma-S and recA, respectively, can be reduced to one-half those used with double-stranded targeting polynucleotides (i.e., recA and ATP-gamma-S concentration ratios are usually kept constant at a specific concentration of individual polynucleotide strand, depending on whether a single- or double-stranded polynucleotide is used).

RecA protein coating of targeting polynucleotides is normally carried out in a standard 1× RecA coating reaction buffer. 10× RecA reaction buffer (i.e., 10×AC buffer) consists of: 100 mM Tris acetate (pH 7.5 at ° C.), 20 mM magnesium acetate, 500 mM sodium acetate, 10 mM DTT, and 50% glycerol). All of the targeting polynucleotides, whether double-stranded or single-stranded, typically are denatured before use by heating to 95-100° C. for five minutes, placed on ice for one minute, and subjected to centrifugation (10,000 rpm) at 0° C. for approximately 20 seconds (e.g., in a Tomy centrifuge). Denatured targeting polynucleotides usually are added immediately to room temperature RecA coating reaction buffer mixed with ATPgamma-S and diluted with double-distilled H$_2$O as necessary.

A reaction mixture typically contains the following components: (i) 0.2-4.8 mM ATPgamma-S; and (ii) between 1-100 ng/μl of targeting polynucleotide. To this mixture is added about 1-20 μl of recA protein per 10-100 μl of reaction mixture, usually at about 2-10 mg/ml (purchased from Pharmacia or purified), and is rapidly added and mixed. The final reaction volume—for RecA coating of targeting polynucleotide is usually in the range of about 10-500 μl. RecA coating of targeting polynucleotide is usually initiated by incubating targeting polynucleotide-RecA mixtures at 37° C. for about 10-15 min.

RecA protein concentrations in coating reactions varies depending upon targeting polynucleotide size and the amount of added targeting polynucleotide: recA protein concentrations are typically in the range of 5 to 50 μM. When single-stranded targeting polynucleotides are coated with recA, independently of their complementary strands, the concentrations of ATPgamma-S and recA protein may optionally be reduced to about one-half of the concentrations used with double-stranded targeting polynucleotides of the same length: that is, the recA protein and ATPgamma-S concentration ratios are generally kept constant for a given concentration of individual polynucleotide strands.

The coating of targeting polynucleotides with recA protein can be evaluated in a number of ways. First, protein binding to DNA can be examined using band-shift gel assays (McEntee et al., (1981) J. Biol. Chem. 256: 8835). Labeled polynucleotides can be coated with recA protein in the presence of ATPgamma-S and the products of the coating reactions may be separated by agarose gel electrophoresis. Following incubation of recA protein with denatured duplex DNAs the recA protein effectively coats single-stranded targeting polynucleotides derived from denaturing a duplex DNA. As the ratio of recA protein monomers to nucleotides in the targeting polynucleotide increases from 0, 1:27, 1:2.7 to 3.7:1 for 121-mer and 0, 1:22, 1:2.2 to 4.5:1 for 159-mer, targeting polynucleotide's electrophoretic mobility decreases, i.e., is retarded, due to recA-binding to the targeting polynucleotide. Retardation of the coated polynucleotide's mobility reflects the saturation of targeting polynucleotide with recA protein. An excess of recA monomers to DNA nucleotides is required for efficient recA coating of short targeting polynucleotides (Leahy et al., (1986) J. Biol. Chem. 261: 954).

A second method for evaluating protein binding to DNA is in the use of nitrocellulose fiber binding assays (Leahy et al., (1986) J. Biol. Chem. 261:6954; Woodbury, et al., (1983) Biochemistry 22(20):4730-4737. The nitrocellulose filter binding method is particularly useful in determining the dissociation-rates for protein:DNA complexes using labeled DNA. In the filter binding assay, DNA:protein complexes are retained on a filter while free DNA passes through the filter. This assay method is more quantitative for dissociation-rate determinations because the separation of DNA:protein complexes from free targeting polynucleotide is very rapid.

III. Methods of Making Compositions of the Invention

In one aspect, the present invention provides methods of making compositions comprising substrates with stretched decorated nucleic acids.

As described above, stretched decorated nucleic acids of the invention are single or double stranded nucleic acids decorated with a plurality of probes and linearized such that the order and relative distance of those probes can be detected.

In general, a target nucleic acid is used to generate stretched decorated nucleic acids of the invention. The term "target nucleic acid" refers to a nucleic acid of interest. In one aspect, target nucleic acids of the invention are genomic nucleic acids. Target nucleic acids include naturally occurring or genetically altered or synthetically prepared nucleic acids (such as genomic DNA from a mammalian disease model). Target nucleic acids can be obtained from virtually any source and can be prepared using methods known in the art. For example, target nucleic acids can be directly isolated without amplification, isolated by amplification using methods known in the art, including without limitation polymerase chain reaction (PCR), multiple displacement amplification (MDA), rolling circle amplification (RCA), rolling circle amplification (RCR) and other amplification methodologies. Target nucleic acids may also be obtained through cloning, including cloning into vehicles such as plasmids, yeast, and bacterial artificial chromosomes.

In one aspect, stretched decorated nucleic acids are formed from genomic DNA. In an exemplary embodiment, genomic DNA is isolated from a target organism. By "target organism" is meant an organism of interest and as will be appreciated, this term encompasses any organism from which nucleic acids can be obtained. Methods of obtaining nucleic acids from target organisms are well known in the art.

IIIA. Fragmenting

In one aspect, a preliminary step for making stretched decorated nucleic acids of the invention includes fragmenting nucleic acids isolated from a target organism. Methods for fragmenting nucleic acids are known in the art and include, but are not limited to, nonspecific endonuclease digestion, restriction enzyme digestion, physical shearing (e.g., by ultrasound), and treatment with sodium hydroxide. The size of fragments generated can be controlled by the extent (i.e., length of time) of mechanical or enzymatic fragmenting.

In general, the size of the desired fragments may depend on the detection system used. In general, fragments for use in nanochannel applications range in size from about 1 to about 500 kb in length, with from about 10 to about 100 kb in length finding particular use in some embodiments. Fragments of specific lengths can be generated using methods known in the art, for example by modifying the time used for mechanical or enzymatic fragmentation, by using restriction endonucleases whose recognition sites appear with a known frequency in certain genomes, and other methods known in the art.

Fragments may be separated by size, for example using gel electrophoresis, sizing columns, filters, and other methods known in the art, to obtain desired fragment lengths In one embodiment, nested fragments are generated to produce a sample of fragmented nucleic acids for making decorated nucleic acids of the invention. Such nested fragments can be of particular use in sequencing applications in which sequence information obtained from different fragments is assembled using methods known in the art and described below in further detail. In one embodiment, nested fragments are created from starting seed fragments through deletions of defined size. Such nested fragments have exact-end deletions generated in one embodiment by first preparing a partial digest within one or a pool of frequent cutting restriction enzymes that produce 10-200 kb long fragments that start at predefined restriction enzyme recognition sequence sites approximately every 50-200 bases. An aliquot from this first digest is used directly in assays as described further herein. The remainder of the fragments are subjected to deletion of a known number of bases from each end—in one embodiment this is accomplished through a number of consecutive cycles of ligation of an adaptor with a type IIs restriction enzyme binding site to ends of the fragments and then cleavage with the type IIs restriction enzyme. In one embodiment, the type IIs restriction enzyme is an exact cutter. By "exact cutter" is meant that the restriction endonuclease cuts at a known distance from the recognition site in all or most of the polynucleotide molecules. Some "wobbling" exists, so that even with an exact cutter there can be a very small (e.g., 1-10%) amount of cutting that happens one or two bases from the expected cutting site, but this number is small enough so as to not unduly change the fundamental methods of the invention. Exact cutter endonucleases include without limitation Type IIs restriction endonucleases such as Eco57M I, Mme I, Acu I, Bpm I, BceA I, Bbv I, BciV I, BpuE I, BseM II, BseR I, Bsg I, BsmF I, BtgZ I, Eci I, EcoP15 I, Eco57M I, Fok I, Hga I, Hph I, Mbo II, Mnl I, SfaN I, TspDT I, TspDW I, Taq II, and the like, all of which can be used to generate nested fragments according to the present invention. Sequence information obtained from the fragments subjected to different numbers of cycles of deletion can be compared to aid in assembly of the full sequence of the original target nucleic acid.

In one embodiment, after fragmenting, an amplification step can be applied to the population of fragmented nucleic acids to ensure that a large enough concentration of all the fragments is available for subsequent steps of creating the decorated nucleic acids of the invention and using those nucleic acids for obtaining sequence information. Such amplification methods are well known in the art and include without limitation: polymerase chain reaction (PCR), ligation chain reaction (sometimes referred to as oligonucleotide ligase amplification OLA), cycling probe technology (CPT), strand displacement assay (SDA), transcription mediated amplification (TMA), nucleic acid sequence based amplification (NASBA), rolling circle amplification (RCA) (for circularized fragments), and invasive cleavage technology.

IIIB. Enriching for Target Fragments

In a further embodiment, a sample of fragmented nucleic acids are enriched for target fragments. By "target fragments" is meant fragments of interest for a particular application, for example, in clinical diagnostics, target fragments would include those fragments derived from a particular part of the genome or that contain particular marker sequences that indicate a disease or the presence of a pathogen. Methods for enriching a population of fragmented nucleic acids for target fragments are well known in the art.

In an exemplary embodiment, capture probes are used to enrich for target fragments. Such capture probes will hybridize to target fragments, after which any fragments not hybridized to the capture probes can be removed from the sample. The captured target fragments can then be released from the capture probes using methods well characterized in the art.

If a sample of fragmented nucleic acids comprises double stranded molecules, an exonuclease can be applied to remove a number of bases of one end of one strand. In an exemplary embodiment, about 2000 to about 5000 bases are removed from one end of one strand. In a further embodiment, about 2100 to about 4500, about 2200 to about 4000, about 2300 to about 3500 and about 2400 to about 3000 bases are removed from one end of one strand. Various enzymes are available for removing bases of one strand including without limitation Lambda exonuclease or Exonuclease III. Capture probes will be able to hybridize to the resultant single stranded region of the fragment, thereby capturing fragments containing regions of interest. In a still further embodiment, multiple probes can be prepared and hybridized per fragment of interest to assure capture. Capture probes can be designed to select for each of the two strands to hybridize targeted regions from both ends. Such consecutive "double capture" may also be performed to eliminate fragments that are of a shorter length than is desired for later uses, for example, in assays detecting specific target sequences. Capture probes can be prepared in large quantities as a pool in an amount sufficient for thousands of preparations. In an exemplary embodiment, a set of 1000-10,000 capture probes are prepared for use in accordance with the present invention.

In a further exemplary embodiment, fragments tagged with biotin and can be captured on streptavidin coated-beads. Any unbound fragments are discarded and the captured fragments then released, generally by cutting the link to the bead using methods known in the art, for example by using enzymes specific for that link.

In an exemplary embodiment, a sample of fragmented nucleic acids is enriched using a biotin-streptavidin system. For example, target fragments of interest are tagged with biotin and captured using streptavidin coated beads. Unbound fragments are washed away and then bound fragments can be released by cleaving the link between the bead and the fragment.

In one exemplary embodiment, a sample of fragmented nucleic acids is enriched using PCR to amplify fragments with selected sequences. Such methods are well known in the art and are described for example in *PCR Primer: A Laboratory Manual, and Molecular Cloning: A Laboratory Manual* (from Cold Spring Harbor Laboratory Press). In a further embodiment, quantitative PCR can be used to determine that all targeted fragments are present in sufficient quantities. For many applications, including detecting specific target sequences and/or polymorphisms, 10,000 or more copies can ensure proper coverage of the target regions.

Other methods of enriching samples of fragmented nucleic acids are known in the art and encompassed by the methods of the present invention.

It should also be noted that it is possible to enrich for sequences prior to fragmentation; for example, it may be desirable to enrich for a particular chromosome prior to the fragmentation. In one example, chromosome flow sorting is used to enrich for sequences prior to fragmenting.

IIIC. Decorating Nucleic Acids

The present invention provides methods for forming stretched decorated nucleic acids of the invention. In one aspect, decorated nucleic acids are formed by labeling nucleic acids with detectable probes.

In one aspect, probes are incorporated into the structure of a nucleic acid. In one embodiment, probes are incorporated into the structure of a nucleic acid every 0.5-10 kb. In a further embodiment, probes are incorporated every 1000-2000, 1500-9000, 2000-8000, 2500-7000, 3000-6000, 3500-5500, and 4000-5000 bases. As discussed further herein, the frequency at which probes are incorporated along the length of a nucleic acid can be influenced by the size and structure of the probes, including the size and structure of their labels, as well as by reaction conditions, including the temperature at which the reactions incorporating the probes into the nucleic acid (which are described further below) are conducted.

In general, probes are incorporated into the structure of a double stranded nucleic acid.

Decoration by Generating Single Stranded Regions in a Double Stranded Nucleic Acid In one embodiment, probes are incorporated into a double stranded nucleic acid in a method in which single stranded regions are created along the length of the double stranded nucleic acid, and probes as described herein hybridize to those single stranded regions. A schematic illustration of such a method is provided in FIG. 1.

In one embodiment, a nicking enzyme is added to a double stranded nucleic acid to produce a nicked nucleic acid (see FIG. 1B). Nicking enzymes are known in the art, and are generally altered restriction enzymes that hydrolyze only one strand of the duplex, to produce DNA molecules that are "nicked", rather than cleaved. Examples of nicking enzymes of use in the present invention include without limitation NtCViPii, Nt.BstNBI, a naturally occurring thermostable nicking endonuclease cloned from *Bacillus Stereothermophilus*, Nb.BsrDI and Nb.BtsI, naturally occurring large subunits of thermostable heterodimeric enzymes, Nt.AlwI, a derivative of the restriction enzyme AlwI, Nb.BbvCI, Nt.BbvCI and Nb.BsmI, a bottom-strand specific variant of BsmI discovered from a library of random mutants, all of which are available from commercial suppliers such as New England Biolabs. Different nicking enzymes will nick at different frequencies. For example, some nicking enzymes will nick at a frequency of about 1 nick every 100 bases. In a further embodiment, nicking enzymes are used that nick at a frequency of about 1 nick every 90, 80, 70, 60, 50, 40, 30, 20, 10 and 5 bases.

In certain situations, a nicking enzyme may nick a nucleic acid in the same location on both strands. Such a situation could result in the nucleic acid breaking in subsequent uses, particularly when stretched according to methods described below. One method for preventing this possibility is to crosslink the nucleic acid to stabilize its overall structure. Such crosslinking methods are known in the art.

In a further embodiment, an exonuclease is applied to widen nicks created by the nicking enzyme to create gapped nucleic acids comprising a series of single stranded gaps along their lengths (FIG. 1C). Exonucleases of use in the present invention are known in the art and include without limitation: RecJ, Lambda Exo, and T7 Exo, ExoIII and the like. ExoIII is of use in certain aspects of the present invention, because it will cut 20 bases and release those cut bases. This release of the cut portion of the nucleic acid can be useful in generating gapped nucleic acids in accordance with the present invention.

In a further embodiment, probes of the invention are added to the gapped nucleic acids and hybridize to the single stranded regions created by the application of the nicking and exonuclease enzymes (FIG. 1D). In this embodiment, probes comprise probe sequences that are complementary to single stranded regions of the nucleic acids. Hybridization of the probes results in a double stranded nucleic acid "decorated" with at least one probe. Although the illustration in FIG. 1D depicts only probes labeled at their 3' ends, it will be understood that the present invention encompasses probes labeled at one or both ends or at one of the nucleotides within the body of the probe, as discussed further above. FIG. 1D only depicts an exemplary embodiment for the sake of clarity.

In a still further embodiment, a polymerase enzyme and nucleotides are applied to the gapped nucleic acids comprising hybridized probes to "fill in" remaining single stranded regions (represented by the asterisks in FIG. 1E). In one embodiment, all of the single stranded regions are repaired in this way. This embodiment is pictured in FIG. 1E. In another embodiment, only a subset of the single stranded regions are repaired. Such partially repaired decorated nucleic acids are encompassed by the present invention. Polymerases of use in this aspect of the invention are known in the art and include without limitation: Taq polymerases, *E. coli* DNA Polymerase 1, Klenow fragment, reverse transcriptases, φ29 related polymerases including wild type φ29 polymerase and derivatives of such polymerases, T7 DNA Polymerase, T5 DNA Polymerase, RNA polymerases.

In a still further embodiment, a ligase is applied to further repair the decorated nucleic acid. As with the filling in of gaps using nucleotides and a polymerase enzyme, the ligase may act on all of the nucleotides needing repair or only on a subset of such nucleotides. Ligases of use in the invention are known in the art and include without limitation DNA ligase I, DNA ligase II, DNA ligase III, DNA ligase IV, *E. coli* DNA ligase, Taq ligase, T4 DNA ligase, T4 RNA ligase 1, T4 RNA ligase 2, and the like.

In one embodiment, the application of the nicking enzyme, the exonuclease, the probes and optionally the polymerase and nucleotides and ligase is conducted in a sequential manner, i.e., first the nicking enzyme is applied to create nicks, the exonuclease is applied to widen the nicks into gaps, the probes are then applied to hybridize to the gaps and then the polymerase, nucleotides, and ligase are optionally added to repair remaining single stranded regions.

In another embodiment, the nicking enzyme, the exonuclease, the probes, and optionally the polymerase, nucleotides and ligase are applied to the nucleic acid simultaneously. In this embodiment, the combined action of these elements serves to stochastically create gaps and then fill in those gaps with either a probe or nucleotides or a combination of both. Applying all of these elements at once provides a solution to the problem of finding the appropriate point along a long nucleic acid molecule for a relatively shorter probe to hybridize. The combined activity of all of these enzymes thus provides a method for "scanning" along a nucleic acid molecule and stochastically inserting the appropriate probes to generate the decorated nucleic acids of the invention. In this embodiment, most of the time the exposed single stranded nucleic acid will not have a binding site for the probes used and the polymerase will fill and ligase will seal the gap with the nucleotides. If the single stranded region does have a binding site for one of the probes, the probe will bind (or two or more probes will bind) before the polymerase fills the single-stranded gap.

In a further embodiment, the frequency of the simultaneously occurring nicking, generating gaps, and repair will be at a frequency such that at any particular moment less than 10% of the nicking sites are nicked.

In one embodiment, rather than a nicking enzyme, chemical nicking is used. Chemical nicking can be accomplished using compounds including without limitation piperidine, dimethyl sulfate, hydrazine, as well as combinations of these and/or other chemicals apparent to one of skill in the art. Chemical nicking generally has no frequency limitation. In this embodiment, a low efficiency 3' exonuclease, such as a polymerase with 3' exonuclease activity, can be used to widen the nicks into gaps. If one or more probes are present that are complementary to the gap region, the probe will hybridize, and this hybridization will prevent the polymerase from filling in the gap with nucleotides. In a further embodiment, two probes may hybridize adjacent to each other in the gap and ligate. In this case again this hybridization-ligation reaction will prevent the polymerase from filling in the gap.

As discussed above, not all of the single stranded regions remaining after hybridization of the probes will necessarily be repaired. In addition, in some embodiments, a probe will hybridize to a complementary region of the nucleic acid, but will not have a free terminus for ligation to an adjacent nucleotide. This may in particular occur with probes that are labeled at one or both ends, as described above. For example, in FIG. 1D, the label (depicted as a circle) is attached to the 3' end of the probe. Thus, the 3' end of the probe would not be available for ligation to an adjacent nucleotide.

Figure 4C:
Figure 4D:

In a further embodiment, two probes will hybridize adjacent to each to each other in the same gap of a gapped nucleic acid. These adjacently hybridized probes may or may not ligate to each other to form a ligated complex. As shown in FIG. 4, depending on where the probes are labeled, the hybridized probes may not have a free terminus available for ligation. FIGS. 4B-2D illustrate examples of probes that may not be able to ligate to each other even when hybridized in adjacent positions. The labels, depicted as circles, occupy one end of the probe, and the probes hybridize in such a way that their free ends are not available for ligation to each other. FIG. 4A and FIG. 4E show examples in which adjacently hybridized probes can ligate to each other. FIG. 4A illustrates the situation in which the 3' end of a 5' labeled probe is free to ligate to a 5' end of a 3' labeled probe. FIG. 4E illustrates a situation in which the probes are labeled at an interior position, leaving both termini free for ligation. It is noted that the illustration in FIG. 4 shows probes inserted only in the top strand—this was done for clarity's sake, and it will be understood by one of skill in the art that the methods discussed herein for decorating nucleic acids of the invention will produce decorated nucleic acids comprising probes on both strands.

In certain embodiments, the hybridization reactions will be conducted under conditions such that only probes capable of ligation will remain hybridized to the target nucleic acid. Thus, probes hybridizing in configurations illustrated in FIGS. 4B-D would not remain hybridized to the nucleic acid and would not be part of the final decorated nucleic acid generated using this method of the invention.

In embodiments in which not all of the single stranded regions are repaired using polymerase and nucleotides with the optional addition of a ligase, the overall stability of the nucleic acid can be increased using known methods, including crosslinking one or more positions along the length of the nucleic acid to stabilize the overall structure. However, such measures may not be necessary, because generally the double stranded regions will be of far greater length than the single stranded regions generated as described herein, and the double stranded regions will serve to provide enough stability for downstream uses of the decorated nucleic acids. In one embodiment, single stranded gaps remaining in the substantially double stranded decorated nucleic acid will comprise less than 20%, 15%, 10%, 5%, 3%, or 1% of all bases in the entire decorated nucleic acid.

The frequency at which probes are inserted along a nucleic acid can be estimated statistically, partly based on size of the probes. Other factors influencing this frequency are reaction conditions, including the temperature at which the nicking-gap-hybridization reactions are conducted. For full coverage of a genome, generally 1024 reactions—each including a sufficient number of target fragments from the same sample—can be reacted with four hexamer probes. In one embodiment, the target fragments have overlapping sequences, thus providing multiple reads for each base of the target nucleic acid.

An optimal concentration of enzymes and probes can be determined such that the number of molecules of exonuclease, polymerase and ligase matches the number of non-repaired gaps. An exemplary combination of enzymes includes Nt.CviPII (↓CCD) nicking enzyme (NEB), which recognizes a 3-base sequence of nucleotides and cuts each strand at every ~25 bases; ExoIII nuclease, which cuts several bases per binding event; and Klenow fragment of DNA polymerase I, which does not have 5'-3' or 3'-5' exonucleotide or strand displacement activity (Derbyshire et al, 1988) can be used. The Nt.CviPII enzyme activity varies from 25% to 100% when different buffers are used. Modification of reaction conditions or engineering of the enzyme active site may further increase the nicking frequency 2-4 fold. Similarly, temperature, salt concentration and the ratio of enzyme to DNA greatly affect ExoIII enzyme activity. In addition, enzymes with different binding or preference sequences can be used to further control and modify the process of decorating a nucleic acid. For example, DNAse I nicks each DNA strand independently with preference for some sequences. Thus, reaction conditions, including buffers, temperatures, and reactant concentrations, can all be modified in the process of decorating a nucleic acid to optimize the hybridization of probes and any subsequent repair steps.

In a further embodiment, a plurality of nucleic acids undergoing the decoration method outlined above are separated into different aliquots at some point before the labeled probes are added to the gapped nucleic acids. This aliquoting may be done before the nicking enzyme is applied, before the exonuclease is applied, and/or before the labeled probes are added. Different sets of probes can be applied to the different aliquots, thus generating decorated nucleic acids with overlapping sequences that are decorated with different sets of probes. Determining the order of the labels on the decorated nucleic acids from the different aliquots thus provides a greater amount of sequence information that can then be assembled using methods known in the art and described herein to provide sequences of larger target nucleic acids, including whole human genomes.

In a further embodiment, when different sets of probes are used, each set will generally comprise probes with probe sequences that are different from the probe sequences of the other sets. Each probe sequence within a set will also generally comprise a unique label.

Decoration Using Invasive Labeled Probes

In one aspect, double stranded nucleic acids are decorated through the use of invasive probes. By "invasive probe" is meant a probe that is able to enter a double stranded nucleic acid and hybridize to a complementary sequence on one of the strands, creating a "D-loop" within the structure of the nucleic acid. Such invasive probes are generally associated with recombinases. In the present invention, recombinase refers to a family of RecA-like recombination proteins all having essentially all or most of the same functions, particularly: (i) the recombinase protein's ability to property bind to and position targeting polynucleotides (also referred to herein as invasive probes) on their homologous targets and (ii) the ability of recombinase protein/targeting polynucleotide complexes to efficiently find and bind to complementary endogenous sequences. The best characterized recA protein is from *E. coli*, in addition to the wild-type protein a number of mutant recA-like proteins have been identified (e.g., recA803; see Madiraju et al., PNAS USA 85(18):6592 (1988); Madiraju et al, Biochem. 31:10529 (1992); Lavery et al., J. Biol. Chem. 267:20648 (1992)). Further, many organisms have recA-like recombinases with strand-transfer activities (e.g., Fugisawa et al., (1985) Nucl. Acids Res. 13: 7473; Hsieh et al., (1986) Cell 44: 885; Hsieh et al., (1989) J. Biol. Chem. 2: 5089; Fishel et al., (1988) Proc. Natl. Acad. Sci. (USA) 85: 3683; Cassuto et al., (1987) Mol. Gen. Genet. 208: 10; Ganea et al., (1987) Mol. Cell. Biol. 7: 3124; Moore et al., (1990) J. Biol. Chem. 19: 11108; Keene et al., (1984) Nucl. Acids Res. 12: 3057; Kimeic, (1984) Cold Spring Harbor Symp. 48: 675; Kmeic, (1986) Cell 44: 545; Kolodner et al., (1987) Proc. Natl. Acad. Sci. USA 84: 5560; Sugino et al., (1985) Proc. Natl. Acad. Sci. USA 85: 3683; Halbrook et al., (1989) J. Biol. Chem. 264: 21403; Eisen et al., (1988) Proc. Natl. Acad. Sci. USA 85: 7481; McCarthy et al., (1988) Proc. Natl. Acad. Sci. USA 85: 5854; Lowenhaupt et al., (1989) J. Biol. Chem. 264: 20568, all of which are hereby incorporated herein by reference in their entirety for all purposes and in particular for their teachings related to recA. Examples of such recombinase proteins include, for example but not limitation: recA, recA803, uvsX, and other recA mutants and reca-like recombinases (Roca, A. I. (1990) Crit. Rev. Biochem. Molec. Biol. 25: 415), sep1 (Kolodner et al. (1987) Proc. Natl. Acad. Sci. (U.S.A.) 84:5560; Tishkoff et al. Molec. Cell. Biol. 11:2593), RuvC (Dunderdale et al. (1991) Nature 354: 506), DST2, KEM1, XRN1 (Dykstra et al. (1991) Molec. Cell. Biol. 11:2583), STP.alpha./DST1 (Clark et al. (1991) Molec. Cell. Biol. 11:2576), HPP-1 (Moore et al. (1991) Proc. Natl. Acad. Sci. (U.S.A.) 88:9067), other target recombinases (Bishop et al. (1992) Cell 69: 439; Shinohara et al. (1992) Cell 69: 457); incorporated herein by reference. RecA may be purified from *E. coli* strains, such as *E. coli* strains JC12772 and JC15369 (available from A. J. Clark and M. Madiraju, University of California-Berkeley, or purchased commercially). These strains contain the recA coding sequences on a "runaway" replicating plasmid vector present at a high copy numbers per cell. The recA803 protein is a high-activity mutant of wild-type reca. The art teaches several examples of recombinase proteins, for example, from *Drosophila*, yeast, plant, human, and non-human mammalian cells, including proteins with biological properties similar to recA (i.e., recA-like recombinases), such as Rad51 from mammals and yeast, and Pk-rec (see Rashid et al., Nucleic Acid Res. 25(4):719 (1997), hereby incorporated by reference). In addition, the recombinase used with invasive probes of the invention may actually be a complex of proteins, i.e. a "recombinosome". In addition, included within the definition of a recombinase are portions or fragments of recombinases which retain recombinase biological activity, as well as variants or mutants of wild-type recombinases which retain biological activity, such as the *E. coli* recA803 mutant with enhanced recombinase activity. In a preferred embodiment, recA or rad51 is used. For example, recA protein is typically obtained from bacterial strains that overproduce the protein: wild-type *E. coli* recA protein and mutant recA803 protein may be purified from such strains. Alternatively, recA protein can also be purchased from, for example, Pharmacia (Piscataway, N.J.). RecA proteins, and its homologs, form a nucleoprotein filament when it coats a single-stranded DNA. In this nucleoprotein filament, one monomer of recA protein is bound to about 3 nucleotides. This property of recA to coat single-stranded DNA is essentially sequence independent, although particular sequences favor initial loading of recA onto a polynucleotide (e.g., nucleation sequences). The nucleoprotein filament(s) can be formed on essentially any DNA molecule and can be formed in cells (e.g., mammalian cells), forming complexes with both single-stranded and double-stranded DNA, although the loading conditions for dsDNA are somewhat different than for ssDNA.

The conditions used to coat targeting polynucleotides with recombinases such as recA protein are known in the art, see e.g., U.S. Pat. Nos. 5,273,881 and 5,223,414, each incorporated herein in its entirety for all purposes and in particular for all teachings related to recombinases such as recA.

In one aspect, decorated nucleic acids of the invention are formed by adding a first set of recA invasive labeled probes to the double stranded nucleic acid to form D-loops within the double stranded nucleic acid, thus forming a decorated nucleic acid. In this aspect of the invention, the recA invasive labeled probes comprise a plurality of non-overlapping probe sequence and each probe sequence comprises a unique label. Such probes hybridize to sequences in the double stranded nucleic acid that are complementary to the probe sequences.

In a further embodiment, a second set of recA invasive probes is added to the double stranded nucleic acid to form double D-loops within the double stranded nucleic acid. In such an embodiment, the second set of recA invasive labeled probes are substantially complementary to the first set of recA invasive labeled probes. In one exemplary embodiment, both sets of probes may be labeled with the same color to increase fluorescence signal for each loop. In another exemplary embodiment, the two sets of invasive probes are labeled with different colors as a kind of internal control. When detecting the presence of the probes using methods known in the art and described further below, detecting both colors provides a higher confidence value that the sequence represented by that probe is in fact present in the target nucleic than if only one color is seen.

In a still further embodiment, recA invasive labeled probes used in accordance with the invention comprise at least one modification selected from: locked nucleic acid, peptide nucleic acid and phosphorothioate nucleic acid. Such modifications can often serve to strengthen the hybridization of these probes with their complementary sequences than is possible with naturally occurring nucleic acids.

In one embodiment, after a D-loop or double D-loop is formed as described above, a polymerase extends the invasive probes until dideoxy is incorporated. Incorporation of dideoxy can help increase the stability of the resultant decorated nucleic acid molecules.

In a further embodiment, the hybridized invasive probes are extended using a polymerase. This extension of the probes serves to stabilize the invasive probes and prevent the D-loop or the double D-loop from destabilizing the probes and causing them to detach from the nucleic acid. This extension is particularly useful in methods utilizing shorter probes (for example, probes of about 3-4 nucleotides in length).

Invasive labeled probes may comprise any of the structural aspects described above for probes of use in the invention, although generally recA invasive labeled probes will be of shorter length than probes used in other methods described herein for decorating nucleic acids.

Hybridization Conditions

A variety of hybridization conditions may be used to decorate nucleic acids in accordance with the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of helix destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

Using Sets of Probes

In order to use decorated nucleic acids in applications such as sequencing and detection of target sequences, different combinations of sets of probes may be used to decorate nucleic acids in accordance with the present invention. In an exemplary embodiment, probes that comprise oligonucleotides having every possible sequence for the defined length of probes in the set may be used. For example, if a set contains probes of length six, then it contains 4096 ($=4^6$) probes. In such an embodiment, the sets may be divided into subsets that are used together in pools, as discussed in U.S. Pat. No. 6,864,052, which is hereby incorporated by reference in its entirety for all purposes an in particular for all teachings related to using sets of probes.

Probes from different sets may be hybridized to target sequences either simultaneously or sequentially. Probes from different sets may be hybridized as entire sets or as subsets, or pools. In one embodiment, lengths of probes in different sets are in the range of from about 3 to about 20 nucleotides. In a further embodiment, lengths of probes in different sets are in the range of from about 4 to about 18, about 5 to about 14, about 6 to about 12, about 7 to about 10 and about 8 to about 9 nucleotides. In a further aspect, probes from different sets will hybridize to adjacent positions on a target nucleic acid, and in some embodiments, these adjacently hybridized probes can be ligated, forming ligation products of lengths from about 6 to about 40 nucleotides.

IIID. Stretching

The present invention provides methods of forming stretched decorated nucleic acids. In one aspect, decorated nucleic acids are stretched by applying them to substrates. Substrates of use in the present invention are described in further detail above.

One advantage to the methods of forming decorated nucleic acids in accordance with the methods described above is that these molecules are often more flexible than naturally occurring nucleic acids but nevertheless retain enough stability to withstand the process of being "stretched". This combination of flexibility and strength is of particular use with substrates comprising nanostructures such as nanochannels.

In one aspect, decorated nucleic acids of the invention are stretched by applying them to nanochannels.

In another aspect, decorated nucleic acids of the invention are stretched by applying them to flowthrough systems. As described further above, flowthrough systems of the invention include a planar surface with alternating hydrophobic and hydrophilic regions. In a further embodiment, the alternating hydrophobic and hydrophilic regions are in a linear pattern.

As discussed above, in some embodiments, methods of the invention can be used to generate a plurality of different decorated nucleic acids. In one embodiment, each of a plurality of different nucleic acids can be applied to a single substrate, for example to a single nanochannel or a single lane of a flowthrough system. In such an embodiment, the different decorated nucleic acids can be applied to the substrate sequentially, thus allowing sequence information from each one to be obtained in turn. In a further embodiment, the plurality of different decorated nucleic acids are applied to a plurality of substrates, either singly or in groups. For example, an assembly comprising multiple nanochannels may be used, or a flowthrough system comprising multiple lanes. This embodiment increases the number of decorated nucleic acids that can be analyzed at once, thus allowing such analyses to be scaled up to high density high throughput applications.

In one aspect of the invention, double stranded decorated nucleic acids of the invention are applied to a nanostructure (e.g., a nanochannel or a nanopore) to remove one strand and to stretch the molecule, thus providing a stretched single-stranded decorated nucleic acid. The narrow nanostructures prevent banding and formation of intra-strand hairpin type secondary structures. In a further aspect, double stranded decorated nucleic acids are denatured to form single stranded molecules, and then those single stranded molecules are applied to the nanostructures or other substrates described in further detail above.

Both double stranded and single stranded decorated nucleic acids can be analyzed for sequence information in accordance with the present invention as described more fully below.

IV. Methods of Using Compositions of the Invention

The present invention provides methods of using compositions comprising substrates with stretched decorated nucleic acids.

In one aspect, the compositions of the invention are used to determine the sequence of a target nucleic acid. By "target nucleic acid" is meant a nucleic acid of interest. The term "sequence of a target nucleic acid" (also referred to herein as the "target sequence") refers to a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the target sequence may take many forms. For example, it may be contained within a larger nucleic acid sequence, i.e. all or part of a gene or mRNA, a restriction fragment of a plasmid or genomic DNA, among others. As is outlined more fully herein, probes are designed to hybridize to target sequences to determine the presence or absence of the target sequence in a sample.

In further aspects, compositions of the invention are used in to de novo sequencing or resequencing applications. De novo sequencing is the initial sequencing that results in the primary genetic sequence of organisms. A detailed genetic analysis of an organism is possible only after de novo sequencing has been performed. Resequencing involves detecting target sequences, for example for candidate genes or other genomic regions of interest, in a sample. Such resequencing applications are a key step in detection of mutations associated with various congenital diseases. Resequencing techniques can be divided into those which test for known mutations (genotyping) and those which scan for any mutation in a given target region (variation analysis). Typical mutations being tested are single nucleotide polymorphisms (SNP), insertion and deletion mutations.

IVA. Detection of Probes on Stretched Decorated Nucleic Acids

In one aspect, the present invention provides methods of using compositions comprising substrates with stretched decorated nucleic acids. As discussed herein, in one exemplary aspect, compositions of the invention are used to determine the sequence of a nucleic acid or detect a target sequence. In one aspect, the present invention provides methods for analyzing single molecule genome segments of 100,000 base pairs or longer to be analyzed at a rate of 1 billion raw base pairs per minute with an output accuracy of greater than 99.99%.

The present invention provides methods of detecting the probes incorporated into stretched decorated nucleic acids. Since these probes are generally associated with a specific sequence, identification of a particular probe on a stretched decorated nucleic acid provides sequence information about that nucleic acid.

Methods for detecting probes associated with nucleic acids are known in the art. Such methods often involve multicolor imaging systems. In one aspect of the invention, hardware is provided to allow detection of decorated nucleic acids of the invention. In one embodiment, the system hardware comprises three major components; the illumination system, the reaction chamber, and the detector system. The detection instrument can include several features such as: adjustable laser power, electronic shutter, auto focus, and operating software.

Signals from decorated nucleic acids of the invention can be detected by a number of detection systems, including, but not limited to, scanning electron microscopy, near field scanning optical microscopy (NSOM), total internal reflection fluorescence microscopy (TIRFM), and the like. Abundant guidance is found in the literature for applying such techniques for analyzing and detecting nanoscale structures on surfaces, as evidenced by the following references that are incorporated by reference: Reimer et al, editors, Scanning Electron Microscopy: Physics of Image Formation and Microanalysis, $2^{nd}$ Edition (Springer, 1998); Nie et al, Anal. Chem., 78: 1528-1534 (2006); Hecht et al, Journal Chemical Physics, 112: 7761-7774 (2000); Zhu et al, editors, Near-Field Optics: Principles and Applications (World Scientific Publishing, Singapore, 1999); Drmanac, International patent publication WO 2004/076683; Lehr et al, Anal. Chem., 75: 2414-2420 (2003); Neuschafer et al, Biosensors & Bioelectronics, 18: 489-497 (2003); Neuschafer et al, U.S. Pat. No. 6,289,144; and the like. Of particular interest is TIRFM, for example, as disclosed by Neuschafer et al, U.S. Pat. No. 6,289,144; Lehr et al (cited above); and Drmanac, International patent publication WO 2004/076683.

As discussed in further detail above, decorated nucleic acids of the invention can in some aspects be stretched in nanochannels. Signals from nucleic acids in such nanochannels can be detected using any of the methods discussed above. In one embodiment, signals from stretched decorated nucleic acids in nanochannels are detected using scanning electron microscopy. Similarly, decorated nucleic acids stretched in flowthrough systems discussed herein can also be detected using any of the methods discussed above.

The simplest commercially available probe labeling scheme is to use single dye molecules. In one embodiment, a washing step is included in the process to ensure that almost all probe molecules that are not hybridized to the target nucleic acid are removed. In one embodiment, four dyes are used to label probe molecules. In an exemplary embodiment, dyes used are commercially available, such as the dyes in the "BigDye®" sequencing kits available from Applied Biosystems. Such dyes generally combine a donor and one acceptor. The same donor is used in all four dyes, and each different dye has a different acceptor that generates a different emission wave length after illumination of the donor. These dyes are bright and a single excitation wave length is generally sufficient for all four dyes. Detection of a single dye molecule in stretched DNA can be obtained with sensitive CCD cameras.

In one embodiment, FRET is used for detecting probes in decorated nucleic acids of the invention. FRET detects only an acceptor dye that is <10 nm from donor dye. As discussed above, in some aspects of the invention, two probes will hybridize to adjacent positions of a target nucleic acid, and in some further aspects will ligate. Such adjacent probes are ideally suited for FRET detection. For example, probes of ~3 nm in size that are adjacent to each other will provide a FRET-tolerated distance of ~6 nm (or another multiplier of 3 if additional probes are used). Standard FRET will generally require that the probes used in the invention be labeled with pairs of existing proven dye molecules such as Cy3/Cy5. Various designs (length and sequences of arms) for probes of use in FRET detection methods will be apparent to one skilled in the art upon reading the present disclosure, and it is envisioned that many such designs can be used in the claimed invention provided such structures provide good energy transfer without impairing probe ligation.

In one embodiment, molecular antennae are used with FRET detection methods. As discussed above, these light harvesting polymers can provide a 10-fold higher light yield than regular fluorophores, increasing the accuracy of any method used to detect probes on decorated nucleic acids of the invention. In this embodiment of the invention, oligonucleotide probes are labeled with one or more fluorescent dye molecules. These probes are used to decorate nucleic acids using methods described herein. Light harvesting polymers are then applied to the decorated nucleic acids. Light harvesting polymers that attach to the hybridized probes will bring the molecules in close enough proximity to allow the Forster energy transfer (FRET) to occur between the cationic-conjugated polymer and the dye on the probe. This energy transfer results in the light emitted by the complex to change from the blue emission of the light harvesting polymers on their own to the green light emitted by the fluorescent dye. The ability of the light harvesting polymers to collect a large number of photons results in increased energy for transfer to the dye on the probe, thus boosting the resultant signal. In a further embodiment, the dye-labeled probes comprise PNA.

In one embodiment, stretched decorated nucleic acids on a substrate will be treated such that the hybridized probes will detach from the nucleic acids and then the same or different probes will hybridize to the same location on the nucleic acid. For example, temperature changes (i.e., "melting" the hybridized probes off of the nucleic acid) or changes in pH or ionic strength can be used to destabilize the probes decorating a nucleic acid such that they detach from the nucleic acid. If the nucleic acid is contained in a relatively confined system, such as a nanochannel or the substrates comprising linear features described above, pools of probes can be washed over the nucleic acid, such that probes again hybridize to the same location of the nucleic acid. This embodiment is particularly amenable to nucleic acids that are decorated by generating single stranded gaps in a double stranded nucleic acid through some combination of nicking and exonuclease enzymes (such methods are described in further detail above in the section entitled "Methods of making compositions of the invention").

IVB. Detection of "Sequence Signatures"

Stretched decorated nucleic acids of the invention can be used to obtain sequence information of a target nucleic acid. In one aspect, the sequence of target nucleic acids are obtained by cumulative detection of labeled probes on decorated nucleic acids of the invention.

In a further aspect, decorated nucleic acids comprising a plurality of probes are analyzed for their sequence signatures. By "sequence signature" is meant a pattern of probe decoration that is in general different for different nucleic acids. As discussed above, decorated nucleic acids of the invention are generally produced through a stochastic process in which probes are incorporated into the structure of the nucleic acid at random intervals along the length of that nucleic acid. These stochastic processes thus generate a different order and relative distance of probes in different nucleic acids. Detection of the pattern of these probes for each individual nucleic aid provides the sequence signature for that nucleic acid.

In some embodiments, a signature comprises about 4 probes. In further embodiments, signatures comprise about 8, 12, 16, 24, 32, 36 or more probes.

In a further aspect, sequence signatures of individual decorated nucleic acids are combined to assemble larger sequences, including entire genome sequences. In an exemplary aspect, sequence signatures are used to provide a genomic "map" of probe identities. This map can be processed to identify the sequences represented by the probes. When assembling larger sequences, either the maps of probes or the sequences represented by those probes can be assembled to generate the larger sequences.

In a still further aspect, a single signature type is used for each nucleic acid within an entire sample. In another aspect, multiple independent signatures are determined for a portion of a sample and used as a "representative set" of the sample. Detecting multiple independent signatures on a representative number of nucleic acid fragments can thus be used to test an entire sample.

In one aspect, the present invention provides methods for extracting accurate sequence signatures within the context of a high density imaging environment and to distinguish the actual signature from background noise.

In a further aspect, signatures are generated from multiple images of stretched decorated nucleic acids of the invention. In a still further aspect, signatures are obtained from data on probe binding "intensity". The data used to assemble a unique signature for each nucleic acid corresponds to the number of distinguishing probe features that can be used to identify the presence of each individual probe. For example, in a case where four different probes are used, each linked to a different fluorescent marker identifiable by its color, four different images or intensity graphs would be taken for each decorated nucleic acid (one for each color).

If multiple images are used to generate sequence signatures, the multiple images must be carefully aligned so that there is no significant offset between the images. In one aspect, this is accomplished by utilizing fiducials to ensure that each image is aligned with each previous image. Another way to ensure that multiple images are aligned is by taking each of the images at the same position, for example, by changing filters or by using multiple cameras. Cameras can be adjusted at the beginning of the imaging process to best align with the substrate on which the decorated nucleic acids are stretched and to take into account the pixels of the imaging device. If multiple cycles are performed on the same stretched decorated nucleic acids, the signatures from consecutive cycles can be used independently or can be combined to provide further specificity.

In one aspect, the signature of each nucleic acid molecule is generated by identifying the presence or absence of specific probes in consecutive resolution segments of the individual molecules. By "resolution segment" is meant a distance with a predefined accuracy in ordering neighboring probe matches. This predefined accuracy will generally be about 90%, but may be higher or lower. If matching sites for two probes are within the resolution limits of the imaging or other detection system used for identification of a probe, the sequence signature can be generated by identification and ordering of these probes on the stretched decorated nucleic acid within each resolution unit. This type of signature is particularly useful if probe matching sites on the nucleic acid are infrequent relative to optical resolution of the probes. For example, starting from the first positive probe a signature would be determined as follows:

sequence signatures created using the information of genomic sequence data from multiple sources. In further embodiment, the sequence signatures are compared to a defined set of signatures created from empirical observation.

In one exemplary embodiment, simple signatures (in which no distance information is included) made of 4 different 6-mers are identified that have a frequency in single stranded DNA of 1 in $4^P$, where P is the number of positions in the signature. Signatures generated on dsDNA can be equivalent to using 8 different probes if the probes recognizing complementary DNA sequences are labeled the same way; for example labeled with the same fluorescent dye.

Figures 11A, 11B, 11C:
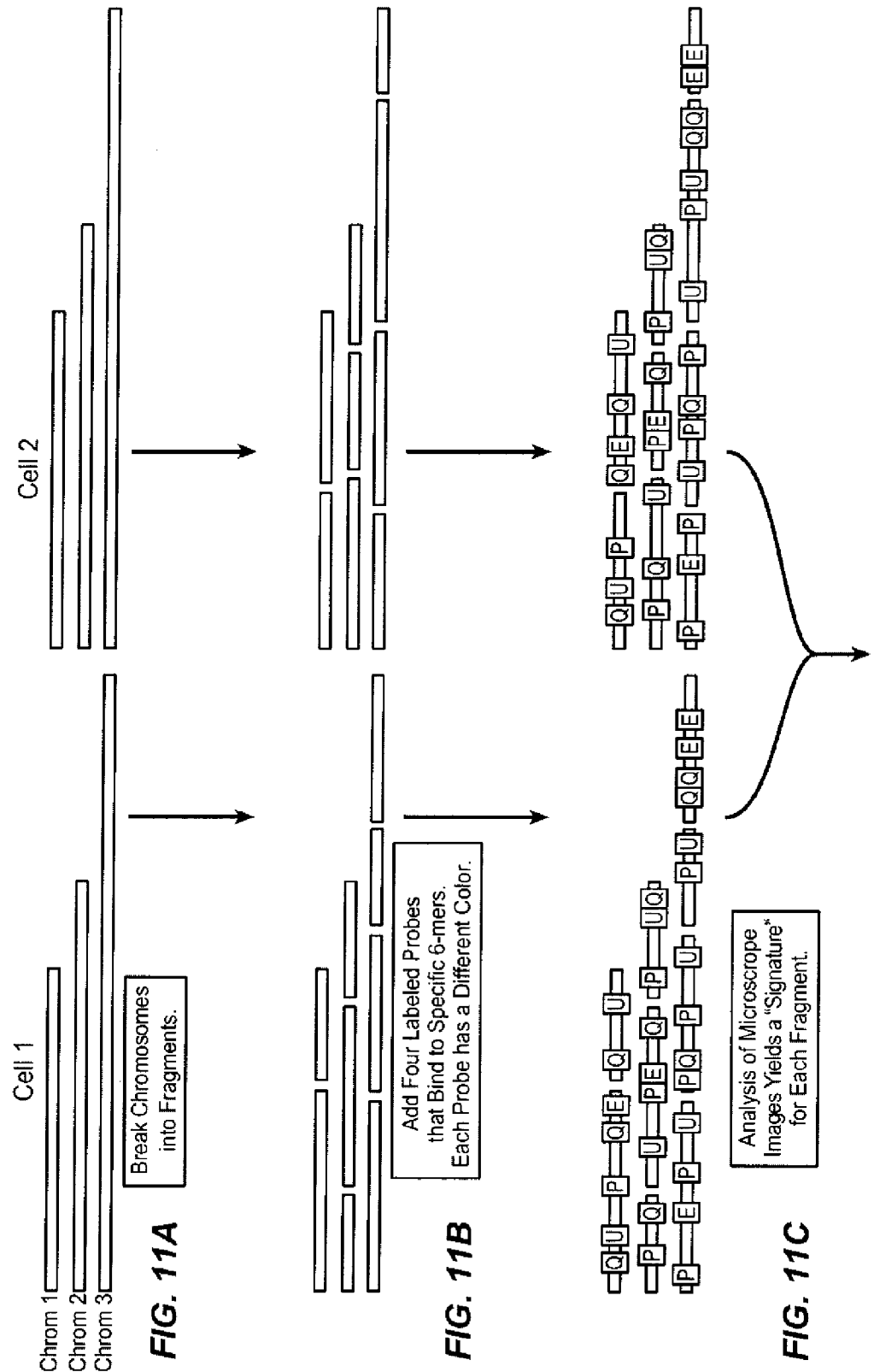
FIG. 11A shows the multiple chromosomes that can be fragmented to form the fragments in FIG. 11B. These fragments are labeled with probes that bind to specific 6-mers (FIG. 11C) to form decorated fragments. The order of the probes along each fragment provides a signature for each fragment (FIG. 11D). The signatures can then be aligned based on probe pattern and length of fragment to reconstruct chromosomes. The chromosomal sequences can then be constructed by aligning signatures based on probe pattern and length (FIG. 11E).
Figures 11D, 11E:
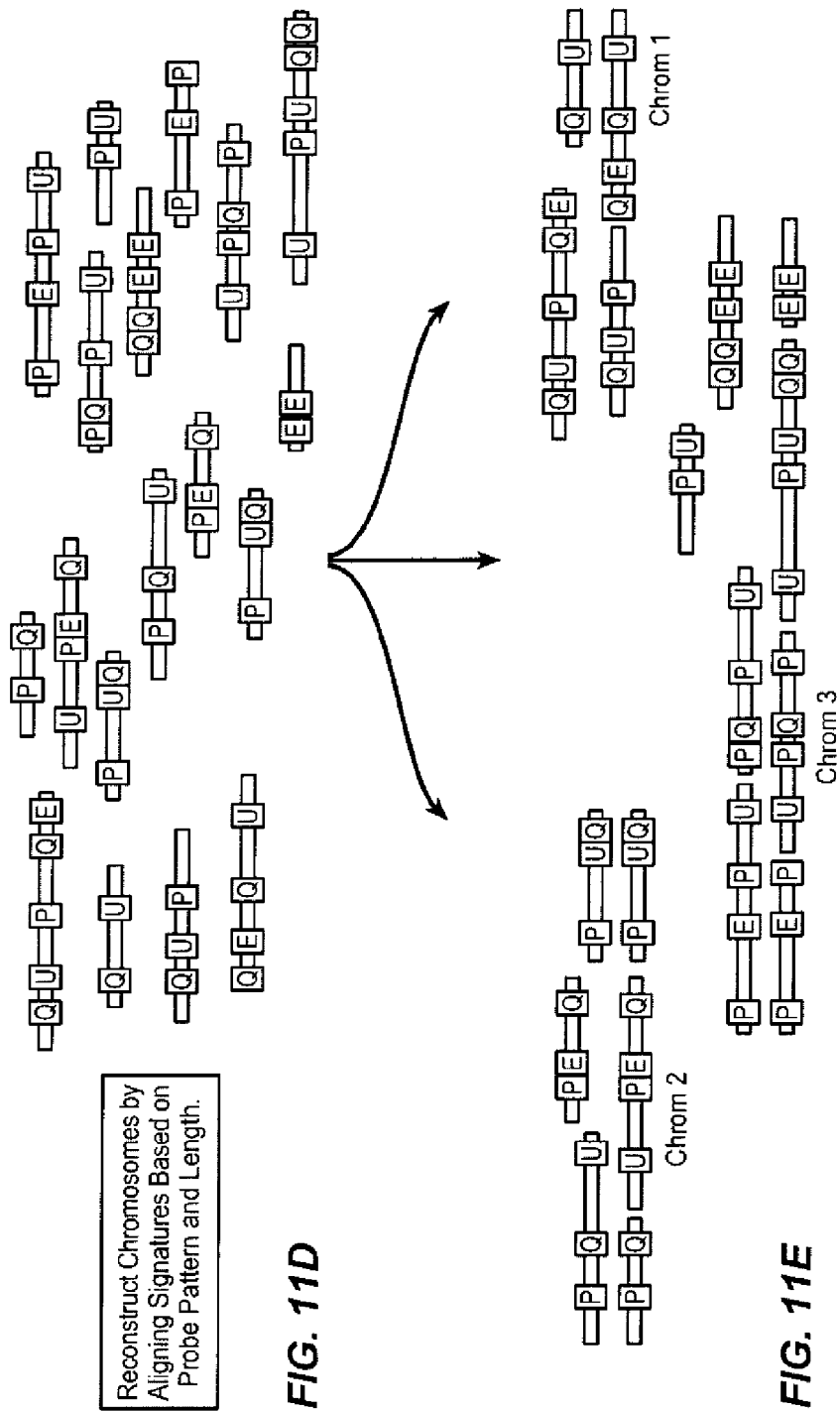
FIG. 11 is a schematic illustration of assembling fragments to construct a map of chromosome molecules.

In one embodiment, chromosomal sequences are assembled de novo using sequence signatures obtained from fragments. An exemplary embodiment is illustrated in FIG. 11. As shown, chromosomes from two different cells are broken into fragments. Four differentially labeled probes (identified by the letters Q, U, P, and E in FIG. 11) are added. Each probe will bind to a specific sequence. Analysis of images taken from each fragment will provide a "signature" for each fragment. The chromosomal sequences can then be constructed by aligning signatures based on probe pattern and length (FIG. 11E).

Figure 10C:
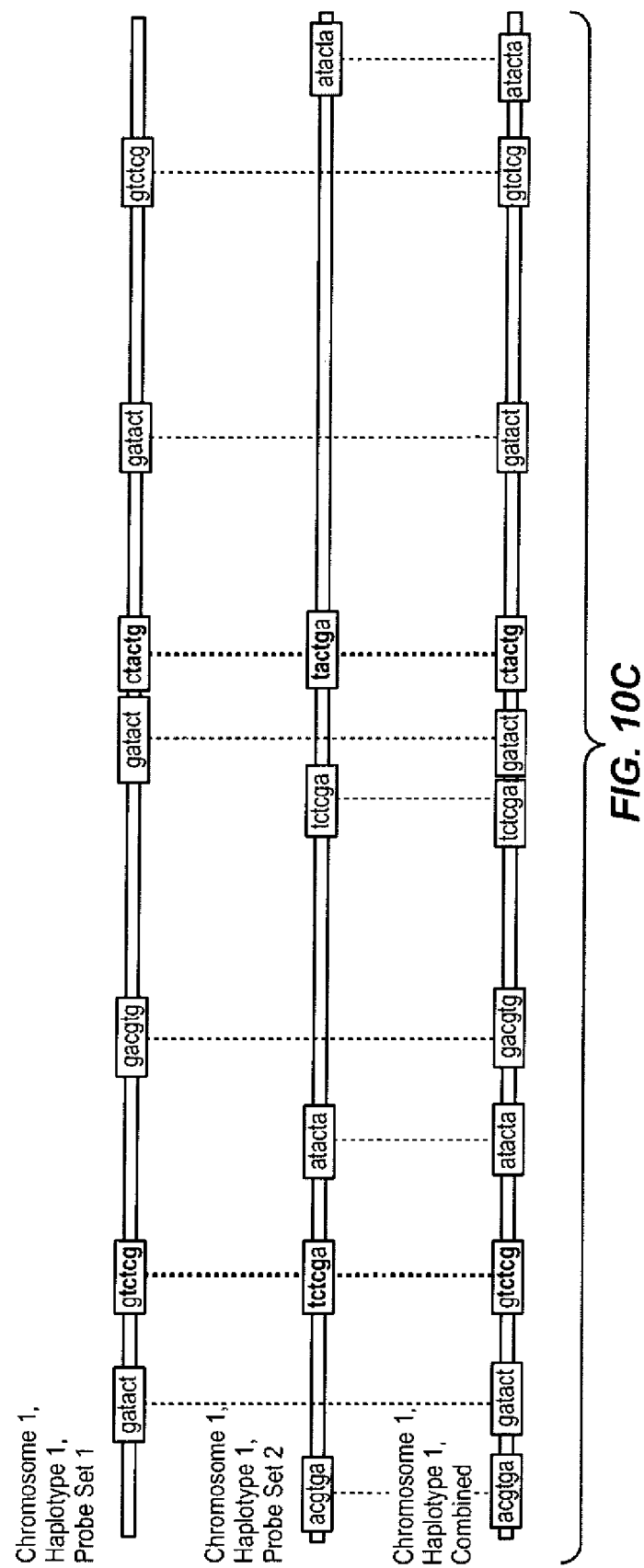
FIG. 10 is a schematic illustration of converting consensus signatures into partial chromosome sequences. The order of probes detected along a fragment (FIG. 10A) provide a map of the sequences represented by those probes. This can be accomplished for multiple probe sets (FIGS. 10A and 10B). Detection of probes to identify sequences can be repeated to cover all possible 6-mers on double stranded DNA. The partial sequences obtained from each of the repetitions can be assembled to provide the partial chromosome sequence (FIG. 10C).
Figure 12:
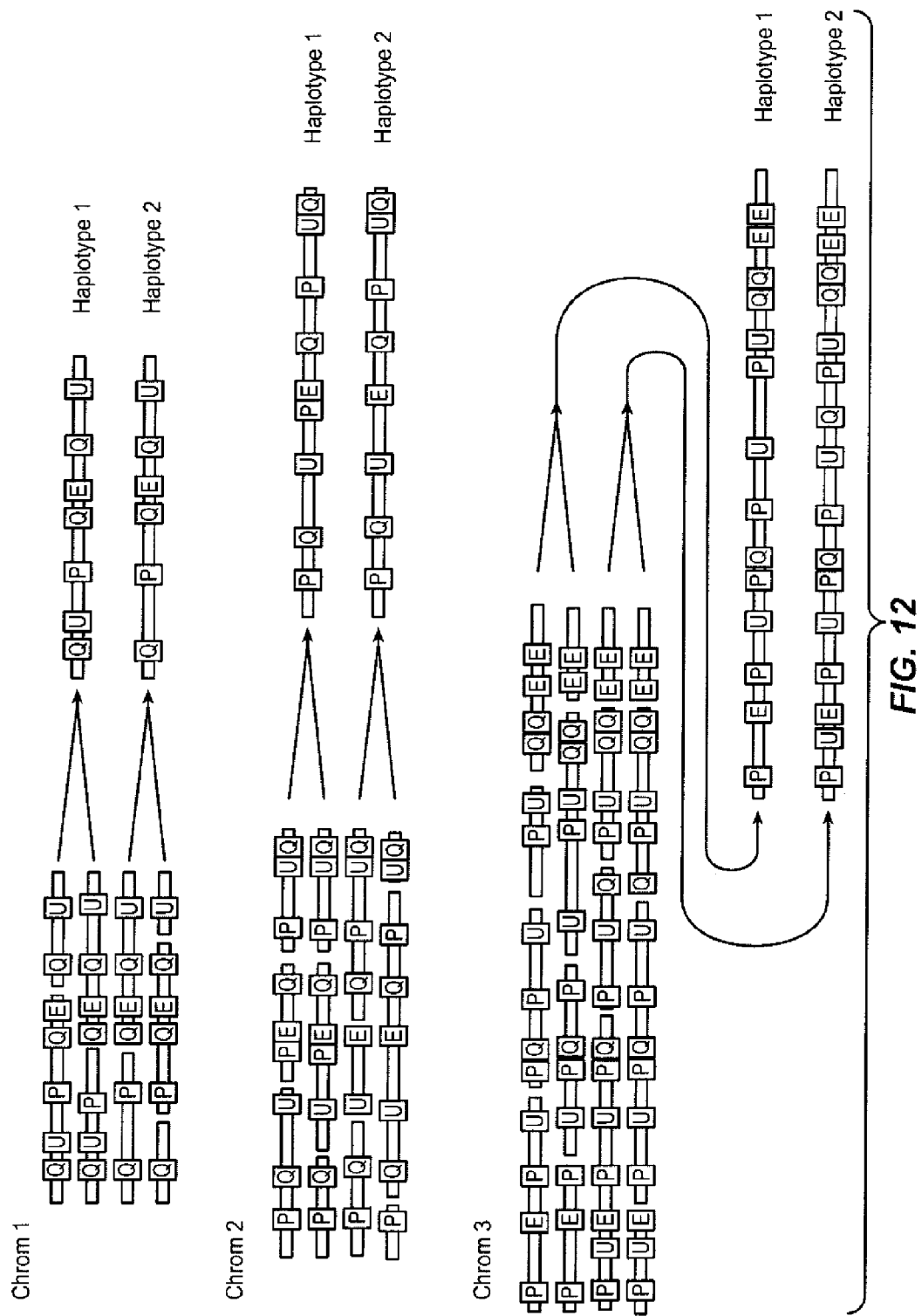
FIG. 12 is a schematic illustration of assembling consensus signatures for each haplotype chromosome. Three different chromosomes are illustrated.

In a further embodiment, consensus signatures can be converted into partial or complete chromosomal sequences. An exemplary embodiment is illustrated in FIG. 10. Although in this embodiment, two probe sets are illustrated, it will be appreciated that multiple probe sets can be used. Each probe set comprises four differentially labeled probes, and each probe within each set has a unique probe sequence. The partial sequences obtained from each of the probe sets can be combined to provide the chromosomal sequence (see FIG. 10C). FIG. 12 illustrates a further embodiment in which consensus signatures for each haplotype chromosome are assembled from the signatures obtained from the fragments.

| | Res. unit | | | | | |
|---|---|---|---|---|---|---|
| | 1 | 2 | 3 | 4 | 99 | 100 |
| Fragment 1: | BBBBBB2 - | BBBBBB3 - | OOOOOO - | BBBBBB2 | ... BBBBBB1 - | BBBBBB4 |
| Fragment 2: | BBBBBB4 - | BBBBBB1 - | BBBBBB3 - | OOOOOO | ... BBBBBB2 - | OOOOOO | where OOOOOO represents the absence of hybridization of a probe within a particular resolution unit.

A resolution unit is expressed in number of bases, such as 500 bases. A signature generated in this way can capture information about multiple occurrences of the same probe within one resolution unit. Experimentally that information can be obtained as double and triple fluorescence intensity. Additional information can also be obtained by measuring the distances more precisely, e.g., using data generated every 2.5 resolution units rather than every 3 resolution units.

Assembling Sequence Signatures Using Reference Tables

Once the signatures have been obtained for a sufficient number of individual nucleic acid molecules or a sufficient number of nucleic acid fragments in the form of clonal clusters, the signatures can be mapped (aligned) to one or more genomic reference sequences. The mapping approach used should accommodate the possibility of large numbers of missing probe binding scores and/or rare unexpected mutation reading probes or false positive scores. Furthermore, the mapping approach should allow proper mapping signatures for segments of 100 kb due to DNA rearrangements. In one embodiment, a high mapping speed is used to match the reader output of about 100,000 or more signatures per second (1 $e^9$ or more signatures in approximately 3 hours).

In one embodiment, sequence signatures are mapped to an informative reference table of genome locations of individual From a statistical point of view, signatures for a 100 kb fragment of dsDNA that have 200 matching positions of 4 different 6-mers have a frequency in nucleic acid sequence equivalent of a 200-base contiguous sequence, e.g., these signatures have no practical chance to match other than the true site in the human genome.

Due to the potential presence of gross genetic alterations (e.g., long deletions, duplications, inversions or translocations), 5-20 kb segments of each 100 kb fragment can be mapped separately to the reference genomes to ensure sequence integrity. A signature representing a 100 kb fragment can be subdivided into twenty ~15 kb segments that are overlapped by 10 kb. Even shorter fragments such as fifty 4-6 kb segments starting at every 2 kb may be used to find matching segments in the presence of 10-20% of errors. These short signatures have low frequency of matching genomic sequences by chance, as such signatures occur extremely rarely in genomic sequence (e.g., the human genome, which has only 6 million possible signatures created from 4 different 6-mers on dsDNA). Shorter signatures of 4 kb would give 2 positive out of 8 sites, with frequency of once in $28^4$=~0.6 million will have ten occurrences per genome.

For example, when four 6-mer resolution unit signatures are generated on dsDNA, a 6 kb segment will have approximately twelve positive probe binding sites. If each probe has three positive binding sites out of twelve possible sites (500- base resolution units), there are $12!/3!\times 9! = 12\times 11\times 10/6 = 220$ possible combinations of probe signatures for the 6 kb segment. Thus, the complete signature of four probes will have the occurrence frequency once in $220\times 220\times 220\times 220 = \sim 16e^8$; or approximately once in one billion such signatures. Even these short signatures have low frequency of matching human genome by chance, and such signatures occur mostly only once in the human genome that has only six million possible signatures created from 4 different 6-mers on dsDNA (one signature starts every 500 bases on average, thus 3 billion/500=6 million). Shorter signatures of 4 kb would give two positive out of eight sites, with frequency of once in $28e^4 = \sim 0.6$ million will have ten occurrences per genome Assembly of sequence data using signatures created by probe hybridization per resolution unit can tolerate a substantial number of false negative or false positive 6-mers. One error on every twelve correctly scored 6-mers (~8% error rate) provides average signature segments of twelve consecutive probes scored without errors. As calculated above, such signatures map uniquely in the human genome and allow unique mapping of longer DNA fragments (having 10-100 such segment signatures) in the presence of mutations or other rearrangements.

Different genomic reference index tables can be created for the different forms of signature, e.g., signatures created using an order of probe sequences, by resolution units, by estimated neighboring distances between probes, etc. An effective way to search signatures of a given number of probes is to generate reference index tables for the entire query region of a nucleic acid, e.g., an entire human genome or a specific sub-set of the human genome. For example, for simple signatures (probe order without any information on distance) created using four different 6-mers that have twelve positions (6 kb DNA segments, on average), a reference table can be created that has 16 million possible signatures ($4^{12}$, i.e., combinations of any of four 6-mers on each of twelve positions on a DNA segment) and for each signature all matching positions are available in the reference sequence table. Because the entire human genome has only 6 million such signatures, about 40% of such signatures will have one matching position in the genome. Genome positions for each signature can be directly found in the reference table by reviewing the index of each given signature. Each signature can be reviewed in the table in both the forward and the reverse orientation.

Experimentally obtained signatures that have more than twelve positive 6-mers due to variation of frequency of given 6-mers or variation in the length of analyzed DNA fragments can be further apportioned into consecutive or a representative number of twelve positive probe sub-signatures. Each such sub-signature is then mapped by finding its matching position in the genome using a reference index table for signatures with twelve positive probes. Each signature is converted to a "12 digit base-4 number" and its genome positions are directly matched in the table at the position (row) corresponding to the same "12 digit base-4 number". This is similar to regular numbers where at each digit position there are 10 possibilities (0 to 9). In this case at each digit position only four numbers are allowed (0 to 3 or 1 to 4), each number corresponding to one of four probes.

Resolution units or estimated distance can also be recorded in the reference index tables. For example, four different resolution units or distances between each of four possible oligo sequences in a given signature can in effect double the length of a signature, compared to determining the signature by direct mapping of the order of oligo sequences only. For example, there are $4^8 = \sim 65,000$ possible 8-mer sites in a simple signature obtained using four probes, but there are $4^{16} = \sim 4$ billion possible signatures providing resolution of four different distances between consecutive probes.

Reference index tables can be generated for matching signatures with deletions (non-scored 6-mers) due to errors in data or mutations in the sequence relative to the reference. For example, signatures of thirteen positive probes can be represented as thirteen signatures having twelve positive probes by deleting one probe at a time (~8% false negative rate). Six million signatures for the entire human genome will generate 78 million positions to be distributed in the reference table that has 16 million possible signatures. 12-probe experimental signature segments can then be checked in this table and cross-referenced to the original table to identify the most likely sequence match. A 100 kb fragment with 10-100 such overlapping signature segments will have a very low chance for false mapping. Longer signatures are generally more unique and can tolerate more missing probe scores. For example, a 15-probe experimental signature segment will find five occurrences in the genome, similarly as in the above example with twelve probe signatures (assuming an 8% missing probe rate).

To address the issue of false positives (1 in 20 matching probes=5%) or probes reading mutations (only one expected in >100 matching probes), experimental signatures can be expanded in sets of shorter signatures by removing one probe at a time. A 16-probe signature can be compared to 15-probe reference table by creating sixteen different 15-probe signatures.

In some embodiments, it may be preferable to perform a simple alignment of a signature within found reference sequences rather than comparison to a larger-scale reference table. Alignment of signatures provides relative positioning (registration) of data from consecutive cycles without need to align images between cycles. This method simplifies instrument engineering and image analysis software.

The computational time required for mapping the 1 billion 100 kb fragments needed to sequence one human genome using the above described reference tables can be estimated. To map each fragment (define ~100 short overlapping segment signatures, find in the reference table ~10 genome occurrences for each segment signature, sort 1000 genome occurrences and define a cluster of 10-50 occurrences within a 20-100 kb genomic segment), about 10,000 computer operations are required including some overhead. For one billion fragments, that is 10,000 billion operations. Four processors running at 1 GHz of effective operations (1 billion operations/second) can perform this calculation in 2,500 seconds (less than 1 hour).

As described herein, the sequence determination process includes detecting probes that are positive within a segment of nucleic acid followed by sequence assembly by compiling overlapped detected sequences. For a 500 base resolution, a long stretched nucleic acid can be envisioned to consist of a series of consecutive 500-base segments, and shifts in these series can be defined based on sequence compilation. Local (within each segment) overlapping probe sequences from all aligned signatures are compiled and the determination value for a reference or a new sequence variant can be calculated.

Each signature is first aligned to the reference sequence according to ~160 matching probes (6 bases read every 500 bases would equal approximately an 80% detection rate). In one embodiment, each signature belongs to a nucleic acid fragment that is about 10 bases shifted from the neighboring fragment. If fragmenting is done by partial digest with a restriction enzyme that cuts frequently, fragments will start approximately every 50 bases, on average, and there will be several fragments starting at that position. Each base is covered by ~10,000 overlapping 100 kb fragments but only a specified number will have probes reading a given base at a particular point.

After mapping each signature, each probe is annotated as matching or not matching to the reference. Each fragment that matches non-continuously to the reference sequence is also annotated to be able to collect a proper subset of probes to assemble break-point sequences. For any genome segment (~1000 bases in length) that has no difference from the reference sequence, each base will be covered with up to 100 overlapping probes coming from different signatures. Even with a 20% false negative rate, about 80 probes (e.g., ~6 overlapped 6-mer probes each scored in multiple overlapping 100 kb fragments) will be annotated as matching the reference sequence and would repeatedly confirm the identity of that base. Some other probes may initially be scored as false positives reading a different base for that position but as soon as their number is small they can be recognized as false scores.

In the case of a single base mutation, probes expected to be positive will not have significant number of occurrences for that region in the data set. For example, unexpected 6-mers that are detected for that 500 base region that are not found to match the reference sequence can be assembled by compiling their mutually overlapped sequence and their overlapping sequences with sequences surrounding the mutation site. This approach defines a bridging mutated sequence. This sequence has to have a significant number of overlapping 6-mers as a confirmation that this is a real sequence.

In the sequencing of a nucleic acid in which there are suspected to be many closely spaced mutations or insertions of a foreign sequence, the bridging sequence provided by the probes may extend from the six overlapping probes in the case of single base mutation to over hundreds or thousands of bases. This type of sequence assembly is known as "local de-novo sequence assembly." Several types of information can be provided to allow efficient de-novo assembly: 1) overlapping 6-mers, 2) order of small groups of 6-mers (the higher the resolution along DNA segments and more fragment ends from the overlapping DNA fragments, the smaller the groups), 3) knowledge of an exact distance between ends of some overlapped fragments that defines an exact length of sequence for a group of probes detected between two fragment ends; 4) knowledge of the fragment end sequence (1-4 bases); and 5) reference sequence match. Integration of these types of information assures unique sequence assembly and determination of the size of simple repeats.

Optimization of algorithms, various software functions and various input parameters can be achieved using simulated data with various quantity and quality measures. The versions of the sequence assembly software in the methods of the invention will be selected to provide completeness, accuracy and speed of the assembly using several standard simulated data sets. Simulated data will be developed with realistic data quality and sequence changes. For the same data set, several different reference sequences and/or reference tables with various changes relative to the sample sequence can be evaluated.

In a further embodiment, the intensity of color detected for a single molecule provides sequence information. The intensity of color can reflect the number of probes present on the molecule. That information can be used in conjunction with the sequence represented by that color (i.e., by the probe) to assist in assembling the sequence.

Tandem repeats can be detected and analyzed by using stretched decorated nucleic acids that are generated from nested fragments. As discussed further above, nested fragments can be produced through successive cycles of restriction enzyme digests. When these consecutive cycles utilize exact cutter type IIs restriction enzymes, identifying the sequence of these fragments will provide sequences that are separated by an exact number of bases. This allows determination of an exact length of tandem repeats such as mono, double and triple repeats that are located between these fragment ends.

IVC. Detection of Target Sequence

In one aspect, decorated nucleic acids of the invention are used to detect the presence of a target sequence in a sample. In this aspect, target nucleic acids obtained from a sample are used to generate stretched decorated nucleic acids of the invention. Such a sample may comprise but is not limited to, cells, tissues, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples; purified samples, such as purified genomic DNA, RNA, proteins, etc.; raw samples (bacteria, virus, genomic DNA, etc.); as well as libraries (such as cDNA libraries generated from mRNA), amplified and synthetic nucleic acids. As will be appreciated, virtually any experimental manipulation may be applied to the sample prior to its use in accordance with methods of the invention. Samples of use in the invention may be obtained from target organisms.

Detection of target sequences in a sample has a number of uses, including pathogen detection and clinical diagnostics. Clinical diagnostics can include without limitation detection of markers of disease, prenatal diagnostics for identification of potential developmental abnormalities, and point of care testing.

In a further aspect, detection of target sequences in a sample can be used to analyze genetic variation, including SNPs, insertions, and deletions.

Decorated nucleic acids of the invention are particularly useful for detecting target sequences, because the information present in the intact double stranded molecules provides the contextual information necessary for generating accurate information. In addition, since decorated nucleic acids of the invention are generally longer than target nucleic acids used in conventional assays, fewer (but longer) probes can be used per reaction to detect a target sequence.

For targeted disease or pathway analysis such as cancer diagnostics, only a predefined set of about 100-1000 genes may be required for diagnostic testing. In one aspect, as describe in further detail above, a sample of genome fragments used to generate decorated nucleic acids of the invention is enriched for the genomic region of interest, thus reducing the required sequencing effort 10-100 fold relative to sequencing the entire genome. Targeted fragment selection can optimize the nucleic acid population used in diagnostic applications by reducing or eliminating the occurrence of false negatives.

In one aspect of the invention, target sequence detection involves gene expression analysis by quantification of a specific message. In this aspect, cDNA is generated using methods well known in the art from mRNA obtained from a sample. This cDNA can be used to generate decorated nucleic acids using methods described above. Analysis of decorated nucleic acids generated from such cDNA provides representative sequence information the presence and relative abundance of specific splice variants within a sample. Since cDNA generated from mRNA will start at the same point, spatial localization of sequence information obtained from such cDNA is relatively straightforward. Longer probes may be of particular use in such analyses, because the optimized enriched population of target nucleic acids will make it more likely that these longer probes will have enough 'hits' to provide sufficient coverage.

The methods of the present invention can be used to identify individual mRNA molecules from a biological sample. The majority of full-length mRNAs from any biological sample are longer than 2 kb. Since unique patterns of decoration (patterns of labeling with probes) can be generated for approximately 2 kb fragments in one reaction, the assay methods of the claimed invention are particularly useful in the high throughout, parallel processing of transcript information from a sample. The resolution of detecting probes, particularly the number of bases between two bound probes that can be discriminated optically or tolerated physically, and the number of differentially labeled probes (dyes or intensity) that are used in a single assay reaction are both parameters that are of use in optimizing this aspect of the invention. These parameters can be optimized for the number and quantity of transcripts that are to be identified in a given biological sample.

Flow analysis of signature probes provides an efficient way to generate comprehensive digital gene expression data, including the identification of splice variants and any potential "gene editing" that occurred during transcription. By analyzing approximately 1 million 100 kb fragments per cDNA prep (100 cells) per signature (equivalent to 15× whole genome coverage), a single messenger per cell will be examined 100 times, on average. Such redundancy provides highly accurate counting of each messenger from each gene, especially if 4-8 different signatures are prepared on 4-8 aliquots of ~100 cells each prepared from the same tissue.

Detection of Non-Stretched Decorated Nucleic Acids

In one aspect, decorated nucleic acids made using the methods describe above are used to obtain sequence information without being stretched on a substrate. Often, decorated nucleic acids in solution can be used with certain combinations of probes and sets of probes to provide sequence information.

In an exemplary aspect, "signature probes" and "diagnostic probes" are utilized in a single assay to detect target sequences. By "signature probe" is meant a probe complementary to a target sequence, generally a unique sequence, such as a genetic marker for disease. By "diagnostic probe" is meant a probe comprising a sequence that complementary to a sequence that allows the diagnostic probe to hybridize adjacent to the signature probe. Diagnostic probes will generally provide information on any polymorphisms or sequences associated with a genetic mutation. For example, to detect the presence of a SNP, two differentially labeled diagnostic probes can be used, such that detection of one probe over the other indicates whether a polymorphism present in the sample. In such assays, the diagnostic probes are differentially labeled from the signature probes to provide simultaneous identification of signature sequences and identification of diagnostic sequences (e.g., SNPs or sequences associated with a genetic mutation) on the target nucleic acids.

In one example, a four color system is used in the combinatorial assay of the invention: two colors are used to label signature probes and two colors used to label diagnostic probes that identify sequence variants in a particular genomic location. In one embodiment, the number of fragments to be analyzed can be reduced by enriching for specific fragments harboring the gene or genes of interest. Methods of enriching for specific target sequences are discussed in more detail above.

In an exemplary embodiment, a prenatal diagnostic panel including 100 critical genes can be interrogated simultaneously using the assay methods of the invention. Each gene may have a specific site that is being interrogated, or each gene may have several diagnostic sites each. By preparing two probes with different colors for each diagnostic site, a set of 2×~1000 probes can be used in the same assay. Optimally the diagnostic sites are 500 bases or more apart to allow for individual hybridization of the probes and optimal resolution of the imaging of any hybridization events. For greater accuracy, each diagnostic site can be probed ~20 times on average to minimize the potential impact of false negative scores on the final results.

Signatures created using 2-probe signatures provide unique mapping of genomic fragments as short as about 20 kb (even assuming a ~20% false negative probe scoring rate). One way to generate 2-probe signatures is to mix two 6-mers labeled with the same color. The other is to have less frequent probe sites and more variable distance measurements, e.g., 6-8 frequent distances. For the first case, the frequency of binding of the two probes is 1 in ~$4^{22}$, i.e., equivalent to the binding frequency of a 22-mer. 22-mers statistically occur once in a genome that is >1,000 times longer than the human genome.

In one embodiment, sequence information is obtained from decorated nucleic acids through sequencing-by-synthesis methods. In such methods, primers hybridize to probes on the decorated nucleic acid and their extension by a polymerase is detected. Sequencing-by-synthesis methods are well known in the art and are described for example in U.S. Pat. Nos. 4,971,903; 6,828,100; 6,833,256; 6,911,345, as well as in Hyman, Anal. Biochem. 174:423 (1988); Rosenthal, International Patent Application Publication 761107 (1989); Metzker et al., Nucl. Acids Res. 22:4259 (1994); Jones, Biotechniques 22:938 (1997); Ronaghi et al., Anal. Biochem. 242:84 (1996); Ronaghi et al (1998), Science, 281: 363-365; Nyren et al., Anal. Biochem. 151:504 (1985); and Li et al, Proc. Natl. Acad. Sci., 100: 414-419 (2003), each of which is hereby incorporated by reference in its entirety for all purposes and in particular for all teachings related to sequencing methods, including sequencing-by-synthesis methods.

V. Systems

In one aspect, the present invention provides systems for obtaining sequence information from decorated nucleic acids.

In an exemplary aspect, such systems will include assemblies that comprise nanostructures. In one embodiment, these systems will further include components for bridging the length scale extremes from the pipette to the nanochannel, from the millimeter to the nanometer scale. In one embodiment, systems of the invention include a package comprising an inlet port that leads to nanochannels, which in turn lead to an outlet port. In a further aspect, the system includes an imaging system combined with a hardware setup designed to accommodate and run a chip comprising assemblies comprising nanochannels. In a still further aspect, systems include image acquisition software and a user interface to ensure ease of use and efficient data collection.

In another exemplary aspect, systems of the invention will include assemblies comprising a substrate such as that illustrated in FIG. 13, which will comprise a non-patterned region and a set of linear features. Such systems may further include mechanisms for flowing nucleic acid-containing solutions across the substrate, such as pumps, electrodes, valves, as well as mechanisms for tilting the substrate to allow gravity to cause the flow of nucleic acids through the non-patterned region to the linear features. In a further aspect, such systems will also include an imaging system combined with a hardware setup designed to accommodate and run a chip comprising assemblies comprising nanochannels. In a still further aspect, systems include image acquisition software and a user interface to ensure ease of use and efficient data collection.

VI. Exemplary Embodiments

Figure 9B:
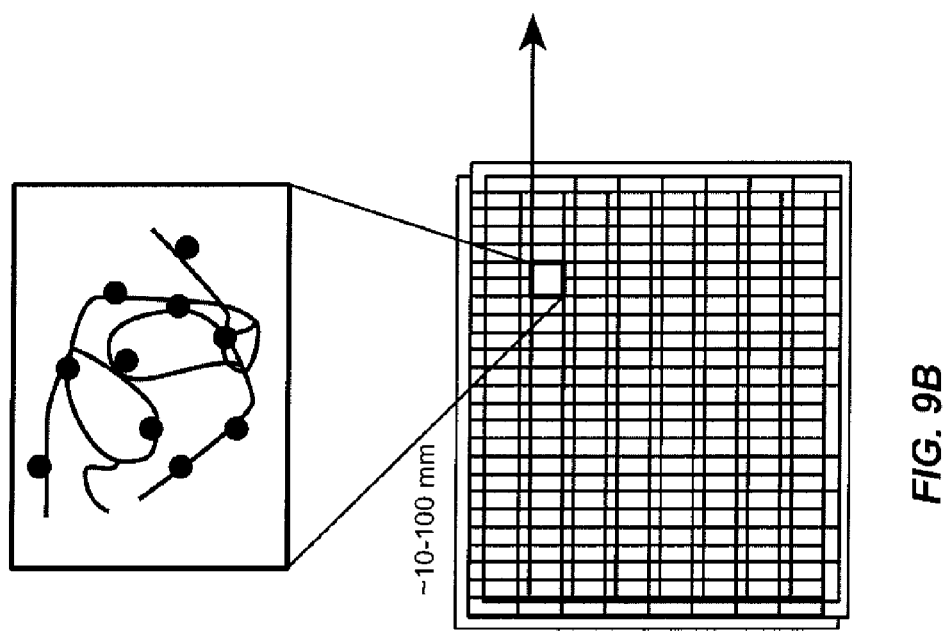
FIG. 9 is a schematic illustration of an exemplary embodiment of the invention. Genomic DNA is isolated from a drop of blood (FIG. 9A). This DNA is fragmented and then decorated with labeled probes (FIG. 9B). The decorated nucleic acids are then applied to a substrate, such as a nanochip (FIG. 9C), which stretches the DNA. DNA signatures can be extracted and analyzed from the images of the stretched DNA by processing the multicolor images to define the order and optionally the relative distances of the probes decorating each molecule (FIG. 9D). The sequence of the different fragments can then be mapped based on detection of the order, and optionally the relative distance, or the probes along the fragments. In one embodiment, the sequences of the individual fragments are aligned against a reference sequence (SEQ ID NO: 1 AND 2).
Figure 9A:
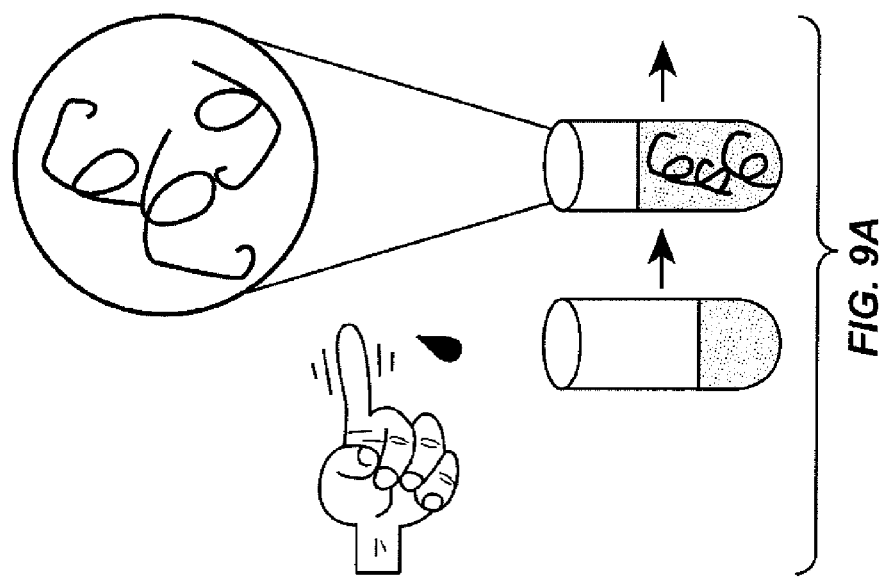
Figures 9C, 9D:
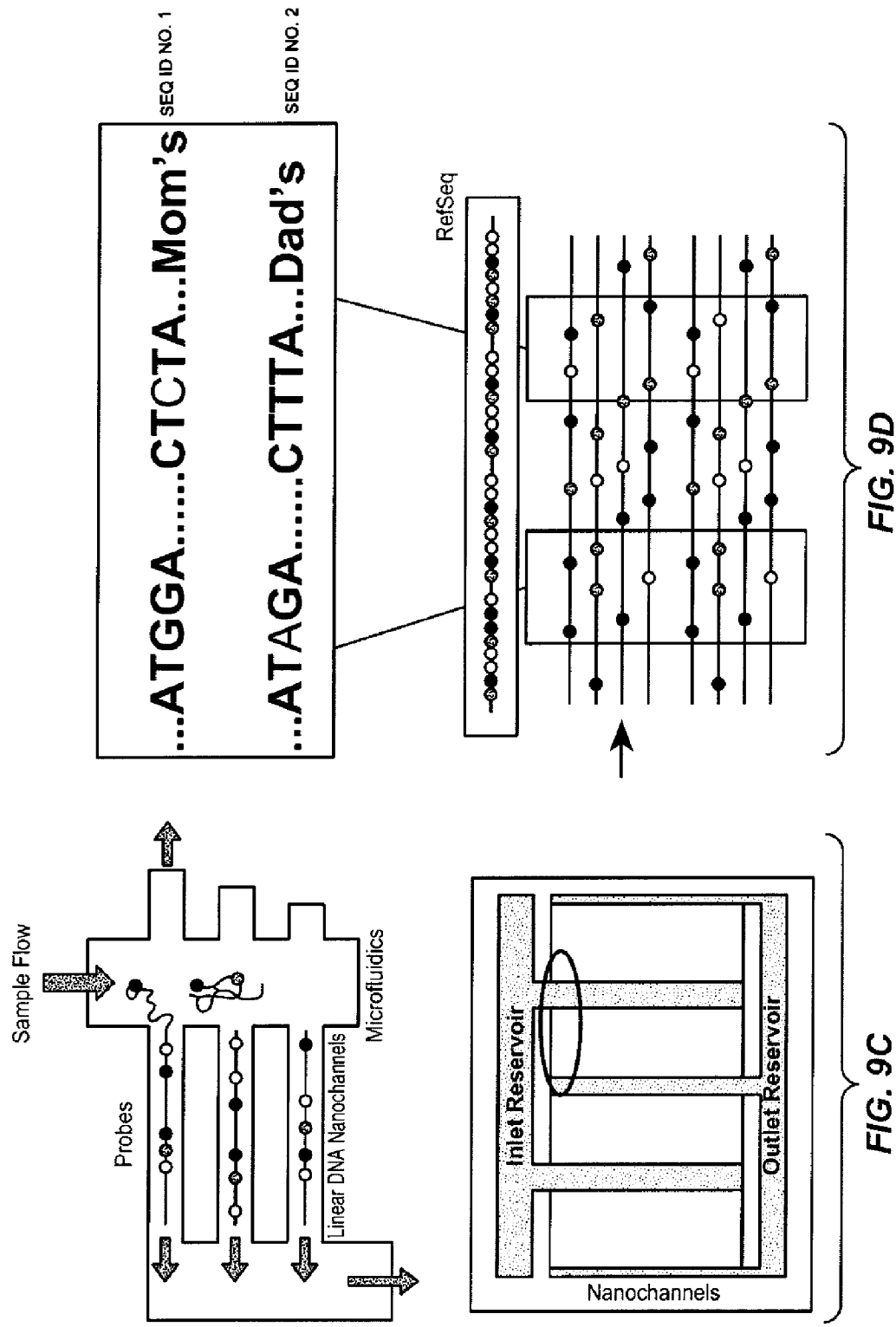

An exemplary embodiment of the invention is depicted in FIG. 9. Nucleic acids, for example DNA, can be isolated from a sample, such as a drop of blood (FIG. 9A). A drop of blood will contain about 100,000 cells, from which genomic DNA can be isolated. The DNA can then be fragmented into approximately 1000 fragments per chromosome. Such fragments are generally about 100 kb in length. The fragments can then be dispensed with 4 or more differentially labeled probes (which will generally have about 5-7 informative bases) into a multiwell plate (FIG. 9B). The probes will hybridize or ligate to complementary sequences in the fragments as described in further detail above to form decorated fragments. These decorated nucleic acids are then loaded onto a substrate—as depicted in FIG. 9C, such a substrate can be a nanochannel chip, although it will be appreciated that any number of substrates can be used, as described in further detail above. Such a nanochannel chip can in some embodiments have approximately 4000 100 nm×50 micron channels. The DNA molecules are stretched by the flow force in the narrow channels. Imaging of the stretched DNA can be obtained—in some embodiments, such imaging is accomplished at approximately 40 frames per second. In further embodiments, multiple imagers may be used in parallel to obtain images from the stretched DNA. DNA signatures can be extracted and analyzed from the images of the stretched DNA by processing the multicolor images to define the order and optionally the relative distances of the probes decorating each molecule (FIG. 9D). Such unique signatures will generally have approximately a 500 base resolution and can be mapped to a reference sequence ("RefSeq in FIG. 9D). A precise genome map can thus be obtained from the processed images. Complete sequence can be assembled for each parental chromosome in the patient's cells from millions of 100 kb overlapping signatures.

In one aspect, the present invention provides a composition that comprises a substrate comprising a plurality of locations. Each location of the substrate comprises a single molecule of stretched decorated nucleic acids. Each of the stretched nucleic acids comprises a plurality of probes, and the stretched decorated nucleic acids are positioned on the substrate in such a way that they are optically resolvable.

In a further embodiment and in accordance with the above, each of the plurality of locations in a composition of the invention is a nanochannel.

In a still further embodiment and in accordance with any of the above, the substrate comprises hydrophobic regions alternating with hydrophilic regions. In a further embodiment, such alternating regions may be provided in a linear pattern.

In a further aspect and in accordance with any of the above, stretched decorated nucleic acids of the invention are formed by: (i) nicking a nucleic acid to form a nicked nucleic acid, (ii) adding an exonuclease to the nicked nucleic acid to form a gapped nucleic acid, and (iii) adding a first set of labeled probes to the gapped nucleic acid such that at least one of the first set of labeled probes hybridizes to single stranded areas of said gapped nucleic acid. In a further embodiment, the first set of probes comprises a plurality of non-overlapping probe sequences. In a still further embodiment, each probe sequence comprises a unique label. In exemplary embodiments, steps (i) through (iii) are performed simultaneously or are performed sequentially.

In a further aspect and in accordance with any of the above, subsequent to the addition of a first set of labeled probes to a gapped nucleic acid, a second set of labeled probes is added to the gapped nucleic acid to hybridize to single stranded areas of the gapped nucleic acid. Such second set of probes may also comprise a plurality of non-overlapping probe sequences which each comprise a unique label. In a further embodiment, probes from the first set and from the second set that are hybridized to adjacent positions of the gapped nucleic acid will hybridize to each other.

In a further aspect, stretched decorated nucleic acids of the invention are formed by (i) providing a double stranded nucleic acid; (ii) adding a first set of recA invasive labeled probes to the double stranded nucleic acid to form D-loops within the double stranded nucleic acid, thus forming a decorated nucleic acid; and (iii) stretching the decorated nucleic acid to form a stretched decorated nucleic acid. In this aspect of the invention, the recA invasive labeled probes comprise a plurality of non-overlapping probe sequence and each probe sequence comprises a unique label. Such probes hybridize to sequences in the double stranded nucleic acid that are complementary to the probe sequences. In a further embodiment, a second set of recA invasive probes is added to the double stranded nucleic acid to form double D-loops within the double stranded nucleic acid. In such an embodiment, the second set of recA invasive labeled probes are substantially complementary to the first set of recA invasive labeled probes. In a still further embodiment, the recA invasive labeled probes used in accordance with the invention comprise at least one modification selected from: locked nucleic acid, peptide nucleic acid and phosphorothioate nucleic acid.

In a further embodiment an in accordance with any of the above, gaps within a nucleic acid are repaired by adding a polymerase, dNTPs and a ligase. In a further embodiment, all gaps within the nucleic acid are repaired. In a still further embodiment, only a portion of the gaps of are repaired.

In a further aspect and in accordance with any of the above, the present invention provides methods for detecting the presence of a target nucleic acid by using stretched decorated nucleic acids of the invention. In one embodiment, a substrate comprising the stretched decorated nucleic acids is provided and at least one of the labeled probes of the stretched decorated nucleic acids is detected, thereby indicating the presence of the target nucleic acid.

In a further embodiment and in accordance with any of the above, decorated nucleic acids of the invention are stretched by applying the nucleic acids to a nanochannel. In a still further embodiment, different decorated nucleic acids may be applied to an assembly comprising a plurality of nanochannels. In a still further embodiment, different decorated nucleic acids may be applied sequentially through the same nanochannel.

In a further embodiment and in accordance with any of the above, decorated nucleic acids of the invention are stretched by applying the nucleic acids to a flowthrough system that comprises surface that comprises hydrophobic regions alternating with hydrophilic regions. In a still further embodiment, the alternating hydrophobic and hydrophilic regions are arranged in a linear pattern. In an exemplary embodiment, different decorated nucleic acids are applied to different flowthrough systems. In an exemplary embodiment, a plurality of decorated nucleic acids are applied to the same flowthrough system.

In a still further embodiment and in accordance with any of the above, the stretched decorated nucleic acids of the invention are substantially double stranded.

In a further embodiment and in accordance with any of the above, stretched decorated nucleic acids of the invention comprise probes that comprise a plurality of fluorophores.

In a still further embodiment and in accordance with any of the above, stretched decorated nucleic acids of the invention comprise probes at least one of which is a dendrimeric probe. In a still further embodiment, the dendrimeric probe is a branched nucleic acid.

In a further embodiment and in accordance with any of the above, stretched decorated nucleic acids of the invention comprise probes that are hexamers.

In a further embodiment and in accordance with any of the above, stretched decorated nucleic acids of the invention are formed from nucleic acids obtained from a sample. In a still further embodiment, the sample is obtained from a target organism.

In a further embodiment, detecting the presence of a target nucleic acid in accordance with the present invention comprises identifying the presence of a pathogen in the sample.

In a still further embodiment and in accordance with any of the above, detecting the presence of a target nucleic acid identifies the source of that target nucleic acid.

In a further aspect and in accordance with any of the above, stretched decorated nucleic acids of the invention are used to obtain sequence information from a target nucleic acid. In this aspect, a substrate comprising stretched decorated nucleic acids of the invention is provided. As described herein, the stretched decorated nucleic acids of the invention will generally comprise a plurality of labeled probes. The order of the labeled probes on the stretched decorated nucleic is determined, and that order thereby provides sequence information for the target nucleic acid.

In a further embodiment and in accordance with any of the above, different stretched nucleic acids comprise a different set of labeled probes, and determining the order of each of the different set of labeled probes provides information about the sequence of a target nucleic acid. In a still further embodiment, each set of labeled probes comprises a plurality of non-overlapping probe sequences that are different from the probe sequences of the other sets of labeled probes. In a still further embodiment, each probe sequence comprises a unique label. In a still further embodiment, the set of labeled probes comprises four hexamers.

In an exemplary embodiment and in accordance with any of the above, a plurality of decorated nucleic acids are stretched on a single substrate and the order of probes is determined for one or more of the plurality of nucleic acids. In a further embodiment, the plurality of decorated nucleic acids are obtained from a set of decorated nucleic acids. In a still further embodiment, the set of decorated nucleic acids are formed from the same target nucleic acid.

In an exemplary embodiment and in accordance with any of the above, different decorated nucleic acids are stretched on different substrates, and the order of probes for one or more of the different decorated nucleic acids are determined. In a further embodiment, the different decorated nucleic acids are aliquots from a set of decorated nucleic acids. In a still further embodiment, the set of decorated nucleic acids are formed from the same target nucleic acid.

EXAMPLES

Example 1

Optimizing Buffers for Use in Decorating Nucleic Acids

For methods of decorating nucleic acids that utilize a combination of nicking enzymes, exonucleases and optionally polymerases and nucleotides and/or ligases, a buffer that is compatible for all four of these enzymes is needed. The following buffer is of use in the present invention:

| REAGENT | FINAL CONCENTRATION [1X] |
| --- | --- |
| Water | n/a |
| Trizma hydrochloride, pH 7.9 (@25° C.) | 10 mM |
| Sodium Chloride | 50 mM |

-continued

| REAGENT | FINAL CONCENTRATION [1X] |
| --- | --- |
| Magnesium chloride | 10 mM |
| DTT | 1 mM |
| dNTPs | 33 mM |
| ATP | 100 mM |

Example 2

Restriction Enzyme Digestion of ApoB DNA Upon Treatment with Nicking Enzymes, Exo III and Probe Hybridization An ApoB 4.86 kb PCR fragment was nicked with Nb.BbvCI or Nt.BbvCI at 37° C. for 2 hours followed by exo III treatment for 2 minutes at 22° C. The nuclease was then heat-inactivated at 80° C. for 20 minutes. A 24-mer Nb.BbvCI probe was added to the exo III mixture for probe hybridization at 25° C. for 50 minutes followed by 15 minutes of T4 ligase treatment. Restriction enzyme digestion demonstrates that the 24-mer Nb.BbvCI probe hybridized to the gaps generated at the Nb.BbvCI nicks, but not the gaps generated at the Nt.BbvCI nicks.

Example 3

Detecting Nucleic Acids Decorated with Qdots

The decorated nucleic acids (Lambda DNA) were attached to a coverslip coated with poly(allylamine) and poly(acrylic acid), resulting in their stretching. Nucleic acids were decorated with probes labeled with Qdot 605 (Invitrogen) with biotin alkyl amines attached to the 5' ends. The decorated nucleic acids were stained with the intercalating dye YOYO-1. YOYO-1 was imaged with 488 nm excitation and 520 nm emission. The Qdot 605 was imaged with 590 nm and 630 nm emission. The images were overlaid to show co-localization of the probes and the double-stranded nucleic acid. Qdots are bright and allow for visualization of probes in the expected locations of nucleic acids nicked at a specific site with Nt.BspQI and with a gap opened by limited treatment with exonuclease III.

In some experiments, the decorated nucleic acids were diluted to 100 pM in sterile TE buffer (10 mM Tris, pH 8.0, 1 mM EDTA) and stained with YOYO-1 iodide (300 pM) for 1 hour before imaging.

In some experiments, the coverslips were treated by multiple steps with poly(allylamine) and poly(acrylic acid) immersions to minimize background emission and provide uniform stretching of DNA molecules.

The DNA solution was pipetted between the coverslip and a pre-cleaned glass slide. The strong capillary flow caused the DNA fragments to stretch.

Example 4

Assembly of DNA with a Single Base Substitution

A segment of human genomic DNA to be sequenced has the following wild-type reference sequence as determined through compilation of empirical data:

(SEQ ID NO: 3)
BBBBBBBBBTCGAATGTAACGTACGGCBBBBBBBBBBB

The following probes used in a direct hybridization method determine the composite signature of the corresponding segment of DNA in a patient's sample:

```
BBBBBBBB TCGAATGTAACGTACGGCBBBBBBBBBBBB  (SEQ ID NO: 3) reference
         TCGAAT
          CGAATG
           GAATGT                positive probes
            AATGTA
             ATGTAC
              TGTAAC
               GTAACG
                TAACGT
                 AACGTA
                  ACGTAC
                   CGTACG
                    GTACGG
BBBBBBBB TCGAATGTAGCGTACGGBBBBBBBBBBBB  (SEQ ID NO: 4) sample
```

Mutation of A (underlined) in the reference to G (underlined) in the sample produces six new overlapping 6-mers (highlighted) that are not present in the reference. At the same time, there are six reference 6-mers that become negative:

<div align="center">

ATGTAA

TGTAAC

GTAACG

TAACGT

AACGTA

ACGTAC

</div>

This redundancy of positive and negative probes assures high accuracy of base determination.

Although described in some detail for purposes of illustration, it will be readily appreciated that a number of variations known or appreciated by those of skill in the art may be practiced within the scope of present invention. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

<div align="center">SEQUENCE LISTING</div>

```
<160> NUMBER OF SEQ ID NOS: 4

<210> SEQ ID NO 1
<211> LENGTH: 16
<212> TYPE: DNA
<213> ORGANISM: Artificial Sequence
<220> FEATURE:
<223> OTHER INFORMATION: Exemplary sample sequence
<220> FEATURE:
<221> NAME/KEY: misc_feature
<222> LOCATION: (6)...(11)
<223> OTHER INFORMATION: N is A, C, T or G

<400> SEQUENCE: 1
atggannnnn nctcta                                                   16

<210> SEQ ID NO 2
<211> LENGTH: 16
<212> TYPE: DNA
<213> ORGANISM: Artificial Sequence
<220> FEATURE:
<223> OTHER INFORMATION: Exemplary sample sequence
<220> FEATURE:
<221> NAME/KEY: misc_feature
<222> LOCATION: (6)...(11)
<223> OTHER INFORMATION: N is A, C, T or G

<400> SEQUENCE: 2
atagannnnn nctta                                                    16

<210> SEQ ID NO 3
<211> LENGTH: 39
<212> TYPE: DNA
<213> ORGANISM: Artificial Sequence
<220> FEATURE:
<223> OTHER INFORMATION: Exemplary reference sequence
```

```
-continued

<220> FEATURE:
<221> NAME/KEY: misc_feature
<222> LOCATION: (1)...(9)
<223> OTHER INFORMATION: N is A, C, T or G
<220> FEATURE:
<221> NAME/KEY: misc_feature
<222> LOCATION: (28)...(39)
<223> OTHER INFORMATION: N is A, C, T or G

<400> SEQUENCE: 3
nnnnnnnnnt cgaatgtaac gtacggcnnn nnnnnnnnn                                39

<210> SEQ ID NO 4
<211> LENGTH: 39
<212> TYPE: DNA
<213> ORGANISM: Artificial Sequence
<220> FEATURE:
<223> OTHER INFORMATION: Exemplary sample sequence
<220> FEATURE:
<221> NAME/KEY: misc_feature
<222> LOCATION: (1)...(9)
<223> OTHER INFORMATION: N is A, C, T or G
<220> FEATURE:
<221> NAME/KEY: misc_feature
<222> LOCATION: (27)...(39)
<223> OTHER INFORMATION: N is A, C, T or G

<400> SEQUENCE: 4
nnnnnnnnnt cgaatgtagc gtacggnnnn nnnnnnnnn                                39
```

What is claimed:

1. A method of obtaining sequence information from a nucleic acid comprising:
   a) providing a double stranded nucleic acid that comprises single-stranded regions;
   b) contacting the nucleic acid provided in step (a) with labeled probes under conditions whereby the labeled probes hybridize to single-stranded but not double stranded regions of the nucleic acid, thereby forming a decorated nucleic acid;
   c) stretching said decorated nucleic acid on a substrate; and
   d) detecting said labeled probes on said stretched decorated nucleic acid;
   wherein the labeled probes that hybridize in step (b) comprise sequences that are complementary to the single-stranded regions to which they hybridize.

2. The method of claim 1, wherein step (a) comprises contacting said nucleic acid with a nicking enzyme.

3. The method of claim 2, wherein step (a) comprises contacting the nucleic acid with an exonuclease to widen nicks created by the nicking enzyme.

4. The method of claim 3, wherein step (a) comprises contacting the nucleic acid with a polymerase and dNTPs under conditions whereby gaps in the nucleic acid are repaired.

5. The method of claim 1, wherein a preparation comprising said nucleic acid is separated into a plurality of aliquots, and different probes having different sequences are added to each aliquot to form different decorated nucleic acids, wherein said method further comprises stretching each of said decorated nucleic acids on a substrate; and detecting said labels on said decorated nucleic acids.

6. The method of claim 5, wherein the probes added to each aliquot comprise 4 hexamers.

7. The method of claim 5, wherein said decorated nucleic acids are stretched on the same substrate.

8. The method of claim 5, wherein said decorated nucleic acids are stretched on different substrates.

9. The method of claim 1, 7, or 8, wherein said substrates comprise a plurality of nanochannels, and wherein said nucleic acids are within said nanochannels.

10. The method of claim 1, 7, or 8, wherein said substrates comprise a flowthrough system, wherein said flowthrough system comprises a surface comprising hydrophobic regions alternating with hydrophilic regions in a linear pattern.

11. The method of claim 1, wherein said sequence information comprises a sequence signature.

12. The method of claim 1, wherein at least one of said labeled probes comprises a plurality of fluorophores.

13. The method of claim 1, wherein said labeled probes comprise dendrimeric probes.

14. The method of claim 1, wherein said labeled probes comprise pairs of complementary probes.

15. A method of forming a decorated nucleic acid, said method comprising:
   a) nicking a nucleic acid to form a nicked nucleic acid;
   b) contacting said nicked nucleic acid with labeled probes under conditions whereby the labeled probes hybridize in a sequence-specific manner to single-stranded but not double stranded areas of the nicked nucleic acid, thereby forming said decorated nucleic acid; and
   c) stretching said decorated nucleic acid on a substrate;
   wherein said labeled probes each comprise a sequence of at least 5 nucleotides in length.

16. The method of claim 1, wherein said labeled probes comprise a plurality of non-overlapping sequences.

17. The method of claim 16, wherein each non-overlapping probe sequence comprises a unique label.

18. The method of claim 16, wherein said labeled probes comprise a plurality of hexamers, each with a different label.

19. The method of claim 2, wherein prior to step (c), the nucleic acid is contacted with a ligase under conditions whereby hybridized probes are ligated to neighboring 5' or 3' termini within said gap.

20. The method of claim 1, wherein step (d) comprises determining the order of said labeled probes on said stretched decorated nucleic acid.

21. The method of claim 1, wherein step (d) comprises determining the spacing of said labeled probes on said stretched decorated nucleic acid.

22. The method of claim 1, further comprising detaching said labeled probes from the stretched nucleic acid, and then contacting the nucleic acid with a second set of labeled probes.

23. The method of claim 5, comprising determining the order of said labeled probes on said stretched decorated nucleic acids.

24. The method of claim 5, comprising determining the spacing of said labeled probes on said stretched decorated nucleic acids.

25. The method of claim 15, further comprising determining the order of said labeled probes on said stretched decorated nucleic acid.

26. The method of claim 15, further comprising determining the spacing of said labeled probes on said stretched decorated nucleic acid.

27. The method of claim 15, wherein prior to step (b), the nicked nucleic acid is contacted with an exonuclease to form a gapped nucleic acid.

28. The method of claim 27, wherein prior to step (b), the gapped nucleic acid is contacted with a polymerase and dNTPs under conditions whereby gaps in the nucleic acid are repaired.

29. The method of claim 28, wherein said labeled probes comprise a plurality of non-overlapping sequences.

30. The method of claim 29, wherein each non-overlapping probe sequence comprises a unique label.

31. The method of claim 29, wherein said labeled probes comprise a plurality of hexamers, each with a different label.

32. The method of claim 15, wherein prior to step (c), the nucleic acid is contacted with a ligase under conditions whereby hybridized probes are ligated to neighboring 5' or 3' termini within said gap.

33. The method of claim 1, wherein the labeled probes are 3 to 100 bases in length.

34. The method of claim 1, wherein the labeled probes are 5 to 90 bases in length.

35. The method of claim 1, wherein the labeled probes are 5 to 14 bases in length.

36. The method of claim 1, wherein the labeled probes are 20 to 60 bases in length.

* * * * *